US008168770B2

(12) United States Patent
Minoprio et al.

(10) Patent No.: US 8,168,770 B2

(45) Date of Patent: May 1, 2012

(54) CLONING, SEQUENCING AND EXPRESSION OF A GENE ENCODING AN EUKARYOTIC AMINO ACID RACEMASE, AND DIAGNOSTIC, THERAPEUTIC, AND VACCINATION APPLICATIONS OF PARASITE AND VIRAL MITOGENS

(75) Inventors: Paolo Minoprio, Villiers sur Mame (FR); Mario Arala-Chaves, Lisboa (PT); Eduarda Maria Santos Dores Arala Chaves, legal representative, Lisboa (PT); Rui Mario Dores Arala Chaves, legal representative, Lisboa (PT); Antonio Coutinho, Paris (FR); Bernardo Reina San Martin, New York, NY (US); Catherine Rougeot, Chevreuse (FR); Wim Degrave, Bagneux (FR); Alain Cosson, Neuilly sur Mame (FR)

(73) Assignees: Centre National de la Recherche Scientifique, Paris (FR); Instituto Gulbekian De Cienca, Oeiras (PT)

( * ) Notice: Subject to any disclaimer, the term of this patent is extended or adjusted under 35 U.S.C. 154(b) by 473 days.

(21) Appl. No.: 11/378,706

(22) Filed: Mar. 17, 2006

(65) Prior Publication Data

US 2006/0292596 A1 Dec. 28, 2006

Related U.S. Application Data

(60) Continuation of application No. 10/662,437, filed on Sep. 16, 2003, now abandoned, which is a division of application No. 09/725,945, filed on Nov. 30, 2000, now Pat. No. 6,713,617.

(60) Provisional application No. 60/168,631, filed on Dec. 3, 1999, provisional application No. 60/220,207, filed on Jul. 24, 2000, provisional application No. 60/221,117, filed on Jul. 27, 2000.

(51) Int. Cl.

*C07H 21/04* (2006.01)
*C07H 21/02* (2006.01)
*C07H 21/00* (2006.01)
*A61K 39/00* (2006.01)

(52) U.S. Cl. .................... 536/23.2; 536/23.1; 536/23.7; 424/269.1

(58) Field of Classification Search ........................ None
See application file for complete search history.

(56) References Cited

U.S. PATENT DOCUMENTS

| | | | |
|---|---|---|---|
| 6,713,617 | B2 | 3/2004 | Minoprio et al. |
| 2005/0090656 | A1 | 4/2005 | Minoprio et al. |
| 2005/0130166 | A1 | 6/2005 | Minoprio et al. |

FOREIGN PATENT DOCUMENTS

| | | | |
|---|---|---|---|
| JP | 07 289275 | A | 7/1995 |
| WO | WO 94 25606 | A | 4/1994 |
| WO | WO 0140449 | A2 | 6/2001 |
| WO | WO 0140449 | A3 | 6/2001 |

OTHER PUBLICATIONS

Johnston et al (BioEssays 21:131-147, 199, p. 131-147).*
Overbeek (1994, "Factors affecting transgenic animal production," Transgenic animal technology, pp. 96-98).*
Wall, (1996 Theriogenology, vol. 45, pp. 57-68).*
Houdebine, (1994, J. Biotech. vol. 34, pp. 269-287, specifically p. 281).*
Kappel, (1992, Current Opinions in Biotechnology, vol. 3, pp. 548-553).*
Cameron, (1997, Molec. Biol. 7, pp. 253-265).*
Niemann, (1997, Transg. Res. 7, pp. 73-75).*
Mullins (1993, Hypertension, vol. 22, pp. 630-633).*
Mullins (1990, Nature, vol. 344, 541-544).*
Hammer (1990, Cell, vol. 63, 1099-1112).*
Mullins, (1989, EMBO J., vol. 8, pp. 4065-4072).*
Taurog, (1988, Jour. Immunol., vol. 141, pp. 4020-4023).*
Mullins (1996, J. Clin. Invest. vol. 98, pp. S37-S40).*
Billaut-Mulot et al (Biol. Cell, 1994, 82(1):39-44).*
Stratagene, (Prime-It kit , 1991).*
Johnston et al (BioEssays 21:131-147, 199, p. 131-147).*
Lodish et al., Mol. Cell Biol., 3rd ed. Scientific American Books, NY, 1995).*
Lodish et al., Mol. Cell Biol., 3rd ed. Scientific American Books, NY, 1995).*
Verdun et al (Infection and Immunity, Nov. 1998, 66(11):5393-8).*
Genbank accession No. AI562488, 1999.*
U.S. Appl. No. 11/388,474, filed Mar. 23, 2006, Minoprio et al.
U.S. Appl. No. 11/384,144, filed Mar. 17, 2006, Minoprio et al.
Aguero, et al., "*T. cruzi* Epimastigote Normalized cDNA Library *Trypanosoma cruzi* cDNA clone G47H8, Genomic Survey Sequence," Genbank Accession No. AQ908238, Jan. 9, 2001.
Aguero, et al., "*T. cruzi* Epimastigote Normalized cDNA Library *Trypanosoma cruzi* cDNA clone G35A1, Genomic Survey Sequence," Genbank Accession No. AQ903011, Jan. 9, 2001.
Porcel, et al., "*T. cruzi* Epimastigote Normalized cDNA Library *Trypanosoma cruzi* cDNA clone 23b1 5', mRNA Sequence," Genbank Accession No. AI057768, Sep. 21, 2000.
Porcel, et al., "*T. cruzi* Epimastigote Normalized cDNA Library *Trypanosoma cruzi* cDNA clone 24f18 5', mRNA Sequence," Genbank Accession No. AI057684, Sep. 21, 2000.
Porcel, et al., "*T. cruzi* Epimastigote Normalized cDNA Library *Trypanosoma cruzi* cDNA clone 18i7 5', mRNA Sequence," Genbank Accession No. AI053153, Sep. 21, 2000.
Porcel, et al., "*T. cruzi* Epimastigote Normalized cDNA Library *Trypanosoma cruzi* cDNA clone 23d19 5', mRNA Sequence," Genbank Accession No. AI057805, Sep. 21, 2000.

(Continued)

*Primary Examiner* — Vanessa L. Ford

(74) *Attorney, Agent, or Firm* — Finnegan, Henderson, Farabow, Garrett & Dunner LLP

(57) ABSTRACT

A method of preventing or inhibiting infection by a parasite or virus in vivo comprising administering to a human in need thereof a parasite or virus mitogen in a sub-mitogenic amount sufficient to induce a protective immune response against the parasite or virus in the human.

15 Claims, 39 Drawing Sheets

OTHER PUBLICATIONS

Verdun, et al., "*T. cruzi* Epimastigote Normalized cDNA Library *Trypanosoma cruzi* cDNA clone 1769 5', mRNA Sequence," Genbank Accession No. AA952585, Oct. 29, 1998.
Verdun, et al., "*T. cruzi* Epimastigote Normalized cDNA Library *Trypanosoma cruzi* cDNA clone 1816 5', mRNA Sequence," Genbank Accession No. AA952632, Oct. 29, 1998.
Verdun, et al., "*T. cruzi* Epimastigote Normalized cDNA Library *Trypanosoma cruzi* cDNA clone 500 5', mRNA Sequence," Genbank Accession No. AA882923, Oct. 29, 1998.
Verdun, et al., "*T. cruzi* Epimastigote Normalized cDNA Library *Trypanosoma cruzi* cDNA clone 2013 5', mRNA Sequence," Genbank Accession No. AI562488, Mar. 25, 1999.
Aguillon et al., "Purification and Preliminary Sequencing of Tc45, An Immunodominant *Trypanosome cruzi* Antigen: Absence of Homology with Cruzipain, Cruzain, and a 46-Kilodalton Protein," *Am. J. Trop. Med. Hyg.*, Aug. 1995, pp. 211-215, vol. 53, No. 2.
Billaut-Mulot et al., "Molecular and Immunological Characterization of a *Trypanosoma cruzi* Protein Homologous to Mammalian Elongation Factor 1 Gamma," *Biol. Cell.*, 1994, pp. 39-44, vol. 82, No. 1.
Chamond, et al., "Biochemical Characterization of Proline Racemases from the Human Protozoan Parasite *Trypanosoma cruzi* and Definition of Putative Protein Signatures," *J. Biol. Chem.*, May 2003, pp. 15484-15494, vol. 278, No. 18.
Cheng, et al., "A Eukaryotic Alanine Racemase Gene Involved in Cyclic Peptide Biosynthesis," *J. Biol. Chem.*, Feb. 2000, pp. 4906-4911, vol. 275, No. 7.
Cook, et al., "Direct Calcium Binding Results in Activation of Brain Serine Racemase," *J. Biol. Chem.*, Aug. 2002, pp. 27782-27792, vol. 277, No. 31.
Cordeiro Da Silva et al., "A 24 000 MW *Trypanosoma cruzi* antigen is a B-cell activator," *Immunology*, Jun. 1998, pp. 189-196, vol. 94, No. 2.
Hoppner, W., "Clinical Impact of Molecular Diagnostics in Endocrinology. Polymorphisms, Mutations and DNA Technologies," *Horm. Res.*, 2002, pp. 7-15, vol. 58, Suppl. (Abstract Only).
Kabisch et al., "Identification of D-Proline Reductase from *Clostridium sticklandii* as a Selenoenzyme and Indications for a Catalytically Active Pyruvoyl Group Derived from a Cysteine Residue by Cleavage of a Proprotein," *J. Biol. Chem.*, Mar. 1999, pp. 8445-8454, vol. 274, No. 13.
Kleppe, et al., "Why Do Mutations Cause Disease—A Protein Chemical Perspective," *Tidsskr. Nor. Laegeforen.*, Sep. 2001, pp. 2717-2120, vol. 121, No. 23. (Abstract Only).
Stratagene, Prime-It kit, p. 66, from 1991 Product Catalog.
Uo et al., "Occurrence of Pyridoxal 5'-Phosphate-Dependent Serine Racemase in Silkworm, *Bombyx mori," Biochem. Biophys. Res. Commun.*, May 1998, pp. 31-34, vol. 246, No. 1.
Verdun et al., "Gene Discovery through Expressed Sequence Tag Sequencing in *Trypanosoma cruzi," Infect. Immun.*, Nov. 1998, pp. 5393-5398, vol. 66, No. 11.
Watabe et al., "Identification and Sequencing of a Gene Encoding a Hydantoin Racemase from the Native Plasmid of *Pseudomonas* sp. Strain NS671," *J. Bacteriol.*, Jun. 1992, pp. 3461-3466, vol. 174, No. 11.
International Search Report for PCT/IB 00/02008.

* cited by examiner

Tc MRKSVCPKQKFFFSAFPFFFFFCVFPLISRTGQEKLLFDQKYKIIKGEKKEKKKNQRANRREHQQKREIMRFKKS 75

Cs ---------------------------------------------------------------------MKFSKG 6

Pa ------------------------------------------------------------------------MQR 3

Tc FTCIDMHTEGEAARIVTSGLPHIPGSNMAEKKAYLQENMDYLRRGIMLEPRGHDDMFGAFLFDPIEEGADLGMVF 150

Cs IHAIDSHTMGEPTRIVVGGIPQINGETMADKKKYLEDNLDYVRTALMHEPRGHNDMFGSIITSSNNKEADFGIIF 81

Pa IRIIDSHTGGEPTRLVIGGFPDLGQGDMAERRRLLGERHDAWRAACILEPRGSDVLVGALLCAPVDPEACAGVIF 78

Tc MDTGGYLNMCGHNSIAAVTAAVETGIVSVPAKATNVPVVLDTPAGLVRGTAHLQSGTESEVSNASIINVPSFLYQ 225

Cs MDGGGYLNMCGHGSIGAATVAVETGMVEMVEPVTNIN--MEAPAGLIKAKVMVEN---EKVKEVSITNVPSFLYM 151

Pa FNNSGYLGMCGHGTIGLVASLAHLGRIGPGV------HRIETPVGEVEATLH-------EDGSVSVRNVPAYRYR 140

Tc QDVVVVLPKPYGEVRV*DIAFGGNF*FAIVPAEQLGIDISVQNLSRLQEAGELLRTEINRSVKVQHPQLPHINTVDC 300

Cs EDAKLEVPSLNKTITFDISFGGSFFAIIHAKELGVKVETSQVDVLKKLGIEIRDLINEKIKVQHPELEHIKTVDL 226

Pa RQVSVEVPGI-GRVSGDIAWGGNWFFLVAGH--GQRLAGDNLDALTAYTVAVQQALDD----QDIRGEDGGAIDH 208

Tc VEIYGPPTNPEANYK*NVVIFGNR*QADR SPCGT GTSAKMATLYAKGQLRIGETFVYESILGSLFQGRV--LGEE 371

Cs VEIYDEPSNPEATYKNVVIFGQGQVDR SPCGT GTSAKLATLYKKGHLKIDEKFVYESITGTMFKGRV--LEET 297

Pa IELFAD--DPHADSRNFVLCPGKAYDR SPCGT GTSAKLACLAADGKLLPGQPWRQASVIGSQFEGRYEWLDGQ 279

Tc RIPGVKVPVTKDAEEGMLVVTAEITGKAFIMGFNTMLFDPTDPFKNGFTLKQ* 423

Cs KVGEFD------------AIIPEITGGAYITGFNHFVIDPEDPLKYGFTV*-- 335

Pa PGGPIVPTIRGRAHVSAEATLLLADDDPFAWGIRR*----------------- 314

*FIG. 2*

POLYPYRIMIDINE RICH REGION

SPLICE LEADER ACCEPTOR SITES

SIGNAL

```
CCTTTTCTTTTTAAAAACAAAAAAAATTCCGGGGGAATATGGAACAGGGTATATGCGTAAAAGTGTCTGTCCCAAACAAAAATTTTTT  90
                                                     M  R  K  S  V  C  P  K  Q  K  F  F  12
TTTTCCGCCTTCCCATTTTTTTTTTTTTTTTGTGTGTTTCCCTTGATCTCTCGAACAGGGCAGGAAAAGCTTCTGTTTGACCAAAAATAT  180
 F  S  A  F  P  F  F  F  F  F  C  V  F  P  L  I  S  R  T  G  Q  E  K  L  L  F  D  Q  K  Y  42
AAAATTATTAAGGGCGAGAAAAAAGAAAAGAAAAAAAATCAACGAGCAAACAGGAGAGAACACCAACAAAAAAGGGAAATTATGCGATTT  270
 K  I  I  K  G  E  K  K  E  K  K  K  N  Q  R  A  N  R  R  E  H  Q  Q  K  R  E  I  M  R  F  72
AAGAAATCATTCACATGCATCGACATGCATACGGAAGGTGAAGCAGCACGGATTGTGACGAGTGGTTTGCCACACATTCCAGGTTCGAAT  360
 K  K  S  F  T  C  I  D  M  H  T  E  G  E  A  A  R  I  V  T  S  G  L  P  H  I  P  G  S  N  102
ATGGCGGAGAAGAAAGCATACCTGCAGGAAAACATGGATTATTTGAGGCGTGGCATAATGCTGGAACCACGTGGTCATGATGATATGTTT  430
 M  A  E  K  K  A  Y  L  Q  E  N  M  D  Y  L  R  R  G  I  M  L  E  P  R  G  H  D  D  M  F  132
GGAGCCTTTTTATTTGACCCTATTGAAGAAGGCGCTGACTTGGGCATGGTATTCATGGATACCGGTGGCTATTTAAATATGTGTGGACAT  520
 G  A  F  L  F  D  P  I  E  E  G  A  D  L  G  M  V  F  M  D  T  G  G  Y  L  N  M  C  G  H  162
AACTCAATTGCAGCGGTTACGGCGGCAGTTGAAACGGGAATTGTGAGCGTGCCGGCGAAGGCAACAAATGTTCCGGTTGTCCTGGACACA  610
 N  S  I  A  A  V  T  A  A  V  E  T  G  I  V  S  V  P  A  K  A  T  N  V  P  V  V  L  D  T  192
CCTGCGGGGTTGGTGCGCGGTACGGCACACCTTCAGAGTGGTACTGAGAGTGAGGTGTCAAATGCGAGTATTATCAATGTACCCTCATTT  700
 P  A  G  L  V  R  G  T  A  H  L  Q  S  G  T  E  S  E  V  S  N  A  S  I  I  N  V  P  S  F  222
TTGTATCAGCAGGATGTGGTGGTTGTGTTGCCAAAGCCCTATGGTGAAGTACGGGTTGATATTGCATTTGGAGGCAATTTTTTCGCCATT  790
 L  Y  Q  Q  D  V  V  V  V  L  P  K  P  Y  G  E  V  R  V  D  I  A  F  G  G  N  F  F  A  I  252
GTTCCCGCGGAGCAGTTGGGAATTGATATCTCCGTTCAAAACCTCTCCAGGCTGCAGGAGGCAGGAGAACTTCTGCGTACTGAAATCAAT  880
 V  P  A  E  Q  L  G  I  D  I  S  V  Q  N  L  S  R  L  Q  E  A  G  E  L  L  R  T  E  I  N  282
```

*FIG. 5A*

```
CGCAGTGTGAAGGTTCAGCACCCTCAGCTGCCCCATATTAACACTGTGGACTGTGTTGAGATATACGGTCCGCCAACGAACCCGGAGGCA  970
 R  S  V  K  V  Q  H  P  Q  L  P  H  I  N  T  V  D  C  V  E  I  Y  G  P  P  T  N  P  E  A   312
AACTACAAGAACGTTGTGATATTTGGCAATCGCCAGGCGGATCGCTCTCCATGTGGGACAGGCACCAGCGCCAAGATGGCAACACTTTAT 1060
 N  Y  K  N  V  V  I  F  G  N  R  Q  A  D  R  S  P  C  G  T  G  T  S  A  K  M  A  T  L  Y   342
GCCAAAGGCCAGCTTCGCATCGGAGAGACTTTTGTGTACGAGAGCATACTCGGCTCACTCTTCCAGGGCAGGGTACTTGGGGAGGAGCGA 1150
 A  K  G  Q  L  R  I  G  E  T  F  V  Y  E  S  I  L  G  S  L  F  Q  G  R  V  L  G  E  E  R   372
ATACCGGGGGTGAAGGTGCCGGTGACCAAAGATGCCGAGGAAGGGATGCTCGTTGTAACGGCAGAAATTACTGGAAAGGCTTTTATCATG 1240
 I  P  G  V  K  V  P  V  T  K  D  A  E  E  G  M  L  V  V  T  A  E  I  T  G  K  A  F  I  M   402
GGTTTCAACACCATGCTGTTTGACCCAACGGATCCGTTTAAGAACGGATTCACATTAAAGCAGTAGATCTGGTAGAGCACAGAAACTATT 1330
 G  F  N  T  M  L  F  D  P  T  D  P  F  K  N  G  F  T  L  K  Q                             423
GGGGAACACGTGCGAACAGGTGCTGCTACGTGAAGGGTATTGAATGAATCGTTTTTTTTTATTTTTATTTTTTATTTTTATTAGTGCATT 1420

ATTATTAAATTTTTTTTTTGTTTTGGGGTTTCAACGGTACCGCGTTGGGAGCAGGGAAGCGATAGCGGCCGGACAATTTTTTGCTTTTAT 1510

TTTCATTTTCATCTTCCTACCCAACCCCCTTGGTTCCACCGGTCGCGGCGGGGTCTTGTGGGTGGAGGAGTCCTAAATCCCGCACCTCGG 1600

AGGAATAAACATATTTCAATTTCATATCTTGGAATCAAAAGGCAT                                              1651
```

POLYADENILATION SITE

OBS: UNDERLINED THE SEQUENCED PEPTIDES USED TO DEDUCE DEGENERATED PRIMERS FOR CLONING

NUCLEOTIDE SEQUENCE AND PEPTIDE SEQUENCE TcPA45

FIG. 5B

WESTERN BLOT

SOLUBLE FRACTION OF EPIMASTIGOTES EXTRACT (CYTOSOLIC) REVEALED WITH ANTIBODY DIRECTED TO rTcPA45

----------- DEMONSTRATES THE EXISTANCE OF AN INTRACYTOPLASMIC FORM OF TcPA45 IN THE PARASITE

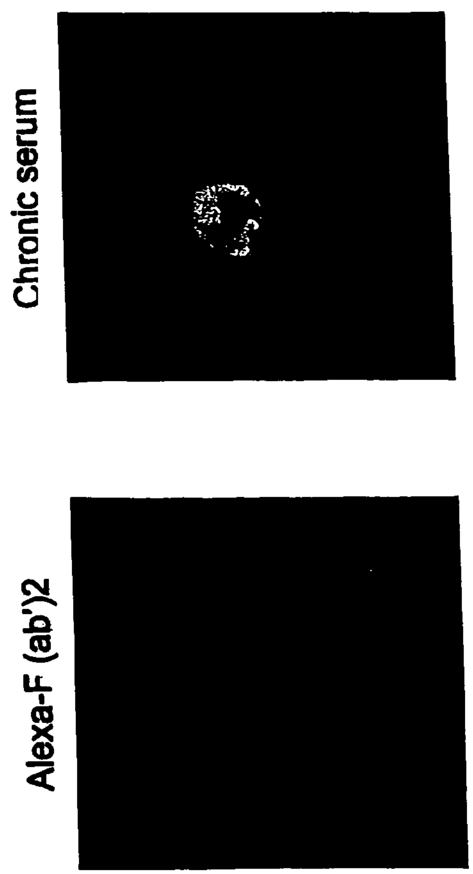
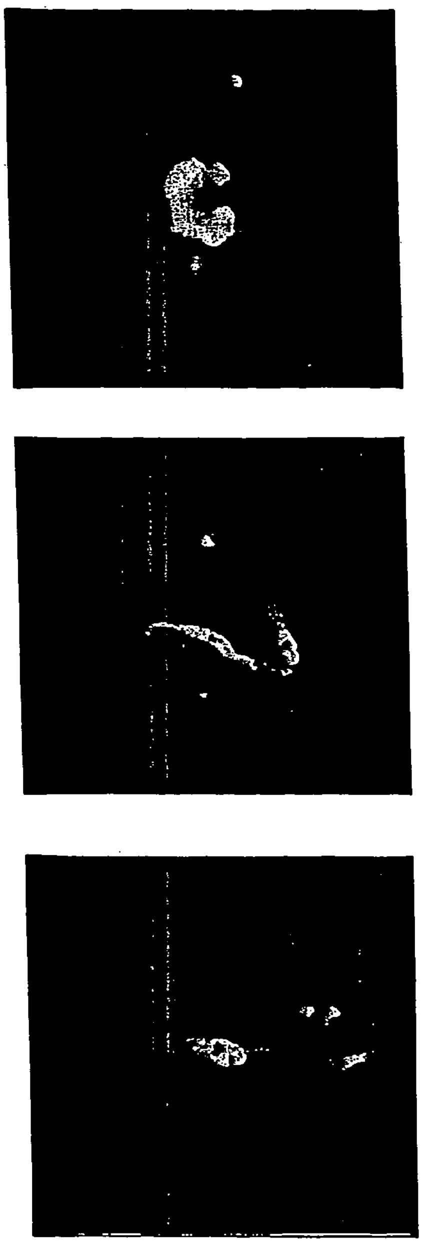
*FIG. 10A*

SEQ ID NO:2

Tc RTGQEKLLFDQKYKIIKGEKKEKKKNQRANRREHQQKREIMRFKKS 75
Tc FTCIDMHTEGEAARIVTSGLPHIPGSNMAEKKAYLQENMDYLRRGIMLEPRGHDDMFGAFLFDPIEEGADLGMVF 150
Tc MDTGGYLNMCGHNSIAAVTAAVETGIVSVPAKATNVPVVLDTPAGLVRGTAHLQSGTESEVSNASIINVPSFLYQ 225
Tc QDVVVVLPKPYGEVR*VDIAFGGNF*FAIVPAEQLGIDISVQNLSRLQEAGELLRTEINRSVKVQHPQLPHINTVDC 300
Tc VEIYGPPTNPEANYK*NVVIFGNR*QADR SPCGT GTSAKMATLYAKGQLRIGETFVYESILGSLFQGRV--LGEE 371
Tc RIPGVKVPVTKDAEEGMLVVTAEITGKAFIMGFNTMLFDPTDPFKNGFTLKQ* 423

*FIG. 15*

SEQ ID NO:4

```
Tc                                                                              MRFKKS   75
Tc  FTCIDMHTEGEAARIVTSGLPHIPGSNMAEKKAYLQENMDYLRRGIMLEPRGHDDMFGAFLFDPIEEGADLGMVF  150
Tc  MDTGGYLNMCGHNSIAAVTAAVETGIVSVPAKATNVPVVLDTPAGLVRGTAHLQSGTESEVSNASIINVPSFLYQ  225
Tc  QDVVVVLPKPYGEVRVDIAFGGNFFAIVPAEQLGIDISVQNLSRLQEAGELLRTEINRSVKVQHPQLPHINTVDC  300
Tc  VEIYGPPTNPEANYKNVVIFGNRQADR SPCGT GTSAKMATLYAKGQLRIGETFVYESILGSLFQGRV--LGEE  371
Tc  RIPGVKVPVTKDAEEGMLVVTAEITGKAFIMGFNTMLFDPTDPFKNGFTLKQ*                        423
```

*FIG. 16*

SEQ ID NO:7

POLYPYRIMIDINE RICH REGION

SPLICE LEADER ACCEPTOR SITES

SIGNAL PEPTIDE

```
CCTTTTTCTTTTTAAAAACAAAAAAAATTCCGGGGGGAATATGGAACAGGGTATATGCGTAAAAGTGTCTGTCCCAAACAAAAATTTTTT  90
                                                      M  R  K  S  V  C  P  K  Q  K  F  F   12
TTTTCCGCCTTCCCATTTTTTTTTTTTTTTGTGTGTTTCCCTTGATCTCTCGAACAGGGCAGGAAAAGCTTCTGTTTGACCAAAAATAT  180
 F  S  A  F  P  F  F  F  F  F  C  V  F  P  L  I  S  R  T  G  Q  E  K  L  L  F  D  Q  K  Y   42
AAAATTATTAAGGGCGAGAAAAAAGAAAAGAAAAAAAATCAACGAGCAAACAGGAGAGAACACCAACAAAAAAGGGAAATTATGCGATTT  270
 K  I  I  K  G  E  K  K  E  K  K  K  N  Q  R  A  N  R  R  E  K  Q  Q  K  R  E  I  M  R  F   72
AAGAAATCATTCACATGCATCGACATGCATACGGAAGGTGAAGCAGCACGGATTGTGACGAGTGGTTTGCCACACATTCCAGGTTCGAAT  360
 K  K  S  F  T  C  I  D  M  H  T  E  G  E  A  A  R  I  V  T  S  G  L  P  H  I  P  G  S  N  102
ATGGCGGAGAAGAAAGCATACCTGCAGGAAAACATGGATTATTTGAGGCGTGGCATAATGCTGGAACCACGTGGTCATGATGATATGTTT  430
 M  A  E  K  K  A  Y  L  Q  E  N  M  D  Y  L  R  R  G  I  M  L  E  P  R  G  K  D  D  M  F  132
GGAGCCTTTTTATTTGACCCTATTGAAGAAGGCGCTGACTTGGGCATGGTATTCATGGATACCGGTGGCTATTTAAATATGTGTGGACAT  520
 G  A  F  L  F  D  P  I  E  E  G  A  D  L  G  M  V  F  M  D  T  G  G  Y  L  N  M  C  G  H  162
AACTCAATTGCAGCGGTTACGGCGGCAGTTGAAACGGGAATTGTGAGCGTGCCGGCGAAGGCAACAAATGTTCCGGTTGTCCTGGACACA  610
 N  S  I  A  A  V  T  A  A  V  E  T  G  I  V  S  V  P  A  K  A  T  N  V  P  V  V  L  D  T  192
CCTGCGGGGTTGGTGCGCGGTACGGCACACCTTCAGAGTGGTACTGAGAGTGAGGTGTCAAATGCGAGTATTATCAATGTACCCTCATTT  700
 P  A  G  L  V  R  G  T  A  R  L  Q  S  G  T  E  S  E  V  S  N  A  S  I  I  N  V  P  S  F  222
TTGTATCAGCAGGATGTGGTGGTTGTGTTGCCAAAGCCCTATGGTGAAGTACGGGTTGATATTGCATTTGGAGGCAATTTTTTCGCCATT  790
 L  Y  Q  Q  D  V  V  V  V  L  P  K  P  Y  G  E  V  R  V  D  I  A  F  G  G  N  F  F  A  I  252
```

FIG. 17A

```
GTTCCCGCGGAGCAGTTGGGAATTGATATCTCCGTTCAAAACCTCTCCAGGCTGCAGGAGGCAGGAGAACTTCTGCGTACTGAAATCAAT  880
 V  P  A  E  Q  L  G  I  D  I  S  V  Q  N  L  S  R  L  Q  E  A  G  E  L  L  R  T  E  I  N   282
CGCAGTGTGAAGGTTCAGCACCCTCAGCTGCCCCATATTAACACTGTGGACTGTGTTGAGATATACGGTCCGCCAACGAACCCGGAGGCA  970
 R  S  V  K  V  Q  H  P  Q  L  P  H  I  N  T  V  D  C  V  E  I  Y  G  P  P  T  N  P  E  A   312
AACTACAAGAACGTTGTGATATTTGGCAATCGCCAGGCGGATCGCTCTCCATGTGGGACAGGCACCAGCGCCAAGATGGCAACACTTTAT 1060
 N  Y  K  N  V  V  I  F  G  N  R  Q  A  D  R  S  P  C  G  T  G  T  S  A  K  M  A  T  L  Y   342
GCCAAAGGCCAGCTTCGCATCGGAGAGACTTTTGTGTACGAGAGCATACTCGGCTCACTCTTCCAGGGCAGGGTACTTGGGGAGGAGCGA 1150
 A  K  G  Q  L  R  I  G  E  T  F  V  Y  E  S  I  L  G  S  L  F  Q  G  R  V  L  G  E  E  R   372
ATACCGGGGGTGAAGGTGCCGGTGACCAAAGATGCCGAGGAAGGGATGCTCGTTGTAACGGCAGAAATTACTGGAAAGGCTTTTATCATG 1240
 I  P  G  V  K  V  P  V  T  K  D  A  E  E  G  M  L  V  V  T  A  E  I  T  G  K  A  F  I  M   402
GGTTTCAACACCATGCTGTTTGACCCAACGGATCCGTTTAAGAACGGATTCACATTAAAGCAGTAGATCTGGTAGAGCACAGAAACTATT 1330
 G  F  N  T  M  L  F  D  P  T  D  P  F  K  N  G  F  T  L  K  Q  *                          423
GGGGAACACGTGCGAACAGGTGCTGCTACGTGAAGGGTATTGAATGAATCGTTTTTTTTATTTTTATTTTTTATTTTTATTAGTGCATT 1420

ATTATTAAATTTTTTTTTGTTTTGGGGTTTCAACGGTACCGCGTTGGGAGCAGGGAAGCGATAGCGGCCGGACAATTTTTTGCTTTTAT 1510

TTTCATTTTCATCTTCCTACCCAACCCCCTTGGTTCCACCGGTCGCGGCGGGGTCTTGTGGGTGGAGGAGTCCTAAATCCCGCACCTCGG 1600

AGGAATAAACATATTTCAATTTCATATCTTGGAATCAAAAGGCAT                                             1651
```

POLYADENILATION SITE

Obs: UNDERLINED THE SEQUENCED PEPTIDES USED TO DEDUCE DEGENERATED PRIMERS FOR CLONING (b) NUCLEOTIDE SEQUENCE AND PEPTIDE SEQUENCE TcPA45

FIG. 17B

SEQ ID NO:8

```
                                                            ATGCGTAAAAGTGTCTGTCCCAAACAAAAATTTTTT  90
                                                             M  R  K  S  V  C  P  K  Q  K  F  F  12
TTTTCCGCCTTCCCATTTTTTTTTTTTTTTGTGTGTTTCCCTTGATCTCTCGAACAGGGCAGGAAAAGCTTCTGTTTGACCAAAAATAT 180
 F  S  A  F  P  F  F  F  F  F  C  V  F  P  L  I  S  R  T  G  Q  E  K  L  L  F  D  Q  K  Y  42
AAAATTATTAAGGGCGAGAAAAAAGAAAAGAAAAAAAAATCAACGAGCAAACAGGAGAGAACACCAACAAAAAAGGGAAATTATGCGATTT 270
 K  I  I  K  G  E  K  K  E  K  K  K  N  Q  R  A  N  R  R  E  H  Q  Q  K  R  E  I  M  R  F  72
AAGAAATCATTCACATGCATCGACATGCATACGGAAGGTGAAGCAGCACGGATTGTGACGAGTGGTTTGCCACACATTCCAGGTTCGAAT 360
 K  K  S  F  T  C  I  D  M  H  T  E  G  E  A  A  R  I  V  T  S  G  L  P  H  I  P  G  S  N 102
ATGGCGGAGAAGAAAGCATACCTGCAGGAAAACATGGATTATTTGAGGCGTGGCATAATGCTGGAACCACGTGGTCATGATGATATGTTT 430
 M  A  E  K  K  A  Y  L  Q  E  N  M  D  Y  L  R  R  G  I  M  L  E  P  R  G  H  D  D  M  F 132
GGAGCCTTTTTATTTGACCCTATTGAAGAAGGCGCTGACTTGGGCATGGTATTCATGGATACCGGTGGCTATTTAAATATGTGTGGACAT 520
 G  A  F  L  F  D  P  I  E  E  G  A  D  L  G  M  V  F  M  D  T  G  G  Y  L  N  M  C  G  H 162
AACTCAATTGCAGCGGTTACGGCGGCAGTTGAAACGGGAATTGTGAGCGTGCCGGCGAAGGCAACAAATGTTCCGGTTGTCCTGGACACA 610
 N  S  I  A  A  V  T  A  A  V  E  T  G  I  V  S  V  P  A  K  A  T  N  V  P  V  V  L  D  T 192
CCTGCGGGGTTGGTGCGCGGTACGGCACACCTTCAGAGTGGTACTGAGAGTGAGGTGTCAAATGCGAGTATTATCAATGTACCCTCATTT 700
 P  A  G  L  V  R  G  T  A  H  L  Q  S  G  T  E  S  E  V  S  N  A  S  I  I  N  V  P  S  F 222
TTGTATCAGCAGGATGTGGTGGTTGTGTTGCCAAAGCCCTATGGTGAAGTACGGGTTGATATTGCATTTGGAGGCAATTTTTTCGCCATT 790
 L  Y  Q  Q  D  V  V  V  V  L  P  K  P  Y  G  E  V  R  V  D  I  A  F  G  G  N  F  F  A  I 252
GTTCCCGCGGAGCAGTTGGGAATTGATATCTCCGTTCAAAACCTCTCCAGGCTGCAGGAGGCAGGAGAACTTCTGCGTACTGAAATCAAT 880
 V  P  A  E  Q  L  G  I  D  I  S  V  Q  N  L  S  R  L  Q  E  A  G  E  L  L  R  T  E  I  N 282
CGCAGTGTGAAGGTTCAGCACCCTCAGCTGCCCCATATTAACACTGTGGACTGTGTTGAGATATACGGTCCGCCAACGAACCCGGAGGCA 970
 R  S  V  K  V  Q  H  P  Q  L  P  H  I  N  T  V  D  C  V  E  I  Y  G  P  P  T  N  P  E  A 312
```

FIG. 18A

```
AACTACAAGAACGTTGTGATATTTGGCAATCGCCAGGCGGATCGCTCTCCATGTGGGACAGGCACCAGCGCCAAGATGGCAACACTTTAT 1060
 N  Y  K  N  V  V  I  F  G  N  R  Q  A  D  R  S  P  C  G  T  G  T  S  A  K  M  A  T  L  Y   342
GCCAAAGGCCAGCTTCGCATCGGAGAGACTTTTGTGTACGAGAGCATACTCGGCTCACTCTTCCAGGGCAGGGTACTTGGGGAGGAGCGA 1150
 A  K  G  Q  L  R  I  G  E  T  F  V  Y  E  S  I  L  G  S  L  F  Q  G  R  V  L  G  E  E  R   372
ATACCGGGGGTGAAGGTGCCGGTGACCAAAGATGCCGAGGAAGGGATGCTCGTTGTAACGGCAGAAATTACTGGAAAGGCTTTTATCATG 1240
 I  P  G  V  K  V  P  V  T  K  D  A  E  E  G  M  L  V  V  T  A  E  I  T  G  K  A  F  I  M   402
GGTTTCAACACCATGCTGTTTGACCCAACGGATCCGTTTAAGAACGGATTCACATTAAAGCAGTAGATCTGGTAGAGCACAGAAACTATT 1330
 G  F  N  T  M  L  F  D  P  T  D  P  F  K  N  G  F  T  L  K  Q  *                           423
GGGGAACACGTGCGAACAGGTGCTGCTACGTGAAGGGTATTGAATGAATCGTTTTTTTTTATTTTTATTTTTTATTTTTATTAGTGCATT 1420

ATTATTAAATTTTTTTTTTGTTTTGGGGTTTCAACGGTACCGCGTTGGGAGCAGGGAAGCGATAGCGGCCGGACAATTTTTTGCTTTTAT 1510

TTTCATTTTCATCTTCCTACCCAACCCCCTTGGTTCCACCGGTCGCGGCGGGGTCTTGTGGGTGGAGGAGTCCTAAATCCCGCACCTCGG 1600

AGGAATAAACATATTTCAATTTCATATCTTGGAATCAAAAGGCAT                                              1651
```

POLYADENILATION SITE

Obs: UNDERLINED THE SEQUENCED PEPTIDES USED TO DEDUCE DEGENERATED PRIMERS FOR CLONING

NUCLEOTIDE SEQUENCE AND PEPTIDE SEQUENCE TcPA45

*FIG. 18B*

SEQ ID NO:9

```
CGAACAGGGCAGGAAAAGCTTCTGTTTGACCAAAAATAT 270
 R  T  G  Q  E  K  L  L  F  D  Q  K  Y 72
AAAATTATTAAGGGCGAGAAAAAAGAAAAGAAAAAAAATCAACGAGCAAACAGGAGAGAACACCAACAAAAAAGGGAAATTATGCGATTT 360
 K  I  I  K  G  E  K  K  E  K  K  K  N  Q  R  A  N  R  R  E  H  Q  Q  K  R  E  I  M  R  F 102
AAGAAATCATTCACATGCATCGACATGCATACGGAAGGTGAAGCAGCACGGATTGTGACGAGTGGTTTGCCACACATTCCAGGTTCGAAT 430
 K  K  S  F  T  C  I  D  M  H  T  E  G  E  A  A  R  I  V  T  S  G  L  P  H  I  P  G  S  N 132
ATGGCGGAGAAGAAAGCATACCTGCAGGAAAACATGGATTATTTGAGGCGTGGCATAATGCTGGAACCACGTGGTCATGATGATATGTTT 520
 M  A  E  K  K  A  Y  L  Q  E  N  M  D  Y  L  R  R  G  I  M  L  E  P  R  G  H  D  D  M  F 162
GGAGCCTTTTTATTTGACCCTATTGAAGAAGGCGCTGACTTGGGCATGGTATTCATGGATACCGGTGGCTATTTAAATATGTGTGGACAT 610
 G  A  F  L  F  D  P  I  E  E  G  A  D  L  G  M  V  F  M  D  T  G  G  Y  L  N  M  C  G  H 192
AACTCAATTGCAGCGGTTACGGCGGCAGTTGAAACGGGAATTGTGAGCGTGCCGGCGAAGGCAACAAATGTTCCGGTTGTCCTGGACACA 700
 N  S  I  A  A  V  T  A  A  V  E  T  G  I  V  S  V  P  A  K  A  T  N  V  P  V  V  L  D  T 222
CCTGCGGGGTTGGTGCGCGGTACGGCACACCTTCAGAGTGGTACTGAGAGTGAGGTGTCAAATGCGAGTATTATCAATGTACCCTCATTT 790
 P  A  G  L  V  R  G  T  A  H  L  Q  S  G  T  E  S  E  V  S  N  A  S  I  I  N  V  P  S  F 252
TTGTATCAGCAGGATGTGGTGGTTGTGTTGCCAAAGCCCTATGGTGAAGTACGGGTTGATATTGCATTTGGAGGCAATTTTTTCGCCATT 880
 L  Y  Q  Q  D  V  V  V  V  L  P  K  P  Y  G  E  V  R  V  D  I  A  F  G  G  N  F  F  A  I 282
GTTCCCGCGGAGCAGTTGGGAATTGATATCTCCGTTCAAAACCTCTCCAGGCTGCAGGAGGCAGGAGAACTTCTGCGTACTGAAATCAAT 970
 V  P  A  E  Q  L  G  I  D  I  S  V  Q  N  L  S  R  L  Q  E  A  G  E  L  L  R  T  E  I  N 312
CGCAGTGTGAAGGTTCAGCACCCTCAGCTGCCCCATATTAACACTGTGGACTGTGTTGAGATATACGGTCCGCCAACGAACCCGGAGGCA 1060
 R  S  V  K  V  Q  H  P  Q  L  P  H  I  N  T  V  D  C  V  E  I  Y  G  P  P  T  N  P  E  A 342
AACTACAAGAACGTTGTGATATTTGGCAATCGCCAGGCGGATCGCTCTCCATGTGGGACAGGCACCAGCGCCAAGATGGCAACACTTTAT 1150
 N  Y  K  N  V  V  I  F  G  N  R  Q  A  D  R  S  P  C  G  T  G  T  S  A  K  M  A  T  L  Y 372
```

*FIG. 19A*

```
GCCAAAGGCCAGCTTCGCATCGGAGAGACTTTTGTGTACGAGAGCATACTCGGCTCACTCTTCCAGGGCAGGGTACTTGGGGAGGAGCGA 1240
 A  K  G  Q  L  R  I  G  E  T  F  V  Y  E  S  I  L  G  S  L  F  Q  G  R  V  L  G  E  E  R  402
ATACCGGGGGTGAAGGTGCCGGTGACCAAAGATGCCGAGGAAGGGATGCTCGTTGTAACGGCAGAAATTACTGGAAAGGCTTTTATCATG 1330
 I  P  G  V  K  V  P  V  T  K  D  A  E  E  G  M  L  V  V  T  A  E  I  T  G  K  A  F  I  M  423
GGTTTCAACACCATGCTGTTTGACCCAACGGATCCGTTTAAGAACGGATTCACATTAAAGCAGTAGATCTGGTAGAGCACAGAAACTATT 1420
 G  F  N  T  M  L  F  D  P  T  D  P  F  K  N  G  F  T  L  K  Q  *
GGGGAACACGTGCGAACAGGTGCTGCTACGTGAAGGGTATTGAATGAATCGTTTTTTTTATTTTTATTTTTATTTTTATTAGTGCATT 1510

ATTATTAAATTTTTTTTTGTTTTGGGGTTTCAACGGTACCGCGTTGGGAGCAGGGAAGCGATAGCGGCCGGACAATTTTTTGCTTTTAT 1600

TTTCATTTTCATCTTCCTACCCAACCCCCTTGGTTCCACCGGTCGCGGCGGGGTCTTGTGGGTGGAGGAGTCCTAAATCCCGCACCTCGG 1651

AGGAATAAACATATTTCAATTTCATATCTTGGAATCAAAAGGCAT
```

POLYADENILATION SITE

Obs: UNDERLINED THE SEQUENCED PEPTIDES USED TO DEDUCE DEGENERATED PRIMERS FOR CLONING

NUCLEOTIDE SEQUENCE AND PEPTIDE SEQUENCE TcPA45

*FIG. 19B*

SEQ ID NO:10

SIGNAL PEPTIDE

ATGCGTAAAAGTGTCTGTCCCAAACAAAAATTTTTT

TTTTCCGCCTTCCCATTTTTTTTTTTTTTTGTGTGTTTCCCTTGATCTCT

NUCLEOTIDE SEQUENCE OF SIGNAL SEQUENCE TcPA45

*FIG. 20*

SEQ ID NO:11

```
                                                                                  ATGCGATTT  360
                                                                                    M  R  F  102
AAGAAATCATTCACATGCATCGACATGCATACGGAAGGTGAAGCAGCACGGATTGTGACGAGTGGTTTGCCACACATTCCAGGTTCGAAT  430
 K  K  S  F  T  C  I  D  M  H  T  E  G  E  A  A  R  I  V  T  S  G  L  P  H  I  P  G  S  N  132
ATGGCGGAGAAGAAAGCATACCTGCAGGAAAACATGGATTATTTGAGGCGTGGCATAATGCTGGAACCACGTGGTCATGATGATATGTTT  520
 M  A  E  K  K  A  Y  L  Q  E  N  M  D  Y  L  R  R  G  I  M  L  E  P  R  G  H  D  D  M  F  162
GGAGCCTTTTTATTTGACCCTATTGAAGAAGGCGCTGACTTGGGCATGGTATTCATGGATACCGGTGGCTATTTAAATATGTGTGGACAT  610
 G  A  F  L  F  D  P  I  E  E  G  A  D  L  G  M  V  F  M  D  T  G  G  Y  L  N  M  C  G  H  192
AACTCAATTGCAGCGGTTACGGCGGCAGTTGAAACGGGAATTGTGAGCGTGCCGGCGAAGGCAACAAATGTTCCGGTTGTCCTGGACACA  700
 N  S  I  A  A  V  T  A  A  V  E  T  G  I  V  S  V  P  A  K  A  T  N  V  P  V  V  L  D  T  222
CCTGCGGGGTTGGTGCGCGGTACGGCACACCTTCAGAGTGGTACTGAGAGTGAGGTGTCAAATGCGAGTATTATCAATGTACCCTCATTT  790
 P  A  G  L  V  R  G  T  A  H  L  Q  S  G  T  E  S  E  V  S  N  A  S  I  I  N  V  P  S  F  252
TTGTATCAGCAGGATGTGGTGGTTGTGTTGCCAAAGCCCTATGGTGAAGTACGGGTTGATATTGCATTTGGAGGCAATTTTTTCGCCATT  880
 L  Y  Q  Q  D  V  V  V  V  L  P  K  P  Y  G  E  V  R  V  D  I  A  F  G  G  N  F  F  A  I  282
GTTCCCGCGGAGCAGTTGGGAATTGATATCTCCGTTCAAAACCTCTCCAGGCTGCAGGAGGCAGGAGAACTTCTGCGTACTGAAATCAAT  970
 V  P  A  E  Q  L  G  I  D  I  S  V  Q  N  L  S  R  L  Q  E  A  G  E  L  L  R  T  E  I  N  312
CGCAGTGTGAAGGTTCAGCACCCTCAGCTGCCCCATATTAACACTGTGGACTGTGTTGAGATATACGGTCCGCCAACGAACCCGGAGGCA 1060
 R  S  V  K  V  Q  H  P  Q  L  P  H  I  N  T  V  D  C  V  E  I  Y  G  P  P  T  N  P  E  A  342
AACTACAAGAACGTTGTGATATTTGGCAATCGCCAGGCGGATCGCTCTCCATGTGGGACAGGCACCAGCGCCAAGATGGCAACACTTTAT 1150
 N  Y  K  N  V  V  I  F  G  N  R  Q  A  D  R  S  P  C  G  T  G  T  S  A  K  M  A  T  L  Y  372
GCCAAAGGCCAGCTTCGCATCGGAGAGACTTTTGTGTACGAGAGCATACTCGGCTCACTCTTCCAGGGCAGGGTACTTGGGGAGGAGCGA 1240
 A  K  G  Q  L  R  I  G  E  T  F  V  Y  E  S  I  L  G  S  L  F  Q  G  R  V  L  G  E  E  R  402
```

FIG. 21A

```
ATACCGGGGGTGAAGGTGCCGGTGACCAAAGATGCCGAGGAAGGGATGCTCGTTGTAACGGCAGAAATTACTGGAAAGGCTTTTATCATG 1330
 I  P  G  V  K  V  P  V  T  K  D  A  E  E  G  M  L  V  V  T  A  E  I  T  G  K  A  F  I  M   423
GGTTTCAACACCATGCTGTTTGACCCAACGGATCCGTTTAAGAACGGATTCACATTAAAGCAGTAGATCTGGTAGAGCACAGAAACTATT 1420
 G  F  N  T  M  L  F  D  P  T  D  P  F  K  N  G  F  T  L  K  Q  *
GGGGAACACGTGCGAACAGGTGCTGCTACGTGAAGGGTATTGAATGAATCGTTTTTTTTTATTTTTATTTTTTATTTTTATTAGTGCATT 1510

ATTATTAAATTTTTTTTTTGTTTTGGGGTTTCAACGGTACCGCGTTGGGAGCAGGGAAGCGATAGCGGCCGGACAATTTTTTGCTTTTAT 1600

TTTCATTTTCATCTTCCTACCCAACCCCCTTGGTTCCACCGGTCGCGGCGGGGTCTTGTGGGTGGAGGAGTCCTAAATCCCGCACCTCGG 1651

AGGAATAAACATATTTCAATTTCATATCTTGGAATCAAAAGGCAT
```

FIG. 21B

SEQUENCE LISTING

```
<160> NUMBER OF SEQ ID NOS: 27

<210> SEQ ID NO 1
<211> LENGTH: 418
<212> TYPE: PRT
<213> ORGANISM: Trypanosoma cruzi

<400> SEQUENCE: 1

Met Arg Lys Ser Val Cys Pro Lys Gln Lys Phe Phe Phe Ser Ala Phe
1               5                   10                  15

Pro Phe Phe Phe Phe Phe Cys Val Phe Pro Leu Ile Ser Arg Thr Gly
            20                  25                  30

Gln Glu Lys Leu Leu Phe Asp Gln Lys Tyr Lys Ile Ile Lys Gly Glu
        35                  40                  45

Lys Lys Glu Lys Lys Lys Asn Gln Arg Ala Asn Arg Arg Glu His Gln
    50                  55                  60

Gln Lys Arg Glu Ile Met Arg Phe Lys Lys Ser Phe Thr Cys Ile Asp
65                  70                  75                  80

Met His Thr Glu Gly Glu Ala Ala Arg Ile Val Thr Ser Gly Leu Pro
                85                  90                  95

His Ile Pro Gly Ser Asn Met Ala Glu Lys Lys Ala Tyr Leu Gln Glu
            100                 105                 110
```

```
Asn Met Asp Tyr Leu Arg Arg Gly Ile Met Leu Glu Pro Arg Gly His
        115                 120                 125

Asp Asp Met Phe Gly Ala Phe Leu Phe Asp Pro Ile Glu Glu Gly Ala
    130                 135                 140

Asp Leu Gly Met Val Phe Met Asp Thr Gly Gly Tyr Leu Asn Met Cys
145                 150                 155                 160

Gly His Asn Ser Ile Ala Ala Val Thr Ala Ala Val Glu Thr Gly Ile
                165                 170                 175

Val Ser Val Pro Ala Lys Ala Thr Asn Val Pro Val Val Leu Asp Thr
            180                 185                 190

Pro Ala Gly Leu Val Arg Gly Thr Ala His Leu Gln Ser Gly Thr Glu
        195                 200                 205

Ser Glu Val Ser Asn Ala Ser Ile Ile Asn Val Pro Ser Phe Leu Tyr
    210                 215                 220

Gln Gln Asp Val Val Val Val Leu Pro Lys Pro Tyr Gly Glu Val Arg
225                 230                 235                 240

Val Asp Ile Ala Phe Gly Gly Asn Phe Phe Ala Ile Val Pro Ala Glu
                245                 250                 255

Gln Leu Gly Ile Asp Ile Ser Val Gln Asn Leu Ser Arg Leu Gln Glu
            260                 265                 270

Ala Gly Glu Leu Leu Arg Thr Glu Ile Asn Arg Ser Val Lys Val Gln
        275                 280                 285

His Pro Gln Leu Pro His Ile Asn Thr Val Asp Cys Val Glu Ile Tyr
    290                 295                 300

Gly Pro Pro Thr Asn Pro Glu Ala Asn Tyr Lys Asn Val Val Ile Phe
305                 310                 315                 320

Gly Asn Arg Gln Ala Asp Arg Gly Thr Ser Ala Lys Met Ala Thr Leu
                325                 330                 335

Tyr Ala Lys Gly Gln Leu Arg Ile Gly Glu Thr Phe Val Tyr Glu Ser
            340                 345                 350

Ile Leu Gly Ser Leu Phe Gln Gly Arg Val Leu Gly Glu Glu Arg Ile
        355                 360                 365

Pro Gly Val Lys Val Pro Val Thr Lys Asp Ala Glu Glu Gly Met Leu
    370                 375                 380

Val Val Thr Ala Glu Ile Thr Gly Lys Ala Phe Ile Met Gly Phe Asn
385                 390                 395                 400

Thr Met Leu Phe Asp Pro Thr Asp Pro Phe Lys Asn Gly Phe Thr Leu
                405                 410                 415

Lys Gln


<210> SEQ ID NO 2
<211> LENGTH: 389
<212> TYPE: PRT
<213> ORGANISM: Trypanosoma cruzi

<400> SEQUENCE: 2

Arg Thr Gly Gln Glu Lys Leu Leu Phe Asp Gln Lys Tyr Lys Ile Ile
  1               5                  10                  15

Lys Gly Glu Lys Lys Glu Lys Lys Lys Asn Gln Arg Ala Asn Arg Arg
            20                  25                  30

Glu His Gln Gln Lys Arg Glu Ile Met Arg Phe Lys Lys Ser Phe Thr
        35                  40                  45

Cys Ile Asp Met His Thr Glu Gly Glu Ala Ala Arg Ile Val Thr Ser
    50                  55                  60
```

```
Gly Leu Pro His Ile Pro Gly Ser Asn Met Ala Glu Lys Lys Ala Tyr
 65                  70                  75                  80

Leu Gln Glu Asn Met Asp Tyr Leu Arg Arg Gly Ile Met Leu Glu Pro
                 85                  90                  95

Arg Gly His Asp Asp Met Phe Gly Ala Phe Leu Phe Asp Pro Ile Glu
            100                 105                 110

Glu Gly Ala Asp Leu Gly Met Val Phe Met Asp Thr Gly Gly Tyr Leu
        115                 120                 125

Asn Met Cys Gly His Asn Ser Ile Ala Ala Val Thr Ala Ala Val Glu
    130                 135                 140

Thr Gly Ile Val Ser Val Pro Ala Lys Ala Thr Asn Val Pro Val Val
145                 150                 155                 160

Leu Asp Thr Pro Ala Gly Leu Val Arg Gly Thr Ala His Leu Gln Ser
                165                 170                 175

Gly Thr Glu Ser Glu Val Ser Asn Ala Ser Ile Ile Asn Val Pro Ser
            180                 185                 190

Phe Leu Tyr Gln Gln Asp Val Val Val Val Leu Pro Lys Pro Tyr Gly
        195                 200                 205

Glu Val Arg Val Asp Ile Ala Phe Gly Gly Asn Phe Phe Ala Ile Val
    210                 215                 220

Pro Ala Glu Gln Leu Gly Ile Asp Ile Ser Val Gln Asn Leu Ser Arg
225                 230                 235                 240

Leu Gln Glu Ala Gly Glu Leu Leu Arg Thr Glu Ile Asn Arg Ser Val
                245                 250                 255

Lys Val Gln His Pro Gln Leu Pro His Ile Asn Thr Val Asp Cys Val
            260                 265                 270

Glu Ile Tyr Gly Pro Pro Thr Asn Pro Glu Ala Asn Tyr Lys Asn Val
        275                 280                 285

Val Ile Phe Gly Asn Arg Gln Ala Asp Arg Gly Thr Ser Ala Lys Met
    290                 295                 300

Ala Thr Leu Tyr Ala Lys Gly Gln Leu Arg Ile Gly Glu Thr Phe Val
305                 310                 315                 320

Tyr Glu Ser Ile Leu Gly Ser Leu Phe Gln Gly Arg Val Leu Gly Glu
                325                 330                 335

Glu Arg Ile Pro Gly Val Lys Val Pro Val Thr Lys Asp Ala Glu Glu
            340                 345                 350

Gly Met Leu Val Val Thr Ala Glu Ile Thr Gly Lys Ala Phe Ile Met
        355                 360                 365

Gly Phe Asn Thr Met Leu Phe Asp Pro Thr Asp Pro Phe Lys Asn Gly
    370                 375                 380

Phe Thr Leu Lys Gln
385


<210> SEQ ID NO 3
<211> LENGTH: 29
<212> TYPE: PRT
<213> ORGANISM: Trypanosoma cruzi

<400> SEQUENCE: 3

Met Arg Lys Ser Val Cys Pro Lys Gln Lys Phe Phe Phe Ser Ala Phe
  1               5                  10                  15

Pro Phe Phe Phe Phe Phe Cys Val Phe Pro Leu Ile Ser
            20                  25
```

```
<210> SEQ ID NO 4
<211> LENGTH: 354
<212> TYPE: PRT
<213> ORGANISM: Trypanosoma cruzi

<400> SEQUENCE: 4

Met Arg Phe Lys Lys Ser Phe Thr Cys Ile Asp Met His Thr Glu Gly
  1               5                  10                  15

Glu Ala Ala Arg Ile Val Thr Ser Gly Leu Pro His Ile Pro Gly Ser
             20                  25                  30

Asn Met Ala Glu Lys Lys Ala Tyr Leu Gln Glu Asn Met Asp Tyr Leu
         35                  40                  45

Arg Arg Gly Ile Met Leu Glu Pro Arg Gly His Asp Asp Met Phe Gly
     50                  55                  60

Ala Phe Leu Phe Asp Pro Ile Glu Glu Gly Ala Asp Leu Gly Met Val
 65                  70                  75                  80

Phe Met Asp Thr Gly Gly Tyr Leu Asn Met Cys Gly His Asn Ser Ile
                 85                  90                  95

Ala Ala Val Thr Ala Ala Val Glu Thr Gly Ile Val Ser Val Pro Ala
            100                 105                 110

Lys Ala Thr Asn Val Pro Val Val Leu Asp Thr Pro Ala Gly Leu Val
        115                 120                 125

Arg Gly Thr Ala His Leu Gln Ser Gly Thr Glu Ser Glu Val Ser Asn
    130                 135                 140

Ala Ser Ile Ile Asn Val Pro Ser Phe Leu Tyr Gln Gln Asp Val Val
145                 150                 155                 160

Val Val Leu Pro Lys Pro Tyr Gly Glu Val Arg Val Asp Ile Ala Phe
                165                 170                 175

Gly Gly Asn Phe Phe Ala Ile Val Pro Ala Glu Gln Leu Gly Ile Asp
            180                 185                 190

Ile Ser Val Gln Asn Leu Ser Arg Leu Gln Glu Ala Gly Glu Leu Leu
        195                 200                 205

Arg Thr Glu Ile Asn Arg Ser Val Lys Val Gln His Pro Gln Leu Pro
    210                 215                 220

His Ile Asn Thr Val Asp Cys Val Glu Ile Tyr Gly Pro Pro Thr Asn
225                 230                 235                 240

Pro Glu Ala Asn Tyr Lys Asn Val Val Ile Phe Gly Asn Arg Gln Ala
                245                 250                 255

Asp Arg Ser Pro Cys Gly Thr Gly Thr Ser Ala Lys Met Ala Thr Leu
            260                 265                 270

Tyr Ala Lys Gly Gln Leu Arg Ile Gly Glu Thr Phe Val Tyr Glu Ser
        275                 280                 285

Ile Leu Gly Ser Leu Phe Gln Gly Arg Val Leu Gly Glu Glu Arg Ile
    290                 295                 300

Pro Gly Val Lys Val Pro Val Thr Lys Asp Ala Glu Glu Gly Met Leu
305                 310                 315                 320

Val Val Thr Ala Glu Ile Thr Gly Lys Ala Phe Ile Met Gly Phe Asn
                325                 330                 335

Thr Met Leu Phe Asp Pro Thr Asp Pro Phe Lys Asn Gly Phe Thr Leu
            340                 345                 350

Lys Gln


<210> SEQ ID NO 5
<211> LENGTH: 330
<212> TYPE: PRT
<213> ORGANISM: Clostridium sticklandii
```

<400> SEQUENCE: 5

```
Met Lys Phe Ser Lys Gly Ile His Ala Ile Asp Ser His Thr Met Gly
  1               5                  10                  15

Glu Pro Thr Arg Ile Val Val Gly Gly Ile Pro Gln Ile Asn Gly Glu
             20                  25                  30

Thr Met Ala Asp Lys Lys Lys Tyr Leu Glu Asp Asn Leu Asp Tyr Val
         35                  40                  45

Arg Thr Ala Leu Met His Glu Pro Arg Gly His Asn Asp Met Phe Gly
     50                  55                  60

Ser Ile Ile Thr Ser Ser Asn Asn Lys Glu Ala Asp Phe Gly Ile Ile
 65                  70                  75                  80

Phe Met Asp Gly Gly Gly Tyr Leu Asn Met Cys Gly His Gly Ser Ile
                 85                  90                  95

Gly Ala Ala Thr Val Ala Val Glu Thr Gly Met Val Glu Met Val Glu
            100                 105                 110

Pro Val Thr Asn Ile Asn Met Glu Ala Pro Ala Gly Leu Ile Lys Ala
        115                 120                 125

Lys Val Met Val Glu Asn Glu Lys Val Lys Glu Val Ser Ile Thr Asn
    130                 135                 140

Val Pro Ser Phe Leu Tyr Met Glu Asp Ala Lys Leu Glu Val Pro Ser
145                 150                 155                 160

Leu Asn Lys Thr Ile Thr Phe Asp Ile Ser Phe Gly Gly Ser Phe Phe
                165                 170                 175

Ala Ile Ile His Ala Lys Glu Leu Gly Val Lys Val Glu Thr Ser Gln
            180                 185                 190

Val Asp Val Leu Lys Lys Leu Gly Ile Glu Ile Arg Asp Leu Ile Asn
        195                 200                 205

Glu Lys Ile Lys Val Gln His Pro Glu Leu Glu His Ile Lys Thr Val
    210                 215                 220

Asp Leu Val Glu Ile Tyr Asp Glu Pro Ser Asn Pro Glu Ala Thr Tyr
225                 230                 235                 240

Lys Asn Val Val Ile Phe Gly Gln Gly Gln Val Asp Arg Gly Thr Ser
                245                 250                 255

Ala Lys Leu Ala Thr Leu Tyr Lys Lys Gly His Leu Lys Ile Asp Glu
            260                 265                 270

Lys Glu Val Tyr Glu Ser Ile Thr Gly Thr Met Phe Lys Gly Arg Val
        275                 280                 285

Leu Glu Glu Thr Lys Val Gly Glu Phe Asp Ala Ile Ile Pro Glu Ile
    290                 295                 300

Thr Gly Gly Ala Tyr Ile Thr Gly Glu Asn His Glu Val Ile Asp Pro
305                 310                 315                 320

Glu Asp Pro Leu Lys Tyr Gly Phe Thr Val
                325                 330
```

<210> SEQ ID NO 6
<211> LENGTH: 314
<212> TYPE: PRT
<213> ORGANISM: Pseudomonas aeruginosa

<400> SEQUENCE: 6

```
Met Gln Arg Ile Arg Ile Ile Asp Ser His Thr Gly Gly Glu Pro Thr
  1               5                  10                  15

Arg Leu Val Ile Gly Gly Phe Pro Asp Leu Gly Gln Gly Asp Met Ala
             20                  25                  30
```

```
Glu Arg Arg Arg Leu Leu Gly Glu Arg His Asp Ala Trp Arg Ala Ala
        35                  40                  45

Cys Ile Leu Glu Pro Arg Gly Ser Asp Val Leu Val Gly Ala Leu Leu
    50                  55                  60

Cys Ala Pro Val Asp Pro Glu Ala Cys Ala Gly Val Ile Phe Phe Asn
65                  70                  75                  80

Asn Ser Gly Tyr Leu Gly Met Cys Gly His Gly Thr Ile Gly Leu Val
                85                  90                  95

Ala Ser Leu Ala His Leu Gly Arg Ile Gly Pro Gly Val His Arg Ile
            100                 105                 110

Glu Thr Pro Val Gly Glu Val Glu Ala Thr Leu His Glu Asp Gly Ser
        115                 120                 125

Val Ser Val Arg Asn Val Pro Ala Tyr Arg Tyr Arg Arg Gln Val Ser
    130                 135                 140

Val Glu Val Pro Gly Ile Gly Arg Val Ser Gly Asp Ile Ala Trp Gly
145                 150                 155                 160

Gly Asn Trp Phe Phe Leu Val Ala Gly His Gly Gln Arg Leu Ala Gly
                165                 170                 175

Asp Asn Leu Asp Ala Leu Thr Ala Tyr Thr Val Ala Val Gln Gln Ala
            180                 185                 190

Leu Asp Asp Gln Asp Ile Arg Gly Glu Asp Gly Gly Ala Ile Asp His
        195                 200                 205

Ile Glu Leu Phe Ala Asp Asp Pro His Ala Asp Ser Arg Asn Phe Val
    210                 215                 220

Leu Cys Pro Gly Lys Ala Tyr Asp Arg Ser Pro Cys Gly Thr Gly Thr
225                 230                 235                 240

Ser Ala Lys Leu Ala Cys Leu Ala Ala Asp Gly Lys Leu Leu Pro Gly
                245                 250                 255

Gln Pro Trp Arg Gln Ala Ser Val Ile Gly Ser Gln Phe Glu Gly Arg
            260                 265                 270

Tyr Glu Trp Leu Asp Gly Gln Pro Gly Gly Pro Ile Val Pro Thr Ile
        275                 280                 285

Arg Gly Arg Ala His Val Ser Ala Glu Ala Thr Leu Leu Leu Ala Asp
    290                 295                 300

Asp Asp Pro Phe Ala Trp Gly Ile Arg Arg
305                 310
```

<210> SEQ ID NO 7
<211> LENGTH: 1665
<212> TYPE: DNA
<213> ORGANISM: Trypanosoma cruzi

<400> SEQUENCE: 7

```
cctttttctt tttaaaaaca aaaaaaattc cggggggaat atggaacagg gtatatgcgt      60

aaaagtgtct gtcccaaaca aaaatttttt ttttccgcct tcccattttt ttttttttt     120

tgtgtgtttc ccttgatctc tcgaacaggg caggaaaagc ttctgtttga ccaaaaatat    180

aaaattatta agggcgagaa aaaagaaaag aaaaaaaatc aacgagcaaa caggagagaa    240

caccaacaaa aaagggaaat tatgcgattt aagaaatcat tcacatgcat cgacatgcat    300

acggaaggtg aagcagcacg gattgtgacg agtggtttgc cacacattcc aggttcgaat    360

atggcggaga agaaagcata cctgcaggaa aacatggatt atttgaggcg tggcataatg    420

ctggaaccac gtggtcatga tgatatgttt ggagcctttt tatttgaccc tattgaagaa    480

ggcgctgact tgggcatggt attcatggat accggtggct atttaaatat gtgtggacat    540
```

-continued

```
aactcaattg cagcggttac ggcggcagtt gaaacgggaa ttgtgagcgt gccggcgaag    600
gcaacaaatg ttccggttgt cctggacaca cctgcggggt tggtgcgcgg tacggcacac    660
cttcagagtg gtactgagag tgaggtgtca aatgcgagta ttatcaatgt accctcattt    720
ttgtatcagc aggatgtggt ggttgtgttg ccaaagccct atggtgaagt acgggttgat    780
attgcatttg gaggcaattt tttcgccatt gttcccgcgg agcagttggg aattgatatc    840
tccgttcaaa acctctccag gctgcaggag gcaggagaac ttctgcgtac tgaaatcaat    900
cgcagtgtga aggttcagca ccctcagctg ccccatatta acactgtgga ctgtgttgag    960
atatacggtc cgccaacgaa cccggaggca aactacaaga acgttgtgat atttggcaat   1020
cgccaggcgg atcgctctcc atgtgggaca ggcaccagcg ccaagatggc aacactttat   1080
gccaaaggcc agcttcgcat cggagagact tttgtgtacg agagcatact cggctcactc   1140
ttccagggca gggtacttgg ggaggagcga ataccggggg tgaaggtgcc ggtgaccaaa   1200
gatgccgagg aagggatgct cgttgtaacg gcagaaatta ctggaaaggc ttttatcatg   1260
ggtttcaaca ccatgctgtt tgacccaacg gatccgttta agaacggatt cacattaaag   1320
cagtagatct ggtagagcac agaaactatt ggggaacacg tgcgaacagg tgctgctacg   1380
tgaagggtat tgaatgaatc gttttttttt atttttattt tttattttta ttagtgcatt   1440
attattaaat tttttttttg ttttggggtt tcaacggtac cgcgttggga gcagggaagc   1500
gatagcggcc ggacaatttt ttgcttttat tttcattttc atcttcctac ccaacccccct  1560
tggttccacc ggtcgcggcg gggtcttgtg ggtggaggag tcctaaatcc cgcacctcgg   1620
aggaataaac atatttcaat ttcatatctt ggaatcaaaa ggcat                   1665
```

```
<210> SEQ ID NO 8
<211> LENGTH: 1575
<212> TYPE: DNA
<213> ORGANISM: Trypanosoma cruzi

<400> SEQUENCE: 8

ttttccgcct tcccattttt tttttttttt tgtgtgtttc ccttgatctc tcgaacaggg     60
caggaaaagc ttctgtttga ccaaaaatat aaaattatta agggcgagaa aaaagaaaag    120
aaaaaaaatc aacgagcaaa caggagagaa caccaacaaa aaagggaaat tatgcgattt    180
aagaaatcat tcacatgcat cgacatgcat acggaaggtg aagcagcacg gattgtgacg    240
agtggtttgc cacacattcc aggttcgaat atggcggaga agaaagcata cctgcaggaa    300
aacatggatt atttgaggcg tggcataatg ctggaaccac gtggtcatga tgatatgttt    360
ggagcctttt tatttgaccc tattgaagaa ggcgctgact tgggcatggt attcatggat    420
accggtggct atttaaatat gtgtggacat aactcaattg cagcggttac ggcggcagtt    480
gaaacgggaa ttgtgagcgt gccggcgaag gcaacaaatg ttccggttgt cctggacaca    540
cctgcggggt tggtgcgcgg tacggcacac cttcagagtg gtactgagag tgaggtgtca    600
aatgcgagta ttatcaatgt accctcattt ttgtatcagc aggatgtggt ggttgtgttg    660
ccaaagccct atggtgaagt acgggttgat attgcatttg gaggcaattt tttcgccatt    720
gttcccgcgg agcagttggg aattgatatc tccgttcaaa acctctccag gctgcaggag    780
gcaggagaac ttctgcgtac tgaaatcaat cgcagtgtga aggttcagca ccctcagctg    840
ccccatatta acactgtgga ctgtgttgag atatacggtc cgccaacgaa cccggaggca    900
aactacaaga acgttgtgat atttggcaat cgccaggcgg atcgctctcc atgtgggaca    960
ggcaccagcg ccaagatggc aacactttat gccaaaggcc agcttcgcat cggagagact   1020
```

```
tttgtgtacg agagcatact cggctcactc ttccagggca gggtacttgg ggaggagcga   1080

ataccggggg tgaaggtgcc ggtgaccaaa gatgccgagg aagggatgct cgttgtaacg   1140

gcagaaatta ctggaaaggc ttttatcatg ggtttcaaca ccatgctgtt tgacccaacg   1200

gatccgttta agaacggatt cacattaaag cagtagatct ggtagagcac agaaactatt   1260

ggggaacacg tgcgaacagg tgctgctacg tgaagggtat tgaatgaatc gttttttttt   1320

atttttattt tttattttta ttagtgcatt attattaaat tttttttttg ttttggggtt   1380

tcaacggtac cgcgttggga gcagggaagc gatagcggcc ggacaatttt ttgcttttat   1440

tttcattttc atcttcctac ccaacccct tggttccacc ggtcgcggcg gggtcttgtg    1500

ggtggaggag tcctaaatcc cgcacctcgg aggaataaac atatttcaat ttcatatctt   1560

ggaatcaaaa ggcat                                                     1575
```

<210> SEQ ID NO 9
<211> LENGTH: 1524
<212> TYPE: DNA
<213> ORGANISM: Trypanosoma cruzi

<400> SEQUENCE: 9

```
cgaacagggc aggaaaagct tctgtttgac caaaaatata aaattattaa gggcgagaaa     60

aaagaaaaga aaaaaaatca acgagcaaac aggagagaac accaacaaaa aagggaaatt    120

atgcgattta agaaatcatt cacatgcatc gacatgcata cggaaggtga agcagcacgg    180

attgtgacga gtggtttgcc acacattcca ggttcgaata tggcggagaa gaaagcatac    240

ctgcaggaaa acatggatta tttgaggcgt ggcataatgc tggaaccacg tggtcatgat    300

gatatgtttg gagccttttt atttgaccct attgaagaag gcgctgactt gggcatggta    360

ttcatggata ccggtggcta tttaaatatg tgtggacata actcaattgc agcggttacg    420

gcggcagttg aaacgggaat tgtgagcgtg ccggcgaagg caacaaatgt tccggttgtc    480

ctggacacac ctgcggggtt ggtgcgcggt acggcacacc ttcagagtgg tactgagagt    540

gaggtgtcaa atgcgagtat tatcaatgta ccctcatttt tgtatcagca ggatgtggtg    600

gttgtgttgc caaagcccta tggtgaagta cgggttgata ttgcatttgg aggcaatttt    660

ttcgccattg ttcccgcgga gcagttggga attgatatct ccgttcaaaa cctctccagg    720

ctgcaggagg caggagaact tctgcgtact gaaatcaatc gcagtgtgaa ggttcagcac    780

cctcagctgc cccatattaa cactgtggac tgtgttgaga tatacggtcc gccaacgaac    840

ccggaggcaa actacaagaa cgttgtgata tttggcaatc gccaggcgga tcgctctcca    900

tgtgggacag gcaccagcgc caagatggca acactttatg ccaaaggcca gcttcgcatc    960

ggagagactt ttgtgtacga gagcatactc ggctcactct tccagggcag ggtacttggg   1020

gaggagcgaa taccgggggt gaaggtgccg gtgaccaaag atgccgagga agggatgctc   1080

gttgtaacgg cagaaattac tggaaaggct tttatcatgg gtttcaacac catgctgttt   1140

gacccaacgg atccgtttaa gaacggattc acattaaagc agtagatctg gtagagcaca   1200

gaaactattg gggaacacgt gcgaacaggt gctgctacgt gaagggtatt gaatgaatcg   1260

ttttttttta tttttatttt ttatttttat tagtgcatta ttattaaatt ttttttttgt   1320

tttggggttt caacggtacc gcgttgggag cagggaagcg atagcggccg gacaattttt   1380

tgcttttatt ttcattttca tcttcctacc caaccccctt ggttccaccg gtcgcggcgg   1440

ggtcttgtgg gtggaggagt cctaaatccc gcacctcgga ggaataaaca tatttcaatt   1500

tcatatcttg gaatcaaaag gcat                                           1524
```

<210> SEQ ID NO 10
<211> LENGTH: 87
<212> TYPE: DNA
<213> ORGANISM: Trypanosoma cruzi

<400> SEQUENCE: 10
atgcgtaaaa gtgtctgtcc caaacaaaaa ttttttttt ccgccttccc attttttttt 60
tttttttgtg tgtttccctt gatctct 87

<210> SEQ ID NO 11
<211> LENGTH: 1395
<212> TYPE: DNA
<213> ORGANISM: Trypanosoma cruzi

<400> SEQUENCE: 11
aagaaatcat tcacatgcat cgacatgcat acggaaggtg aagcagcacg gattgtgacg 60
agtggtttgc cacacattcc aggttcgaat atggcggaga agaaagcata cctgcaggaa 120
aacatggatt atttgaggcg tggcataatg ctggaaccac gtggtcatga tgatatgttt 180
ggagcctttt tatttgaccc tattgaagaa ggcgctgact tgggcatggt attcatggat 240
accggtggct atttaaatat gtgtggacat aactcaattg cagcggttac ggcggcagtt 300
gaaacgggaa ttgtgagcgt gccggcgaag gcaacaaatg ttccggttgt cctggacaca 360
cctgcggggt tggtgcgcgg tacggcacac cttcagagtg gtactgagag tgaggtgtca 420
aatgcgagta ttatcaatgt accctcattt ttgtatcagc aggatgtggt ggttgtgttg 480
ccaaagccct atggtgaagt acgggttgat attgcatttg gaggcaattt tttcgccatt 540
gttcccgcgg agcagttggg aattgatatc tccgttcaaa acctctccag gctgcaggag 600
gcaggagaac ttctgcgtac tgaaatcaat cgcagtgtga aggttcagca ccctcagctg 660
ccccatatta acactgtgga ctgtgttgag atatacggtc cgccaacgaa cccggaggca 720
aactacaaga acgttgtgat atttggcaat cgccaggcgg atcgctctcc atgtgggaca 780
ggcaccagcg ccaagatggc aacactttat gccaaaggcc agcttcgcat cggagagact 840
tttgtgtacg agagcatact cggctcactc ttccagggca gggtacttgg ggaggagcga 900
ataccggggg tgaaggtgcc ggtgaccaaa gatgccgagg aagggatgct cgttgtaacg 960
gcagaaatta ctggaaaggc ttttatcatg ggtttcaaca ccatgctgtt tgacccaacg 1020
gatccgttta agaacggatt cacattaaag cagtagatct ggtagagcac agaaactatt 1080
ggggaacacg tgcgaacagg tgctgctacg tgaagggtat tgaatgaatc gttttttttt 1140
atttttattt tttattttta ttagtgcatt attattaaat tttttttttg ttttggggtt 1200
tcaacggtac cgcgttggga gcagggaagc gatagcggcc ggacaatttt ttgcttttat 1260
tttcattttc atcttcctac ccaacccccct tggttccacc ggtcgcggcg gggtcttgtg 1320
ggtggaggag tcctaaatcc cgcacctcgg aggaataaac atatttcaat ttcatatctt 1380
ggaatcaaaa ggcat 1395

<210> SEQ ID NO 12
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(20)
<223> OTHER INFORMATION: “n” represents inosine

<400> SEQUENCE: 12
ttnccraada tnacnacgtt 20

<210> SEQ ID NO 13
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(21)
<223> OTHER INFORMATION: "n" represents inosine

<400> SEQUENCE: 13
athgcnttyg gnggnaaytt t 21

<210> SEQ ID NO 14
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(20)
<223> OTHER INFORMATION: "n" represents inosine

<400> SEQUENCE: 14
ttnccraada tnacnacgtt 20

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
ctctcccatg gggcaggaaa agcttctg 28

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ctgagctcga ccagatctat ctgc 24

<210> SEQ ID NO 17
<211> LENGTH: 1665
<212> TYPE: DNA
<213> ORGANISM: Trypanosoma cruzi

<400> SEQUENCE: 17
cctttttctt tttaaaaaca aaaaaaattc cggggggaat atggaacagg gtatatgcgt 60
aaaagtgtct gtcccaaaca aaaatttttt ttttccgcct tcccattttt tttttttttt 120
tgtgtgtttc ccttgatctc tcgaacaggg caggaaaagc ttctgtttga ccaaaaatat 180
aaaattatta agggcgagaa aaaagaaaag aaaaaaaatc aacgagcaaa caggagagaa 240
caccaacaaa aaagggaaat tatgcgattt aagaaatcat tcacatgcat cgacatgcat 300
acggaaggtg aagcagcacg gattgtgacg agtggtttgc cacacattcc aggttcgaat 360

```
atggcggaga agaaagcata cctgcaggaa aacatggatt atttgaggcg tggcataatg     420

ctggaaccac gtggtcatga tgatatgttt ggagcctttt tatttgaccc tattgaagaa     480

ggcgctgact tgggcatggt attcatggat accggtggct atttaaatat gtgtggacat     540

aactcaattg cagcggttac ggcggcagtt gaaacgggaa ttgtgagcgt gccggcgaag     600

gcaacaaatg ttccggttgt cctggacaca cctgcggggt tggtgcgcgg tacggcacac     660

cttcagagtg gtactgagag tgaggtgtca aatgcgagta ttatcaatgt accctcattt     720

ttgtatcagc aggatgtggt ggttgtgttg ccaaagccct atggtgaagt acgggttgat     780

attgcatttg gaggcaattt tttcgccatt gttcccgcgg agcagttggg aattgatatc     840

tccgttcaaa acctctccag gctgcaggag gcaggagaac ttctgcgtac tgaaatcaat     900

cgcagtgtga aggttcagca ccctcagctg ccccatatta acactgtgga ctgtgttgag     960

atatacggtc cgccaacgaa cccggaggca aactacaaga acgttgtgat atttggcaat    1020

cgccaggcgg atcgctctcc atgtgggaca ggcaccagcg ccaagatggc aacactttat    1080

gccaaaggcc agcttcgcat cggagagact tttgtgtacg agagcatact cggctcactc    1140

ttccagggca gggtacttgg ggaggagcga ataccggggg tgaaggtgcc ggtgaccaaa    1200

gatgccgagg aagggatgct cgttgtaacg gcagaaatta ctggaaaggc ttttatcatg    1260

ggtttcaaca ccatgctgtt tgacccaacg gatccgttta agaacggatt cacattaaag    1320

cagtagatct ggtagagcac agaaactatt ggggaacacg tgcgaacagg tgctgctacg    1380

tgaagggtat tgaatgaatc gttttttttt atttttattt tttattttta ttagtgcatt    1440

attattaaat tttttttttg ttttggggtt tcaacggtac cgcgttggga gcagggaagc    1500

gatagcggcc ggacaatttt ttgcttttat tttcattttc atcttcctac ccaacccccct   1560

tggttccacc ggtcgcggcg gggtcttgtg ggtggaggag tcctaaatcc cgcacctcgg    1620

aggaataaac atatttcaat ttcatatctt ggaatcaaaa ggcat                    1665
```

<210> SEQ ID NO 18
<211> LENGTH: 4
<212> TYPE: PRT
<213> ORGANISM: Trypanosoma cruzi

<400> SEQUENCE: 18

```
Trp Ile Ile Lys
  1
```

<210> SEQ ID NO 19
<211> LENGTH: 11
<212> TYPE: PRT
<213> ORGANISM: Trypanosoma cruzi

<400> SEQUENCE: 19

```
Ile Val Thr Gly Ser Leu Pro Asp Ile Ser Gly
  1               5                  10
```

<210> SEQ ID NO 20
<211> LENGTH: 16
<212> TYPE: PRT
<213> ORGANISM: Trypanosoma cruzi

<400> SEQUENCE: 20

```
Ala Thr Asn Val Pro Val Val Leu Asp Thr Pro Ala Gly Leu Val Arg
  1               5                  10                  15
```

<210> SEQ ID NO 21
<211> LENGTH: 9
<212> TYPE: PRT
<213> ORGANISM: Trypanosoma cruzi

<400> SEQUENCE: 21

Val Asp Ile Ala Phe Gly Gly Asn Phe
1 5

<210> SEQ ID NO 22
<211> LENGTH: 8
<212> TYPE: PRT
<213> ORGANISM: Trypanosoma cruzi

<400> SEQUENCE: 22

Asn Val Val Ile Phe Gly Asn Arg
1 5

<210> SEQ ID NO 23
<211> LENGTH: 7
<212> TYPE: PRT
<213> ORGANISM: Trypanosoma cruzi

<400> SEQUENCE: 23

Met Ala Thr Leu Tyr Ala Lys
1 5

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide

<400> SEQUENCE: 24
tccgtatcca tgtcgatgc 19

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
tattattgat acagtttctg 20

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide

<400> SEQUENCE: 26
ctctcccatg gggcaggaaa agcttctg 28

<210> SEQ ID NO 27
<211> LENGTH: 5
<212> TYPE: PRT
<213> ORGANISM: Trypanosoma cruzi

<400> SEQUENCE: 27

Ser Pro Cys Gly Thr
1 5

CLONING, SEQUENCING AND EXPRESSION OF A GENE ENCODING AN EUKARYOTIC AMINO ACID RACEMASE, AND DIAGNOSTIC, THERAPEUTIC, AND VACCINATION APPLICATIONS OF PARASITE AND VIRAL MITOGENS

CROSS-REFERENCE TO RELATED APPLICATIONS

This is a continuation of U.S. application Ser. No. 10/662,437, filed Sep. 16, 2003 now abandoned, which is a divisional application of U.S. application Ser. No. 09/725,945, filed Nov. 30, 2000 now U.S. Pat. No. 6,713,617, and claims the benefit of U.S. Provisional Application Ser. No. 60/168,631, filed Dec. 3, 1999; U.S. Provisional Application Ser. No. 60/220,207, filed Jul. 24, 2000; and U.S. Provisional Application Ser. No. 60/221,117, filed Jul. 27, 2000, all of which are relied upon and incorporated by reference herein.

BACKGROUND OF THE INVENTION

This invention relates to the discovery of a new gene, which is the first isolated and cloned, that encodes an amino acid eukaryotic racemase. The invention covers, particularly, the Tc45 gene encoding a *Trypanosoma cruzi*-derived B-cell mitogen. The encoded protein also is a eukaryotic proline racemase. The invention also relates to a process of production of D-amino acid using an eukaryotic amino acid racemase. This invention also relates to the use of the protein encoded by the Tc45 gene to induce a protective immune response against *T. cruzi* infection in a human. This invention also relates to methods of using other parasite mitogens and viral mitogens for inducing protective immunity against the corresponding parasitic or viral infections in humans.

The process of production of an D-amino acid by using a L-amino acid source comprises the use of an eukaryotic amino acid racemase specific for the amino acid of interest, the said racemase being produced from a recombinant expression system containing a vector having a polynucleotide sequence encoding the said enzyme. In prokaryotic hosts, the racemases are known to be implicated in the synthesis of D-amino acids and/or in the metabolism of L-amino acids. Therefore, the presence of free D-amino acids in tumors and in progressive autoimmune and degenerative diseases suggests the biological importance of eukaryotic amino acid racemases. It is well known that proteins or peptides containing D-amino acids are resistant to proteolysis by host enzymes. In addition, such proteins containing D-amino acids, at least one D-amino acid residue, can display antibiotic or immunogenic properties.

Isolation and characterization of molecules playing a key role in parasite metabolism, or in their interactions with the host immune defense, are fundamental for the development of rational strategies for vaccination and therapy. Attempts to provide effective immunity to parasites are limited by poor specific immune responses to parasite antigenic molecules in early phases of infection. Lymphocyte polyclonal activation is a generalized mechanism of immune evasion amongst pathogens[1]. Such "parasite evasion" owes, at least in part, to the release of mitogenic or superantigenic moieties that inhibit host specific responses by triggering polyclonal, parasite non-specific lymphocyte activation. The resulting non-specific immune responses are associated with immunosuppression and autoimmunity, as observed in human and experimental infections by the protozoan parasite *Trypanosoma cruzi*, the etiological agent of Chagas disease[2-6].

To date, there is no effective treatment or vaccine against *Trypanosoma cruzi* infection and Chagas disease pathology. Attempts to isolate immunodominant protective epitopes have failed[1]. Using a mouse model of *T. cruzi* infection it has previously been shown that reduced levels of polyclonal lymphocyte responses correlate with resistance to infection and cardiopathy[2, 7-9]. As we have suggested, and has been demonstrated by Arala-Chaves[31] for *Candida albicans* infections, mitogenic moieties can be used as vaccination targets to induce specific neutralization of the mitogen, thus aborting the microorganism "strategy" to deviate immune responses into non-specific polyclonal activation and immunosuppression. Understanding the mechanisms underlying "non-specific" lymphocyte activation may open the way for their neutralization, and thus allow for effective immune responses against infectious agents. There is a need in the art for a molecule that could be an appropriate target for such attempts.

Furthermore, there is a growing interest in the biological role of D-amino acids, either as free molecules or within polypeptide chains in human brain, tumors, anti-microbial and neuropeptides, as well as in "protein fatigue"[32], suggesting widespread biological implications. Research on D-amino acids in living organisms has been hampered by their difficult detection. However, recent purification of a serine racemase from mammalian brain[33] indicates conservation throughout evolution. There also exists a need in the art for racemases that are specific for known compounds.

SUMMARY OF THE INVENTION

This invention aids in fulfilling these needs in the art. More particularly, this invention relates to the characterization of a parasite molecule implicated in polyclonal responses that may serve as a novel target for vaccination and therapy. After identifying a protein with B-cell mitogenic properties in culture supernatants of infective parasite forms, the corresponding gene was cloned and its genomic organization was characterized. The protein has been characterized as a cofactor independent proline racemase, with strong homology to the proline racemase isolated from *Clostridium sticklandii*, thus providing the first report on an eukaryotic amino acid racemase gene.

In particular, this invention provides a purified peptide comprising an amino acid sequence (SEQ ID NOS: 1, 2, 3 and 4) encoded by the Tc45 gene. This invention also provides polypeptide fragments derived from SEQ ID NOS: 7, 8, 9, 10 and 11 containing at least 10 amino acids.

This invention additionally provides purified polynucleotides comprising the nucleic acid sequences of the Tc45 gene (SEQ ID NOS: 7, 8, 9, 10 and 11). This invention also provides nucleic acid fragments derived from SEQ ID NOS: 7, 8, 9, 10 and 11 containing 15 to 40 nucleotides.

Additionally, the invention includes a purified polynucleotide that hybridizes specifically under conditions of moderate stringency with a polynucleotide of SEQ ID NOS: 7, 8, 9, and 10.

SEQ. ID 7 represents the full nucleotide sequence encoding the *Trypanosoma cruzi* proline racemase and N-terminal signal sequence and the 5' and 3' flanking non-coding regions.

The SEQ ID 8 represents the full nucleotide sequence and its corresponding polypeptide sequences [including the N terminal signal sequence and the 3' non-coding flanking region] coding for a proline racemase of *T. cruzi.*

The construct as disclosed in SEQ ID 8 deleted of the 3' non-coding flanking region and inserted in the PET28 vector (NOVAGEN), transformed in *E. coli* DH5α was deposited at the CNCM under the accession number I-2344.

A derived construct of I-2344 deleted of nucleotide sequence corresponding to the signal peptide coding sequences, which is described in SEQ ID 3, is used for the production of a recombinant active proline racemase in *E. coli*. The *E. coli* DH 5α containing the plasmid with an insert of 239 base pairs deposited at CNCM under accession number I-2221, was obtained after amplification of the region by PCR technique with the primers SEQ ID Nos. 12 and 13. The insert was cloned into p TOPO II commercialized by INVITROGEN and then transformed in *E. coli.*

The invention further includes polynucleotide fragments comprising at least 10 nucleotides capable of hybridization under conditions of moderate stringency conditions with any one of the nucleotide sequences enumerated above.

In another embodiment of the invention, a recombinant DNA sequence comprising at least one nucleotide sequence enumerated above and under the control of regulatory elements that regulate the expression of racemase activity in a host is provided.

The invention also includes a recombinant host cell comprising a polynucleotide sequence enumerated above or the recombinant vector defined above.

In still a further embodiment of the invention, a method of detecting parasitic strains that contain the polynucleotide sequences set forth above is provided.

Additionally, the invention includes kits for the detection of the presence of parasitic strains that contain the polynucleotide sequences set forth above.

The invention also contemplates antibodies recognizing peptide fragments or polypeptides encoded by the polynucleotide sequences enumerated above.

Still further, the invention provides for a screening method for active molecules for the treatment of infections due to parasites, particularly *T. Cruzi*, based on the detection of activity of these molecules on parasites.

This invention further provides an immunizing composition containing at least a purified protein, or a fragment thereof, capable of inducing an immune response in vivo. The immune response can be a mitogenic polyclonal immunoresponse in vivo. The immunizing composition is suitable for use against a parasite infection under sub-mitogenic doses.

This invention also provides a process to access the mitogenicity of a molecule called mitogen and the procedures to determine the sub-mitogenic dose suitable as an immunizing composition for use against a parasite infection.

A vaccine composition of the invention for use against a *T. cruzi* infection comprises a purified 38 to P45 kda protein or a fragment thereof.

A method of inhibiting an eukaryotic protein with an amino acid racemase activity according to the invention comprises treating a patient by administering an effective amount of a molecule that inhibits the eukaryotic protein. The parasite can be *T. cruzi.*

This invention also provides a process for screening a molecule capable of inhibiting the amino acid racemase activity of an eukaryotic protein comprising the steps of:

contacting the purified eukaryotic racemase protein with standard doses of a molecule to be tested;

measuring inhibition of racemase activity; and selecting the molecule.

BRIEF DESCRIPTION OF THE DRAWINGS

This invention will be more fully described with reference to the drawings in which:

FIG. 1 depicts the proliferative activity of total spleen cells stimulated in vitro by a 45 kDa B-cell polyclonal activator isolated from parasite culture supernatants.

FIG. 2 shows the homology or similarity between the Tc45 protein (Tc) [SEQ ID NO:1] and the bacterial proline racemases *Clostridium sticklandii* (Cs) [SEQ ID NO.:5] and *Pseudomonas aeruginosa* (Pa) [SEQ ID NO.:6]. The computer-predicted signal peptide is indicated by a double arrow; peptide sequences obtained by microsequencing appear underlined; peptides used for designing degenerate primers appear in italic characters. Proline racemase active sites are boxed; dashes indicate gaps generated for best fit.

FIG. 3 shows the genomic organization and transcription of the Tc45 gene.

FIG. 4 shows the results of characterization of rTcPA45 activities in vitro.

FIG. 5 shows the nucleotide sequence [SEQ ID NO: 17] and peptide sequence [SEQ ID NO: 1] of TcPA45. The polypyrimidine rich region, splice leader acceptor sites, signal peptide, and polyadenylation site are indicated. The peptide sequences obtained by microsequencing of the native TcPA45 protein are underlined.

Western blot: membranes containing in:

Lane 1: total epimastigote extract from $5\times10^5$ epimastigote forms

Lane 2: Epimastigote culture supernatant

Lane 3: Soluble fraction of epimastigote extract (cytosolic) from $5\times10^5$ epimastigote forms.

Lane 4: Insoluble fraction of epimastigote extract from $5\times10^5$ epimastigote forms Lane 5: as in lane 1, from 10× more parasite forms ($5\times10^6$ epimastigotes)

Lane 6: as in lane 3, from 10× more parasite forms ($5\times10^6$ epimastigotes)

Lane 7: as in lane 2

Lane 8: as in lane 4, from 10× more parasite forms ($5\times10^6$ epimastigotes)

Figure 6:
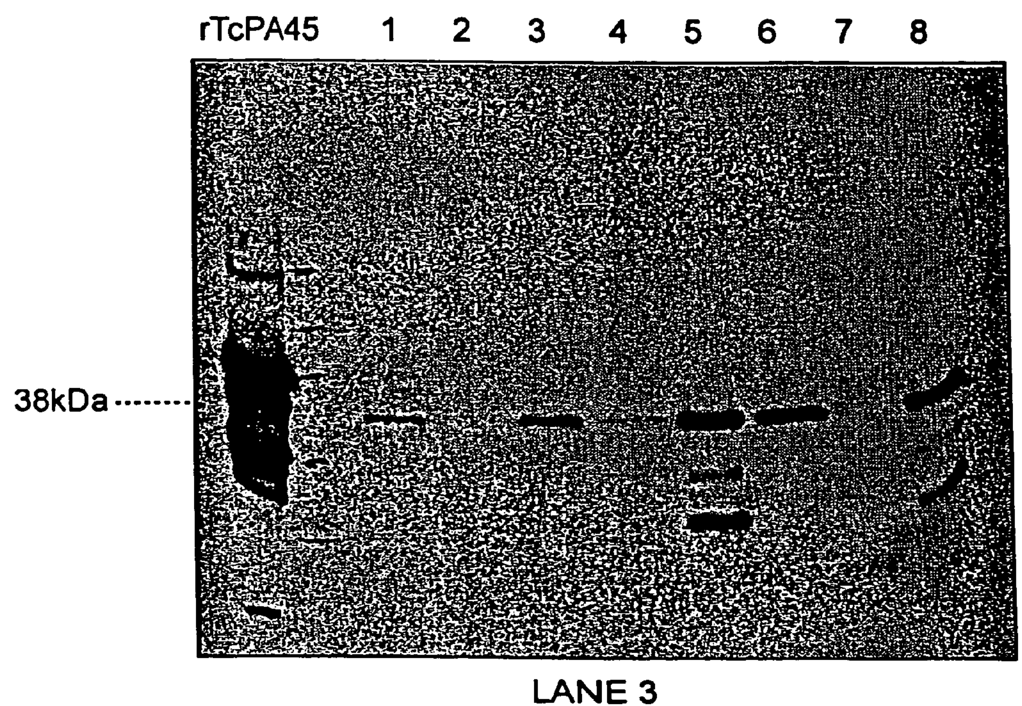
FIG. 6 is a demonstration of a cytosolic proline racemase in epimastigote forms of *T. cruzi.*

Membranes were incubated with mouse polyclonal antibodies raised against the rTcPA45 protein (primary antibody). Second step reaction was done with goat anti-mouse IgG-horseradish peroxidase (human absorbed). Reactivities were developed by ECL-chemiluminescence Amersham kit. FIG. 6 represents 10 seconds exposure of the film.

Figure 7:
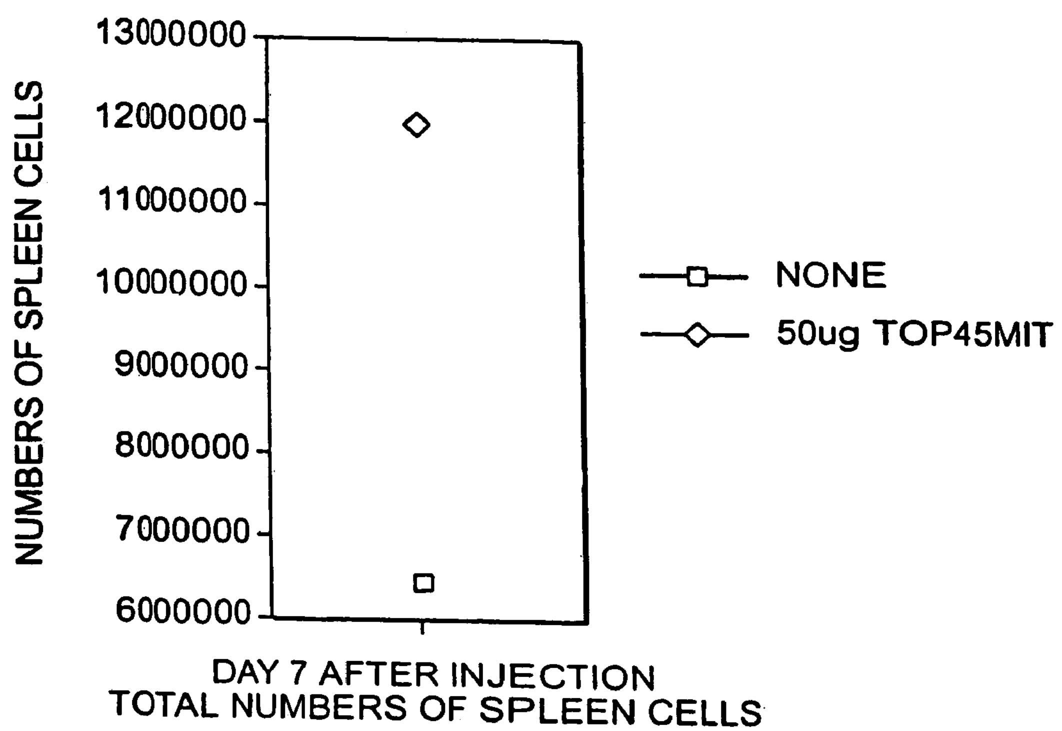
Figures 8A, 8B:
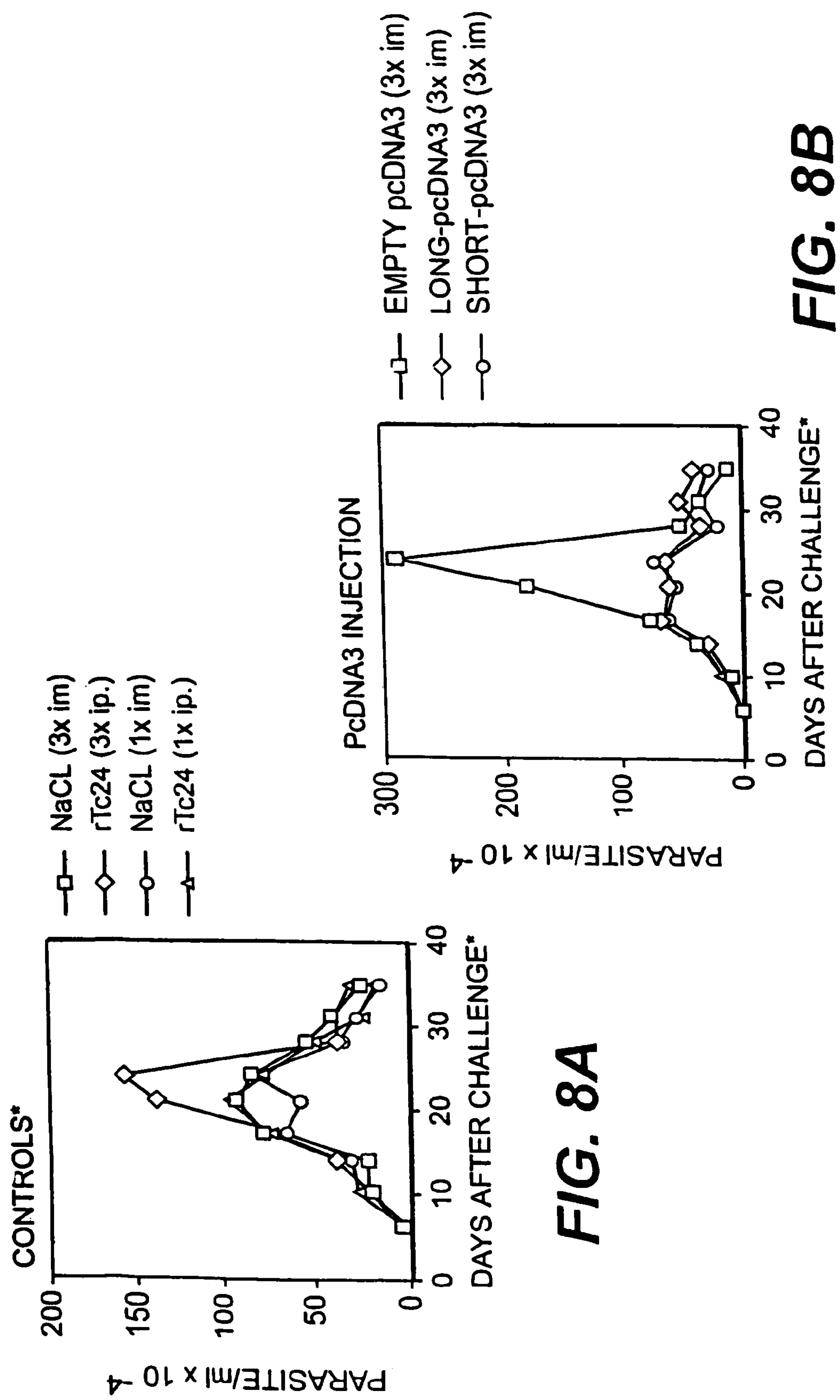
Figures 8C, 8D, 8E:
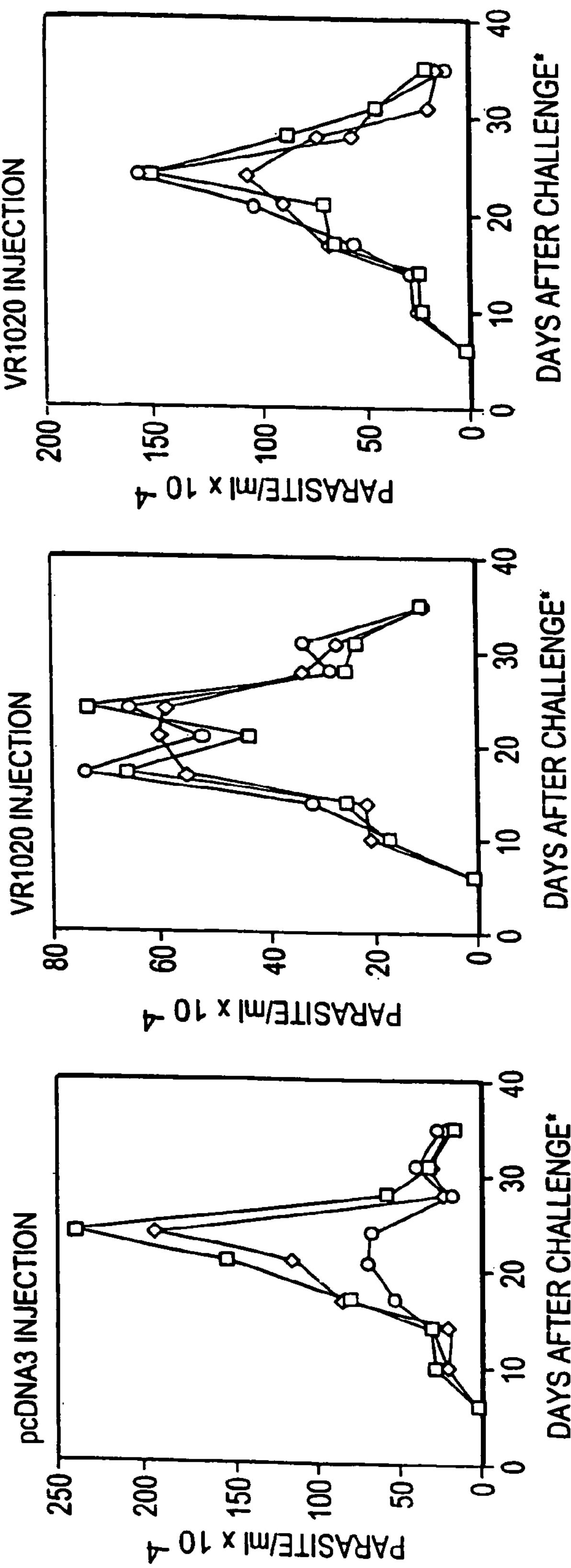

FIG. 7 depicts the results of an ELISPOT assay. Spots correspond to immunoglobulin-producing B-cell (of a particular isotype) directed to the coated antigen (here: goat anti-mouse immunoglobulins or rTcPA45). See also Example 10 and Table 1.

FIGS. 8A, 8B, 8C, 8D, and 8E depict the results of DNA vaccination using various DNA constructs. See also Example 11.

Figure 9:
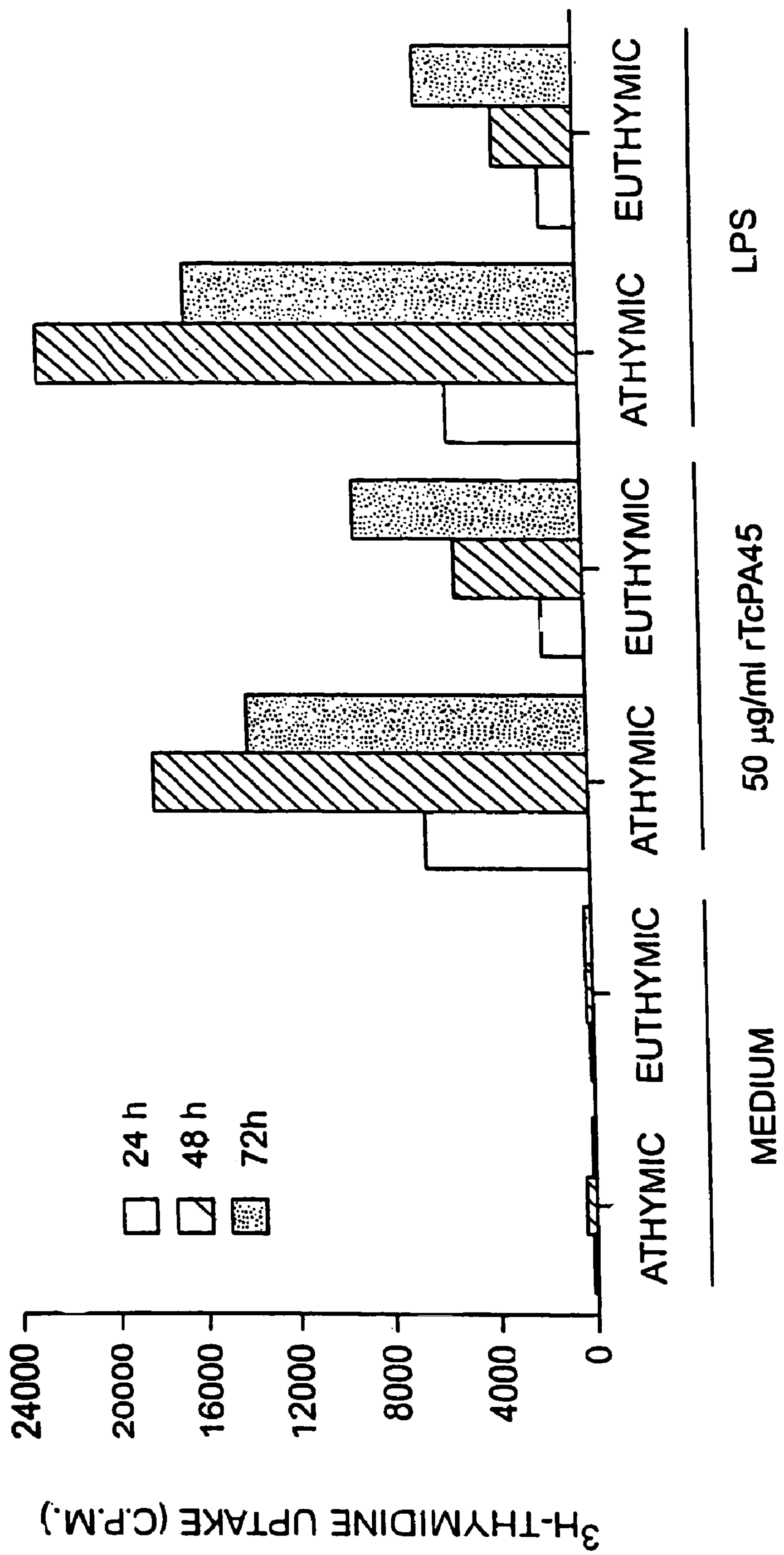

FIG. 9 depicts the characterization of rTcPA45 mitogenic activity. Proliferative activity of total splenocytes obtained from athymic or euthymic mice in the presence of rTcPA45 or lipopolysaccharide is shown at 24 h (□), 48 h (/) or 72 h (■).

FIG. 10 depicts the differential expression of rTcPA45 protein in the parasite.

FIG. 10A depicts the cellular localization of the Tc45 protein in different life stages of the parasite, shown by indirect immunofluorescence using polyclonal mouse serum against rTcPA45 followed by staining with the Alexa 488™ goat antibody against mouse IgG (H+ L), $F(ab')_2$ fragment conjugate (bottom row), compared with control staining using the Alexa 488™ $F(ab')_2$ fragment conjugate alone (top left) or after incubation of the parasites with serum from chronically infected mice (Chronic serum).

Figure 10B:
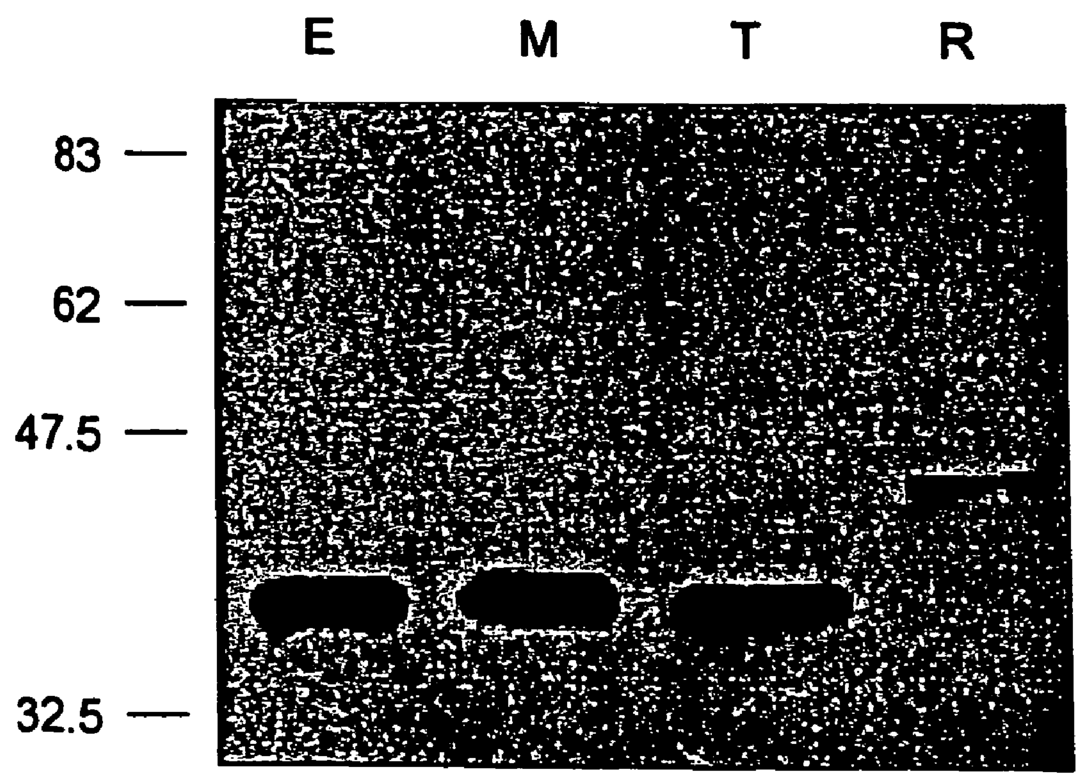
Figure 10C:
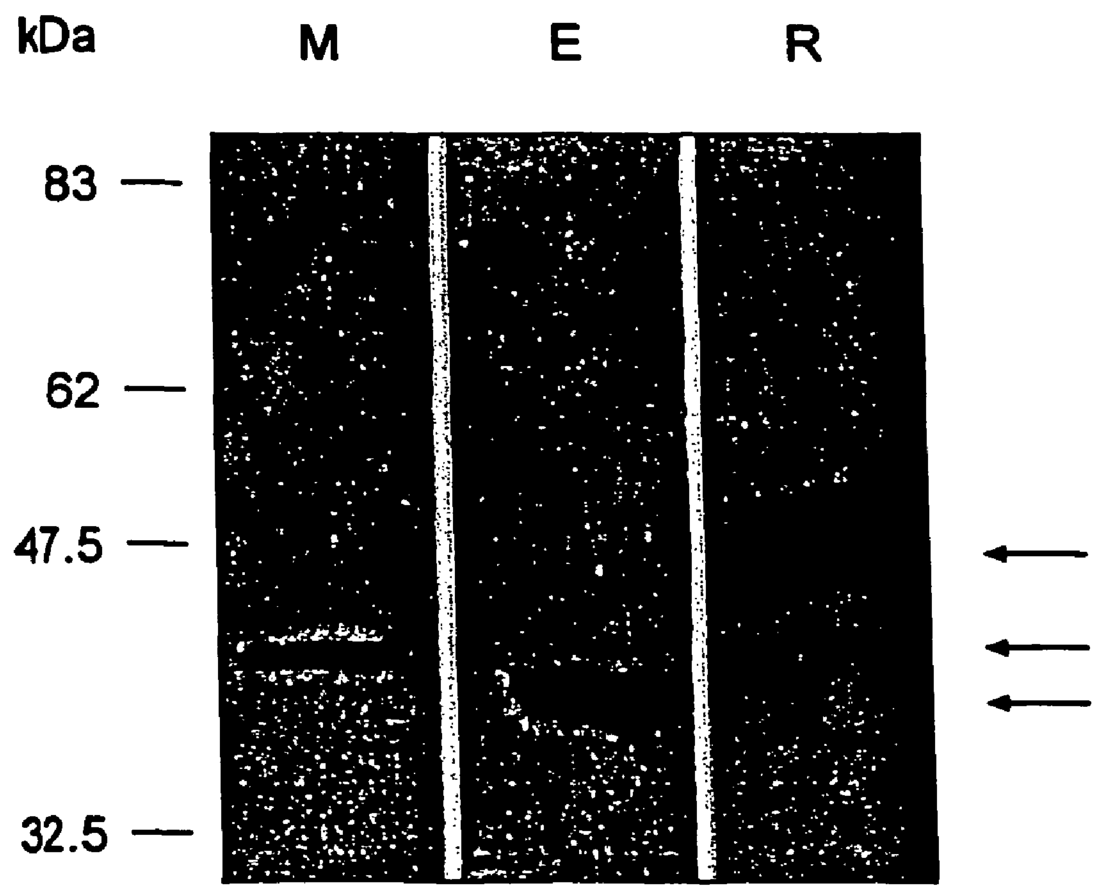

FIGS. 10B and 10C depict the detection of Tc45 protein in total extracts of epimastigote (E), metacyclic (M) and trypomastigote (T) forms of the parasite, compared with recombinant rTcPA45 (R) protein, by western blot analysis. Arrows, calculated molecular weights for isoforms of the TcPA45 (R) protein.

Figure 10D:
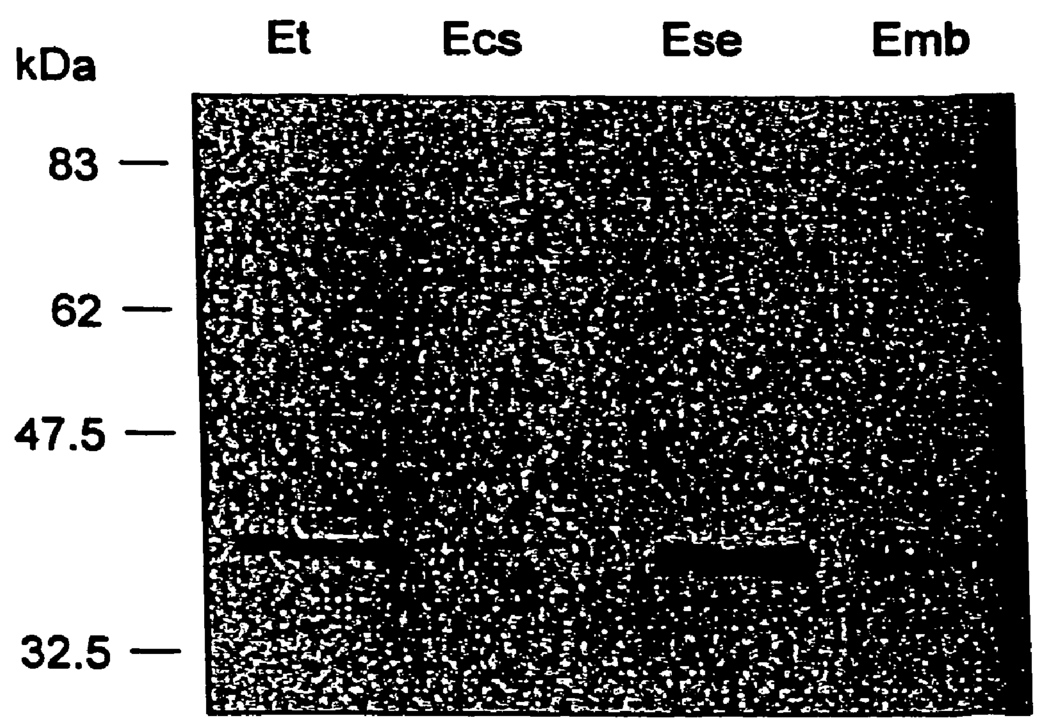

FIG. 10D depicts the presence of the 39-kDa isoform of the Tc45 protein in total (Et), soluble (Ese) and insoluble (Emb) sonic extracts of non-infective epimastigote forms of the parasite, compared with its absence in culture supernatants (Ecs). Molecular sizes (b-d) are shown at the left margins.

FIG. 11 depicts the correlation between mitogenic and racemase activities.

Figure 11A:
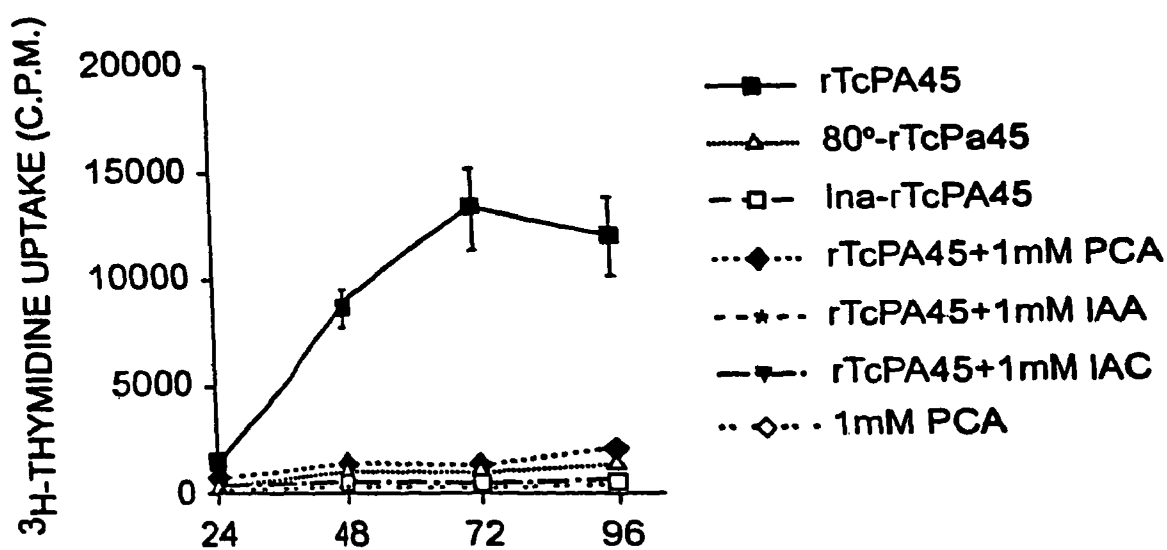

FIG. 11A depicts the proliferative activity of total mouse splenocytes in the presence of rTcPA45 protein that is enzymatically active (rTcPA45) or lacking racemase activity by being heated (80°-rTcPA45), by long term storage at 4° C. (Ina-rTcPA45), or by pre-incubation of rTcPA45 with pyrrole-Z carboxylic acid (rTcPA45+1 mM PCA), Iodoacetamide (rTcPA45+1 mM IAA) or iodoacetate (rTcPA45+1 mM IAC) inhibitors, compared with 1 mM pyrrole-2-carboxylic acid 1 mMPCA) alone.

Figure 11B:
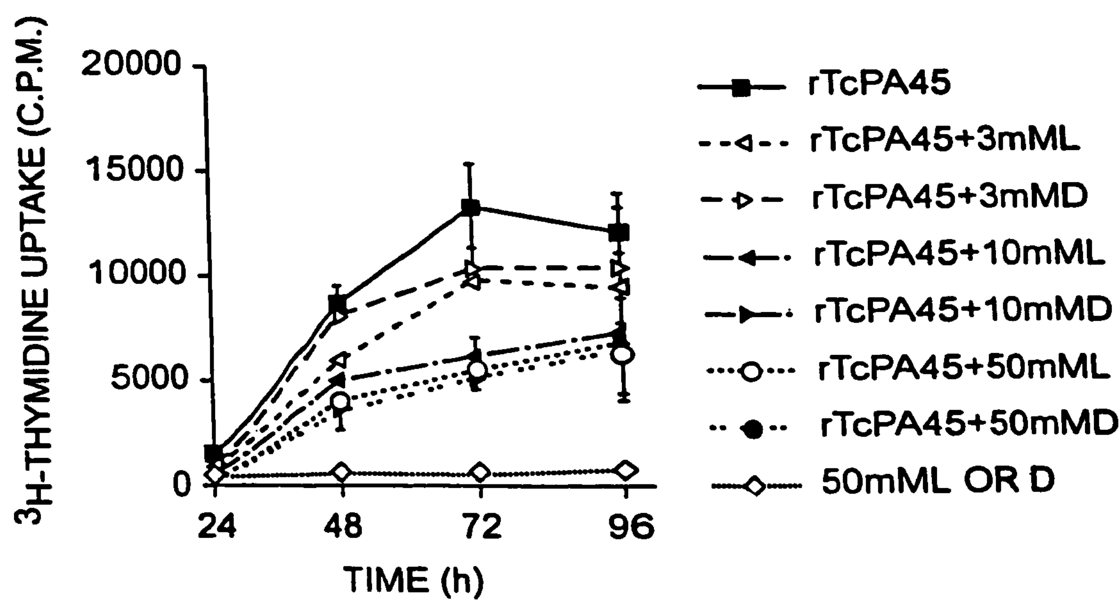

FIG. 11B depicts the competitive inhibition of rTcPA45-induced proliferative activity of total mouse lymphocytes by increasing concentrations of L- or D-proline substrates. Shown are controls, cultures of splenocytes with 50 mM L- or D-proline alone. c.p.m., counts per minute.

Figure 12:
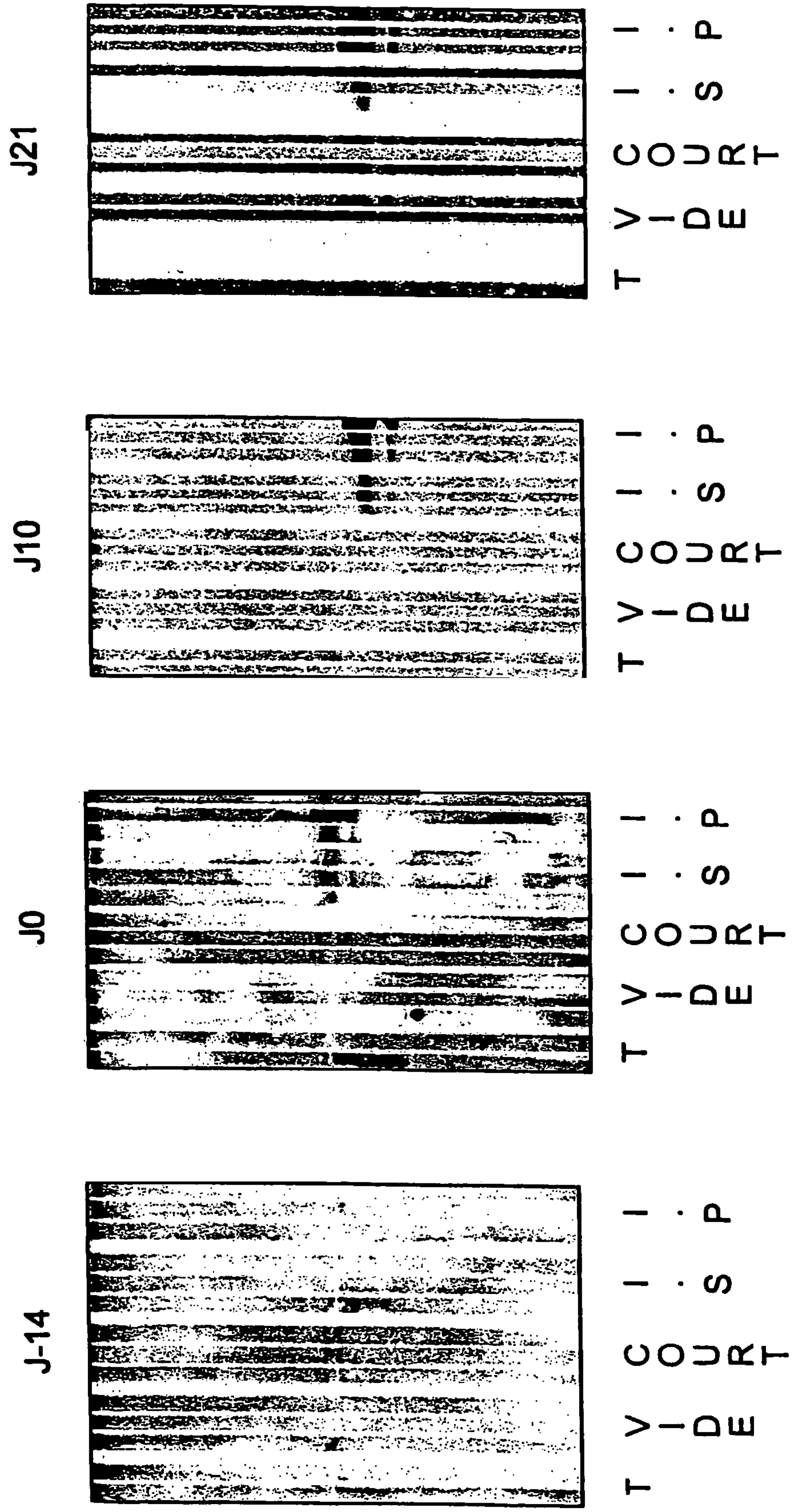

FIG. 12 depicts the results of Western blot of mouse specific immune responses directed to mitogenic rTcPA45 following immunization. See also Example 15.

Figure 13:
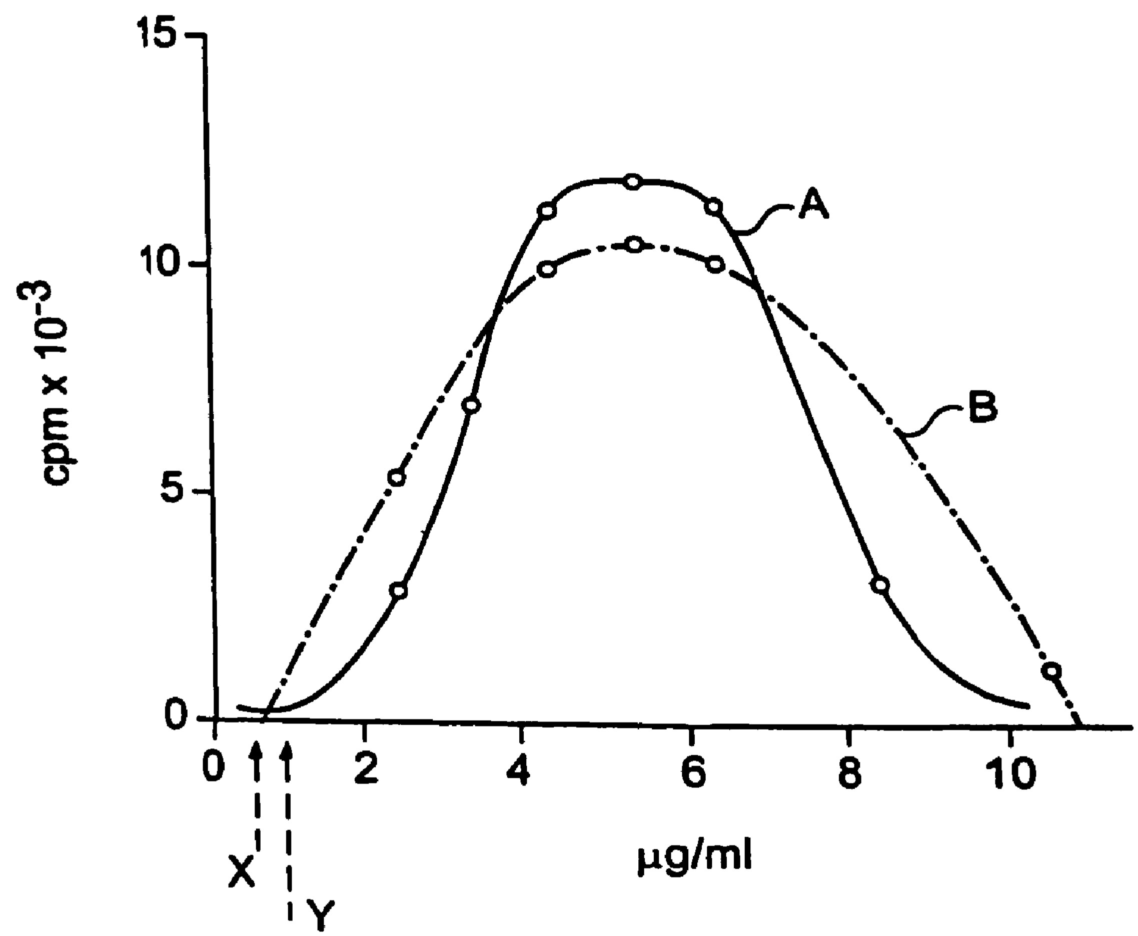

FIG. 13 depicts two dose-response curves for two different hypothetical mitogens, A and B, in an assay of proliferative activity described hereinafter.

FIG. 14 depicts the results of immunization according to the invention.

FIG. 14 A. DNA vaccination. 8 week old BALB/c mice (5 mice/group) were injected 3 times (i.m., 50 μg of plasmid/femoral quadriceps) at 3 weeks interval with the following constructs: pcDNA3 vector alone as control, or pcDNA3 containing the full encoding sequence of the TcPA45 gene with (Long) or without (Short) the fragment encoding the signal peptide. Mice were challenged 4 weeks after the last injection with $10^4$ infective forms of the parasite/mouse, and the parasitemia was scored during 35 days.

OBS. It is worth noting that BALB/c mice were treated by almost 2 months (9 weeks) to follow the vaccination protocol and were challenged at 21 weeks of age. Its is well known that mice of more than 9 weeks of age are naturally more resistant to the experimental infection with *Trypanosoma cruzi* and no morality is observed.

The results using this vaccination protocol revealed that 3 injections of pcDNA3 containing either the Short or Long encoding sequences of the TcPA45 gene, are able to reduce by more than 85% the parasitemia levels.

Figures 14A, 14B:
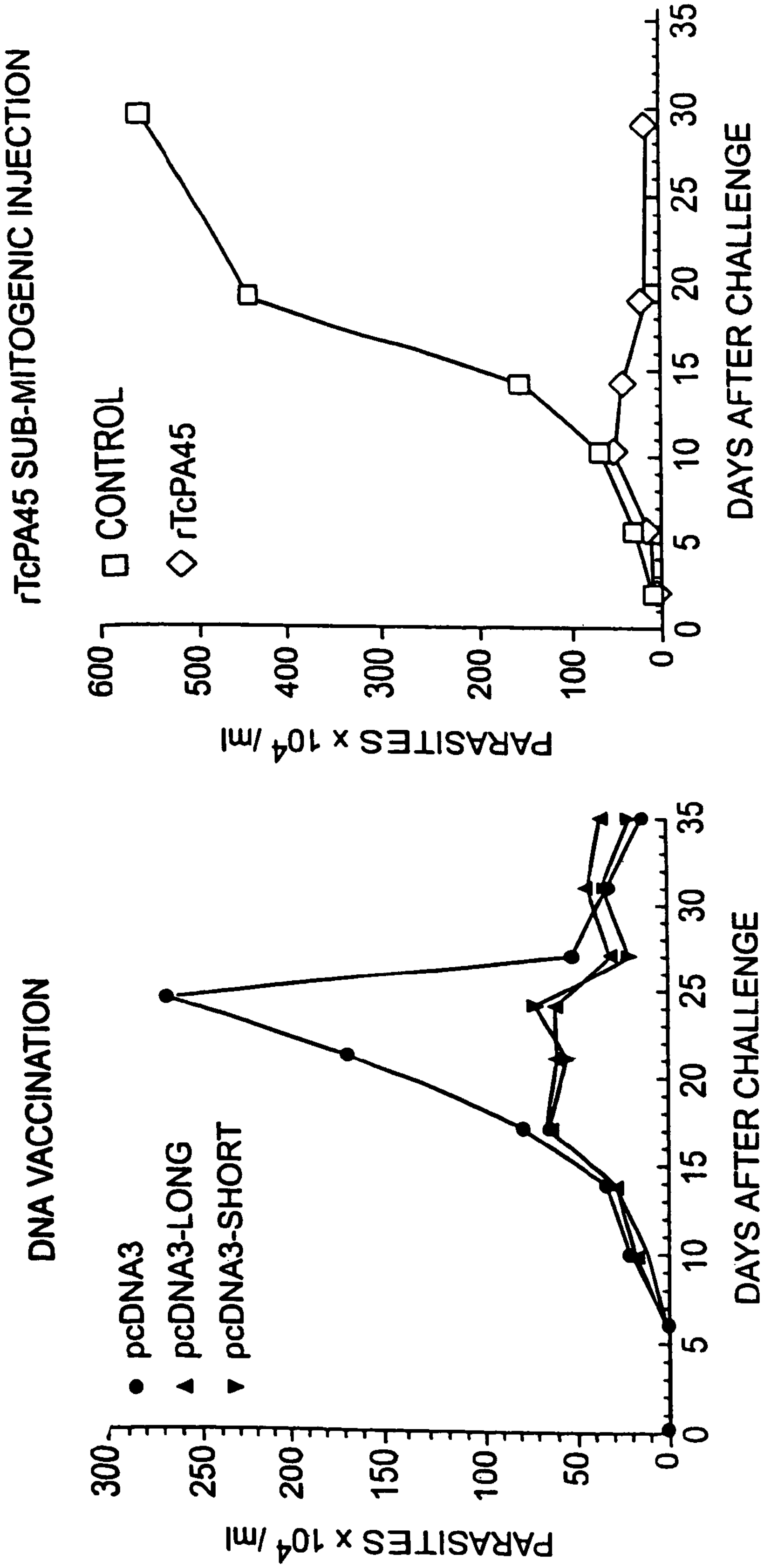

FIG. 14B. rTcPA45 injection. 6 week old BALB/c mice were injected intraperitoneally (i.p.) with 10 ηg of rTcPA45 and then boosted i.p. one week later with 50 μg of rTcPA45. Mice were challenged 1 week after the boost with $10^4$ infective forms of the parasite/mouse, and the parasitemia was scored during 30 days. Control mice did not receive any treatment before infection.

FIG. 15 depicts SEQ ID NO: 2, an amino acid sequence encoded by the Tc45 gene with markings as described for FIG. 2.

FIG. 16 depicts SEQ ID NO: 4, an amino acid sequence encoded by the Tc45 gene with markings as described for FIG. 2.

FIGS. 17A and 17B depict SEQ ID NO: 7, a nucleic acid sequence of Tc45 with markings as described for FIG. 5.

FIGS. 18A and 18B depict SEQ ID NO: 8, a nucleic acid sequence of the Tc45 gene with markings as described for FIG. 5.

FIGS. 19A and 19B depict SEQ ID NO: 9, a nucleic acid sequence of the Tc45 gene with markings as indicated for FIG. 5.

FIG. 20 depicts SEQ ID NO: 10, a nucleic acid sequence of the Tc45 gene with markings as indicated for FIG. 5.

FIGS. 21A and 21B depict SEQ ID NO: 11, a nucleic acid sequence of the Tc45 gene with markings as indicated for FIG. 5.

DETAILED DESCRIPTION

Having noted that proteins released from trypomastigote forms of *Trypanosoma cruzi* behave as polyclonal B-cell activators[10], it was hypothesized that infective metacyclic forms would display an increased production of mitogenic molecules, thereby promoting such a mechanism of immune evasion. To investigate the release of proteins with B-cell mitogenic activity by *T. cruzi*, culture supernatants of in vitro differentiated metacyclic trypornastigotes in a protein-free defined medium were produced[11]. Lymphocyte mitogenic activity in total concentrated culture supernatants was confirmed by lymphocyte proliferation assays.

Briefly, freshly recovered splenocytes from 8 week old male Balb/c mice seeded at a concentration of $5\times10^4$ cells/well were incubated for 24, 48 and 72 h in 5% FCS RPMI-1640 medium. A 16 h $^3$H-thymidine pulse at 1 μCi/well was performed before harvesting. $^3$H-Thymidine uptake was determined in a beta-plate liquid scintillation counter (LKB-Wallac). All points were done in triplicate and the corresponding standard deviation calculated. For comparison, $^3$H-thymidine uptake after 48 h in the presence of ConA (10 μg/ml) and LPS (5 μg/ml) was 32000 c.p.m. and 3500 c.p.m., respectively. T-cell depletion was performed by incubating freshly recovered spleen cells for 30 min at 37° C. in the presence of anti-Thy 1.2 monoclonal antibody (Cedarlane) and rabbit complement (Cedarlane). In order to rule out a possible mitogenic effect due to LPS contamination in samples, proliferation assays were also performed on freshly recovered splenocytes from the LPS non-responder mouse strain C3H/Hej. Same levels of proliferation were verified. Balb/c mice were purchased from Charles River, France. C3H/Hej mice were maintained in our animal facilities.

Figure 1A:
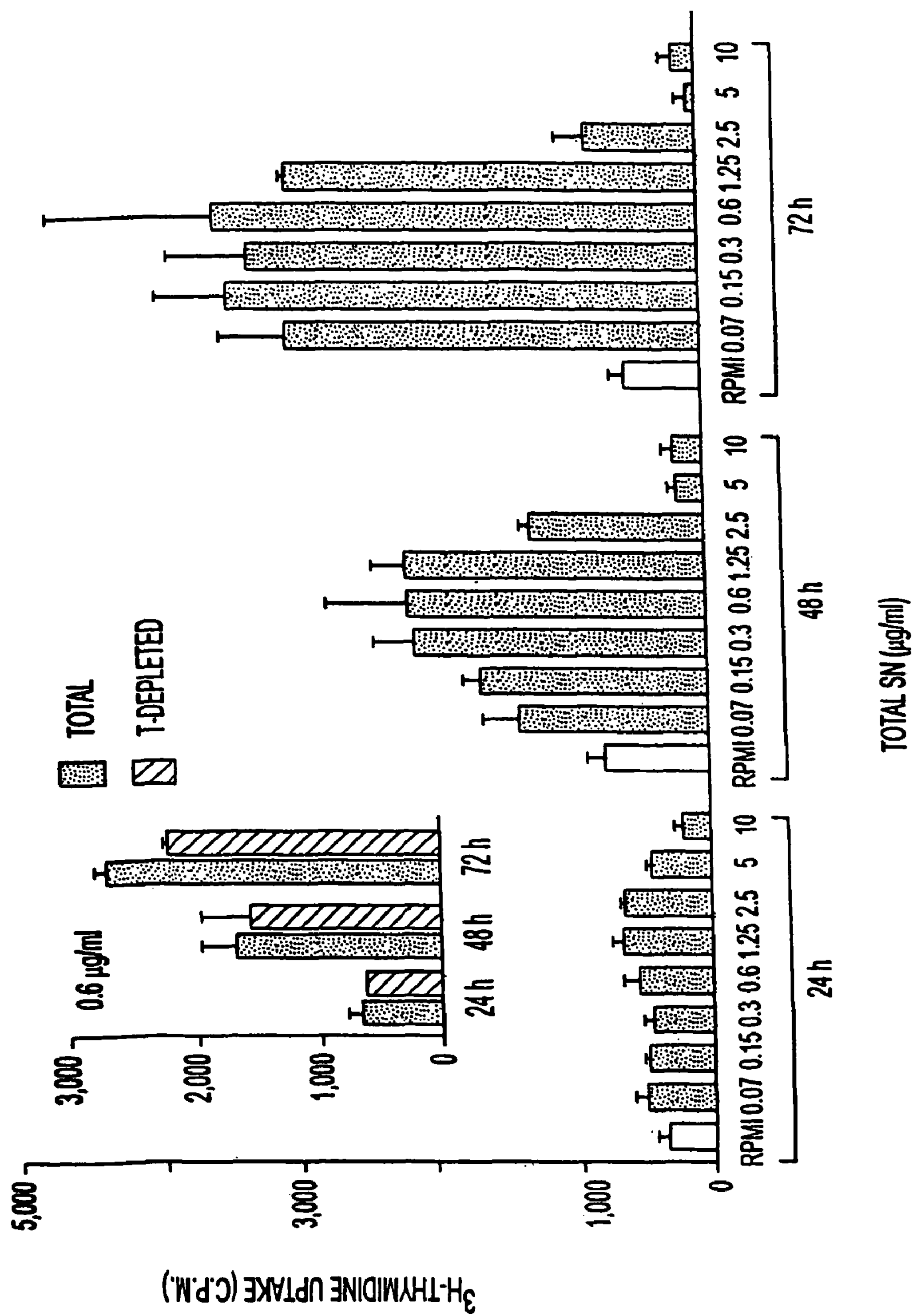
FIG. 1A depicts the proliferative activity of total spleen cells stimulated in vitro by increasing concentrations (below graph) of total proteins from culture supernatants of metacyclic trypomastigotes differentiated in vitro. The inset shows proliferation of total (■) or T cell-depleted (/) splenocytes in the presence of proteins from total culture supernatant c.p.m., counts per minute.

Proliferation is sustained over a 72 h period of culture in a dose dependent manner as shown in FIG. 1*a*. Increasing concentrations (μg protein/ml) of total culture supernatant of in vitro differentiated metacyclic trypomastigotes are shown in this Fig. The inset shows proliferation of total or T-cell depleted splenocytes in the presence of 0.6 μg/ml of total culture supernatant. As for other B-cell mitogens, the same level of proliferation was observed when supernatants were tested on T-cell depleted splenocytes (FIG. 1*a*).

Figure 1B:
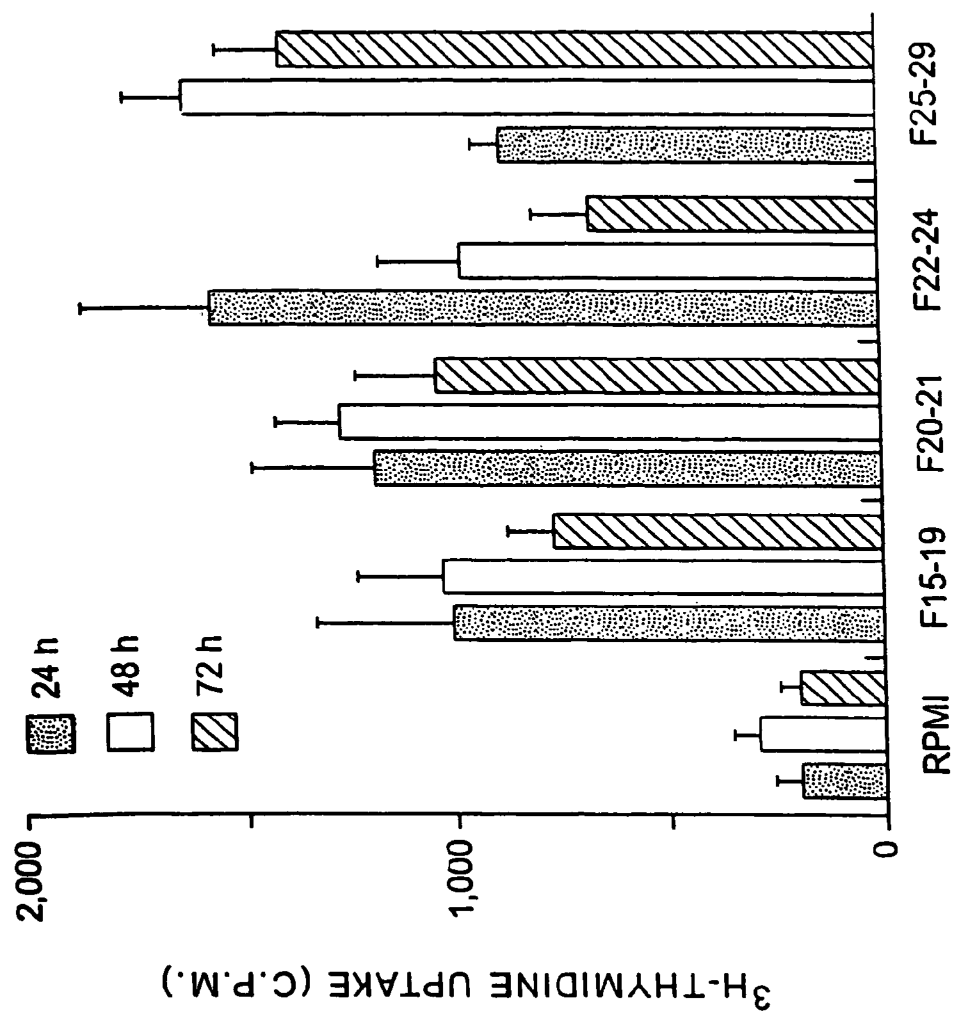
FIG. 1B depicts proliferative activity of total spleen cells stimulated in vitro by HPLC pooled fractions at 24 h (■), 48 h (□) and 72 h (/). $^3$H-thymidine uptake (c.p.m., counts per minute) after 48 h in the presence of concavalin A and lipopolysaccharide was 32,000 and 3,500 counts per minute, respectively. To rule out the possibility of mitogenic effect due to lipopolysaccharide contamination in the samples, proliferation assays were also done using freshly recovered splenocytes from the 'lipopolysaccharide non-responder' mouse strain C3H/He; the same levels of proliferation were obtained.

To identify the molecules responsible for mitogenic activity, the parasite proteins present in the metacyclic culture supernatants were fractionated by HPLC anion-exchanger chromatography, and the resulting fractions were tested as above. Fractions 22-24 (eluted at 368 mM<$NH_4$-acetate<467 mM) showed the highest $^3$H-thymidine uptake at 24 hours. The results are shown in FIG. 1*b*. 0.5 μg/ml of HPLC pooled fractions were resuspended in RPMI.

Previous observations using DEAE-chromatography-purified parasite culture supernatants had shown that a protein fraction of 40-45 kDa was able to induce B-cell activation and proliferation in vivo. The estimation of this range of molecular weight was done more or less 10% and compared with standard molecular weight kit markers commercialized by BioLabs (USA).

Figure 1C:
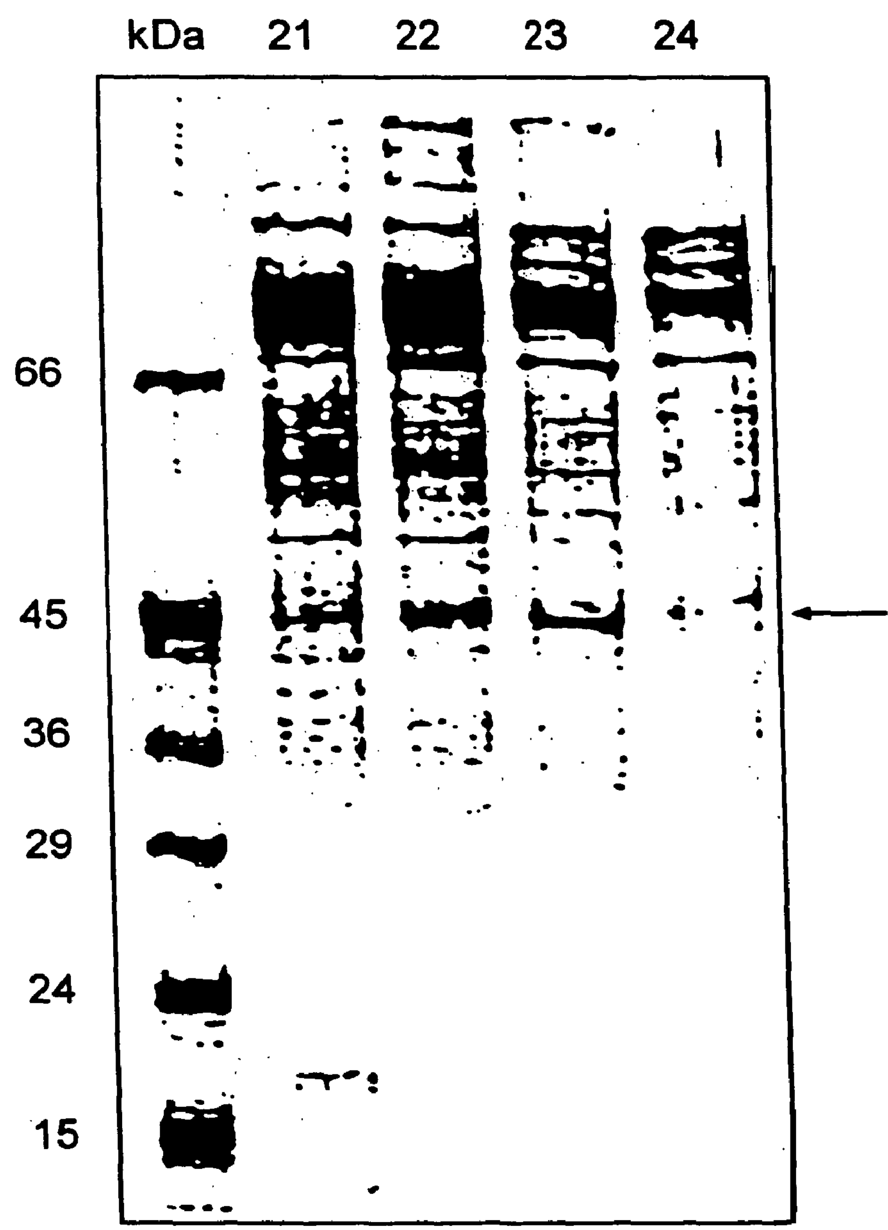
FIG. 1C shows an 8% SDS-PAGE analysis of fractions 21-24 (silver staining). Molecular size markers are shown at the left margin. The arrow corresponds to a 45 kDa band.

SDS-PAGE analysis of the HPLC fractions revealed the presence of a protein with an apparent molecular weight around 45 kDa only in fractions 21-24 as shown in FIG. 1*c*. (8% SDS-PAGE gel of fractions 21 to 24 (silver staining)). The isoelectric point of the protein was estimated between 4.5 and 5.0 by isoelectric focusing. These data indicated that a protein with B-cell mitogenic activity was present in fractions 21-24 eluted from the anionic matrix, and the 45 kDa protein band was thus selected as the main candidate.

To obtain peptide sequences from the 45 kDa protein, which was identified as Tc45, and allow for subsequent PCR-assisted cloning of a gene fragment, the 45 kDa protein band was isolated by SDS-PAGE, and its internal digestion and microsequencing were undertaken. Six peptides were isolated, sequenced, and were shown to have the following sequences: (W)$^{43}$IIk$^{46}$ [SEQ ID NO:18]; I$^{90}$VTGSLP(D)I(S)G$^{100}$ [SEQ ID NO:19]; A$^{183}$TNVPVVLDTPAGLVR$^{198}$ [SEQ ID NO:20]; V$^{241}$DIAFGGNF$^{249}$ [SEQ ID NO:21]; N$^{316}$VVIFGNR$^{323}$ [SEQ ID NO:22], and M$^{338}$ATLYAK$^{344}$ [SEQ ID NO:23]. These sequences are underlined in FIG. 2.

Peptides 4 [SEQ ID NO:21] and 5 [SEQ ID NO:22] were selected for degenerate primer design on the basis of the relatively low level of degeneracy in their corresponding coding sequences. The sequences of these peptides are identified by italic characters in FIG. 2.

Reverse transcription was performed on total RNA from *T. cruzi* trypomastigote forms using reverse degenerate primers for both peptides. The resulting cDNA was then used as a template for PCR amplification. From all possible combinations, when using in the PCR reaction forward primer for peptide 4 (SEQ ID No. 13), reverse primer for peptide 5, and template cDNA synthesized with reverse primer for peptide 5 (SEQ ID No. 12), only one PCR product of 239 bp was shown to contain both primers after cloning and sequencing. The sequence analysis revealed that the fragment contained an unique open reading frame (ORF) flanked by peptides 4 [SEQ ID NO:21] and 5 [SEQ ID NO:22] coded in frame.

To obtain the full sequence of the Tc45 gene, the $^{32}$P-labelled 239 bp PCR product was used as a probe to screen a *Trypanosoma cruzi* clone CL-Brener lambda Fix II genomic library. Four independent positive phages were isolated. Restriction analysis and Southern blot hybridization revealed two types of patterns, each represented by two phages, suggesting that the Tc45 gene is present in at least two copies per haploid genome.

The complete sequence of the Tc45 gene and flanking regions (GenBank accession no. AF195522), revealed an ORF of 423 codons containing all sequenced peptides (FIG. 2) [SEQ ID NO:1]. Computer analysis predicts a 29 amino acid signal peptide [SEQ ID NO: 3] (double arrowed in FIG. 2) suggesting active secretion by *T. cruzi*. This is in agreement with the fact that the protein was purified from culture supernatants. A poly-pyrimidine rich region and probable trans-splice acceptor site is observed 56 and 7 base pairs (bp) upstream of the ATG codon, respectively. Interestingly, an alternative trans-splicing signal is present about 170 bp upstream of the second ATG codon within the coding region, which if used would allow the expression of a truncated, non-secreted protein lacking 69 amino acids, which is SEQ ID No. 4. Polyadenylation may take place at positions 1442 or 1443, which are preceded by repeats of the triplet UUA, a motif found at the 3' end of other *T. cruzi* genes[12,13].

To investigate the genomic organization and transcription of the Tc45 gene, Southern and Northern blot analyses were done. FIG. 4 depicts the results of characterization of rTcPA45 activities. FIG. 4, part a, is an 8% SDS-PAGE gel of rTcPA45 (Coomasie blue staining). Part b depicts the proliferative activity of total splenocytes ($5\times10^4$ cells/well) in the presence of increasing concentrations of rTcPA45 (μg/ml). Part c shows percent racemization of L-proline, D-proline, L-hydroxy-proline, D-hydroxy-proline substrates. Reaction conditions were: 0.2 M Na-acetate/25 mM β-mercaptoethanol buffer, pH6, rTcPA45 (3 μg/ml), 30 min incubation at 37° C. in 500 μl. The reaction was stopped by incubating for 10 min at 80° C. FIG. 4, part d, shows percent inhibition of racemization of 80 mM L-proline in the presence of several inhibitors. Part e shows percent racemization of L-proline (80 mM) as a function of pH (buffers used were 0.2 M: Na-acetate, K-phosphate and Tris-HCl and contained 25 mM β-mercaptoethanol). Reactions were carried out for 30 min at 37° C. and stopped for 5 min at 80° C. All reagents and inhibitors were purchased from Sigma. The shift in optical rotation was measured in a Polarimeter 241 MC (Perkin Elmer).

Figure 3A:
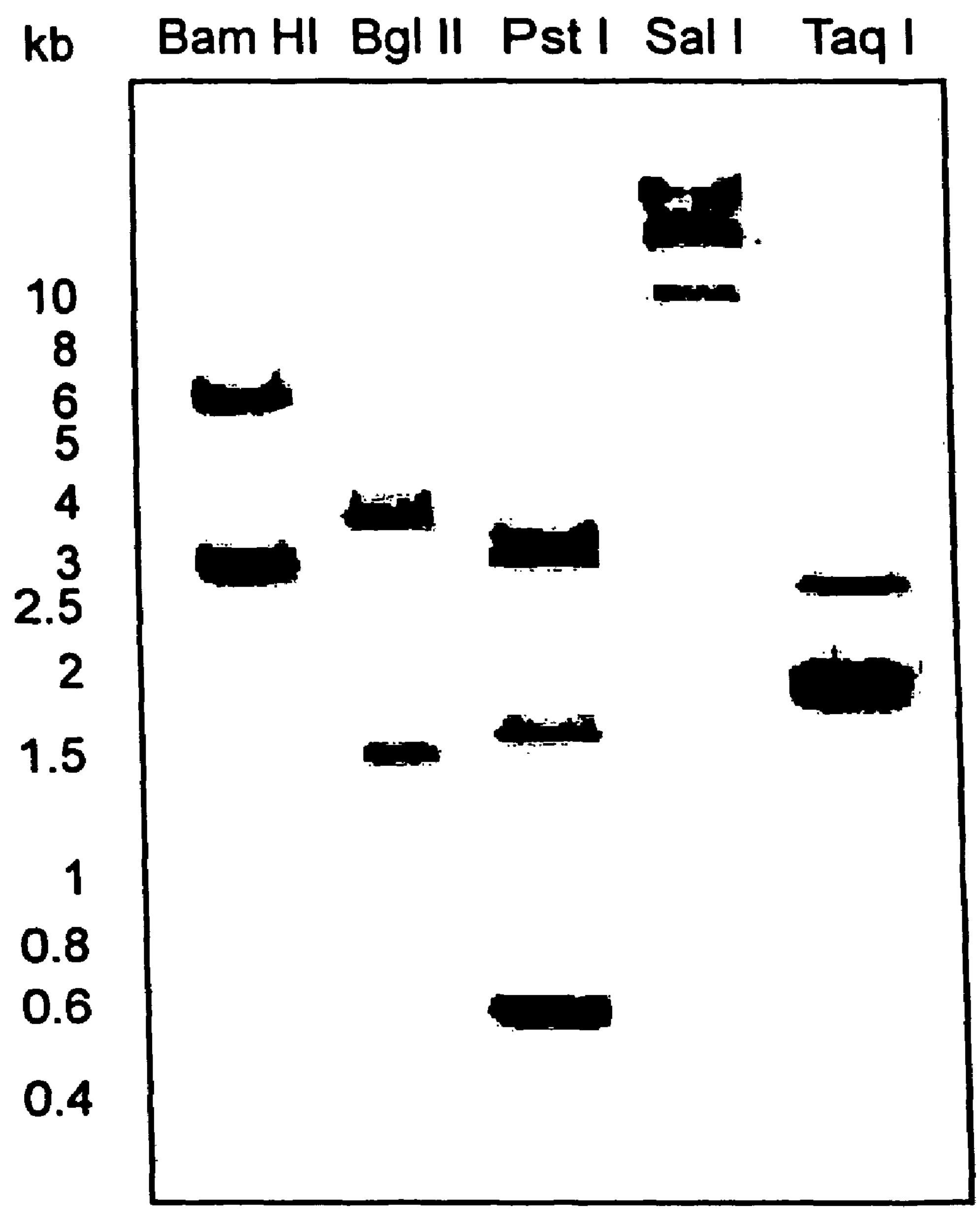
FIG. 3A shows a Southern blot analysis of 5 μg of *T. cruzi* genomic DNA digested with indicated restriction enzymes and hybridized with a $^{32}$P-labeled probe, including the TcPA45 coding sequence, is shown. Molecular weights are indicated.
Figure 3B:
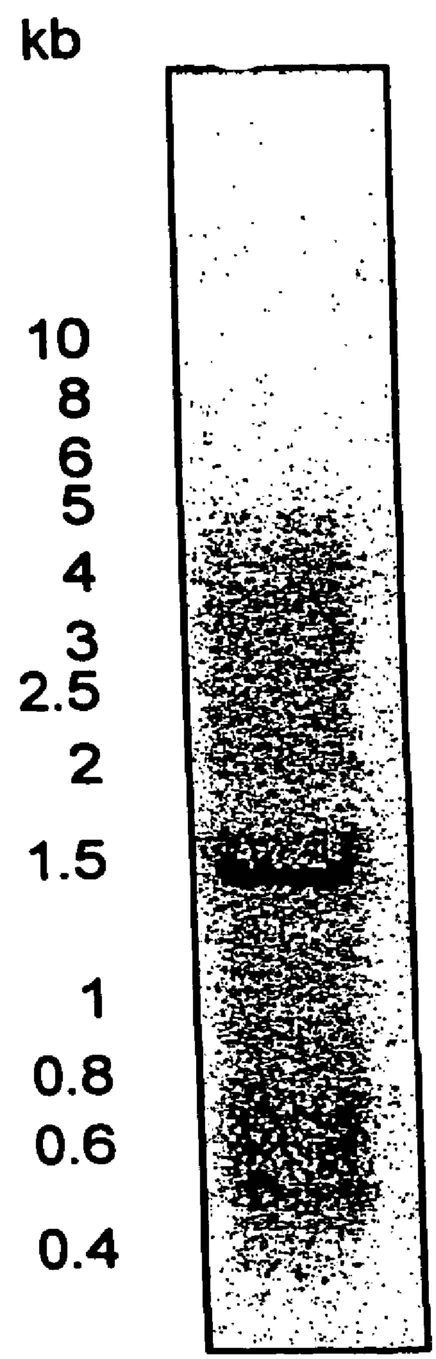
FIG. 3B is a Northern blot analysis of 20 μg of total RNA from epimastigotes forms hybridized with a $^{32}$P-labeled probe as above. Molecular weights [Kb] are indicated.
Figure 3C:
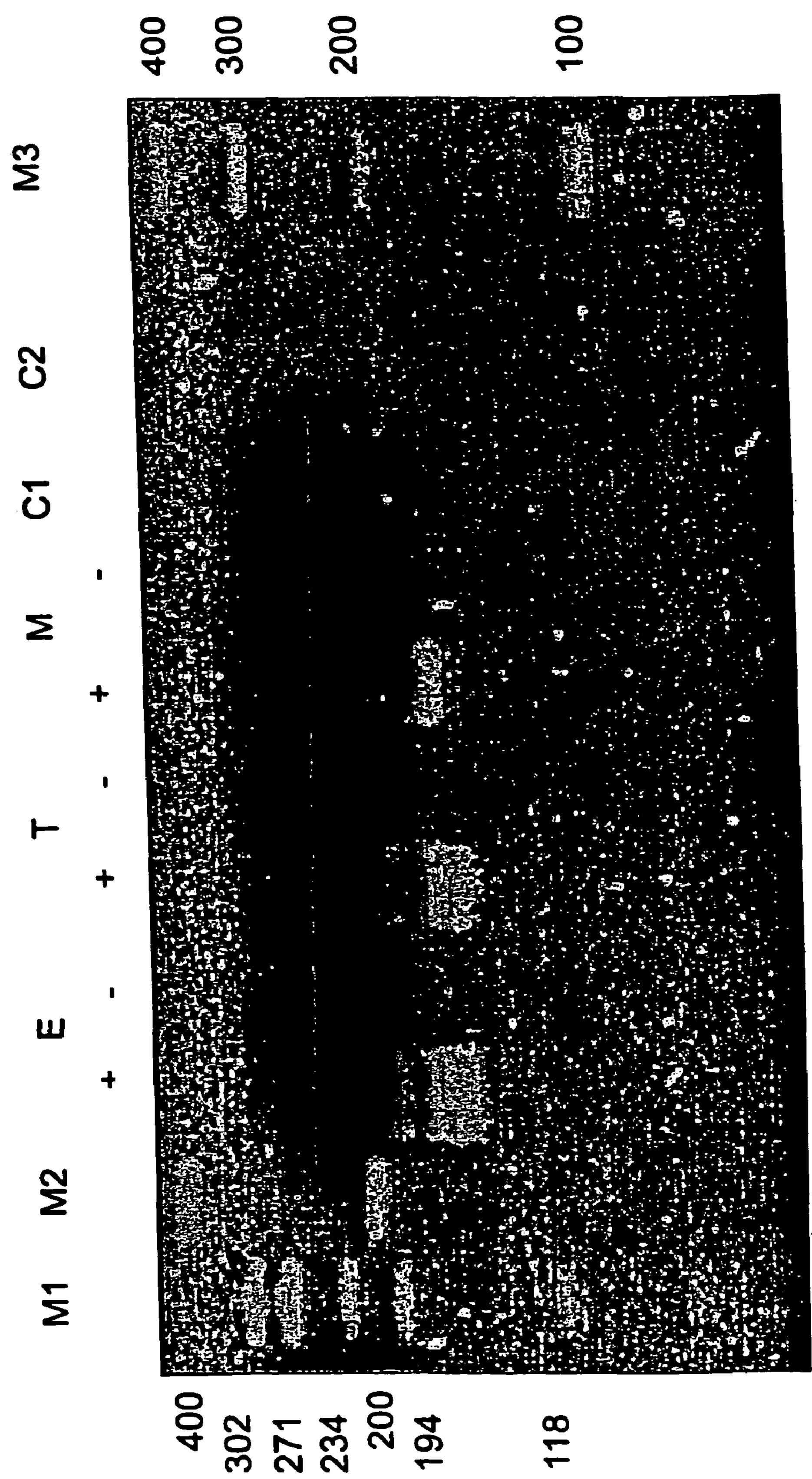
FIG. 3C shows mRNA expression of TcPA4S in different life stages of the parasite, shown by electrophoresis of gene fragments obtained by specific reverse transcription from total parasite RNA followed by PCR amplification using the sequences of the mini-exon (spliced leader) and R-300-45 primers and subsequent amplification of a 170-bp internal fragment. M1, M2 and M3, molecular size markers (sizes, left and right margins) are shown. First-strand cDNA reactions were done in the presence (+) or absence (−) of reverse transcriptase, to exclude the possibility of further PCR amplification of fragments due to genomic DNA contamination, C1 and C2, internal negative (no template) controls; E, epimastigote, T, typomastigote and M, metacyllic.

To investigate the genomic organization and transcription of the Tc45 gene, we used Southern blot analysis; this indicated the presence of two gene copies per haploid genome. There are probably two homologous Tc45 genes (FIG. 3*a*). Digestion with BamHI and BglII producted two hybridizing bands, consistent with the presence of two gene copies, as the probe has neither enzyme restriction site. High-molecular-weight DNA hybridized after probable partial digestion with SalI, consistent with the absence of this site within the coding sequence covered by the probe. Both PstI and TaqI cleaved within the probe and produced more than one hybridizing band per gene copy. Preliminary results indicated that they are located on different chromosomes (data not shown). Northern blot analysis on total RNA from epimastigotes showed a transcript of around 1.5 kb, as expected from the genomic sequence (FIG. 3*b*). We confirmed the presence of the Tc45 mRNA in different parasite forms by reverse transcription PCR using primers specific for the Tc45 gene (FIG. 3*c*). Several point mutations were already identified in the sequence of the putative Tc45-B gene copy representative of the second phage type (FIG. 2), and further transcriptional and functional analyses of the alleles are underway.

To identify homologies with other genes, we compared the Tc45-A gene copy and protein sequence to several databases. There was homology (nucleotide sequence, 57.7%; IDENTITY amino-acid sequence, 52.4% IDENTITY) with the only proline racemase described[14], an intracellular homodimetric protein isolated from *Clostridum sticklandii*. This enzyme catalyzes the interconversion between the L- and D-proline enantiomers, and its reaction mechanism has been studied extensively[14]. There was also homology with the translation of an ORF sequence from *Pseudomonas aeruginosa* in contig 53 of the unfinished *Pseudomonas* genome project (amino-acid sequence, 37.9% IDENTITY; *C. sticklandii* proline racemase and the translation of the *P. aeruginosa* ORF, 47% IDENTITY. The *C. sticklandii* proline racemase active site has been identified[15] and is conserved in the Tc45 protein. Homology with both bacterial proteins started at amino acid 70 of Tc45 (FIG. 2). The presence of the KIIK peptide (FIG. 2, underlining) in the Tc45 protein purified from parasite culture supernatants confirmed the presence of the extra N-terminal portion of the protein released by *T. cruzi* metacyclic forms.

Figure 4A:
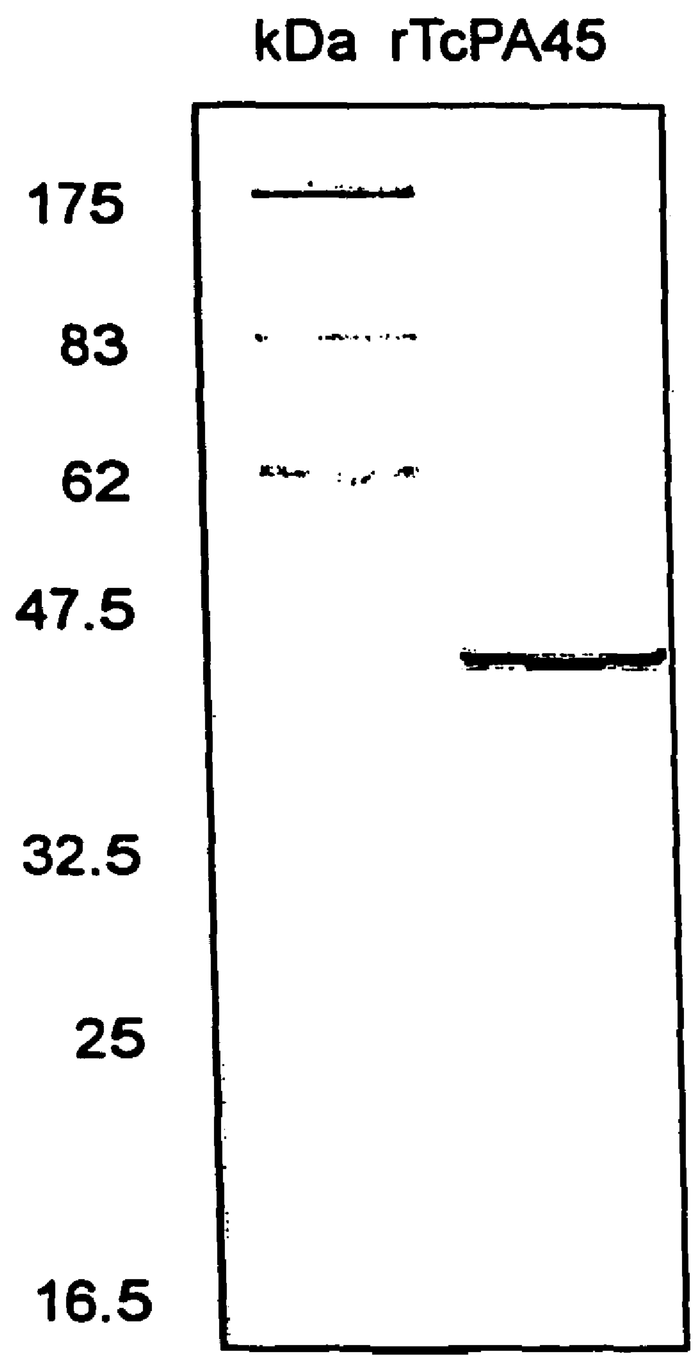
FIG. 4A shows an 8% SDS-PAGE gel of rTcPA45 (Coomasie blue staining).
Figure 4B:
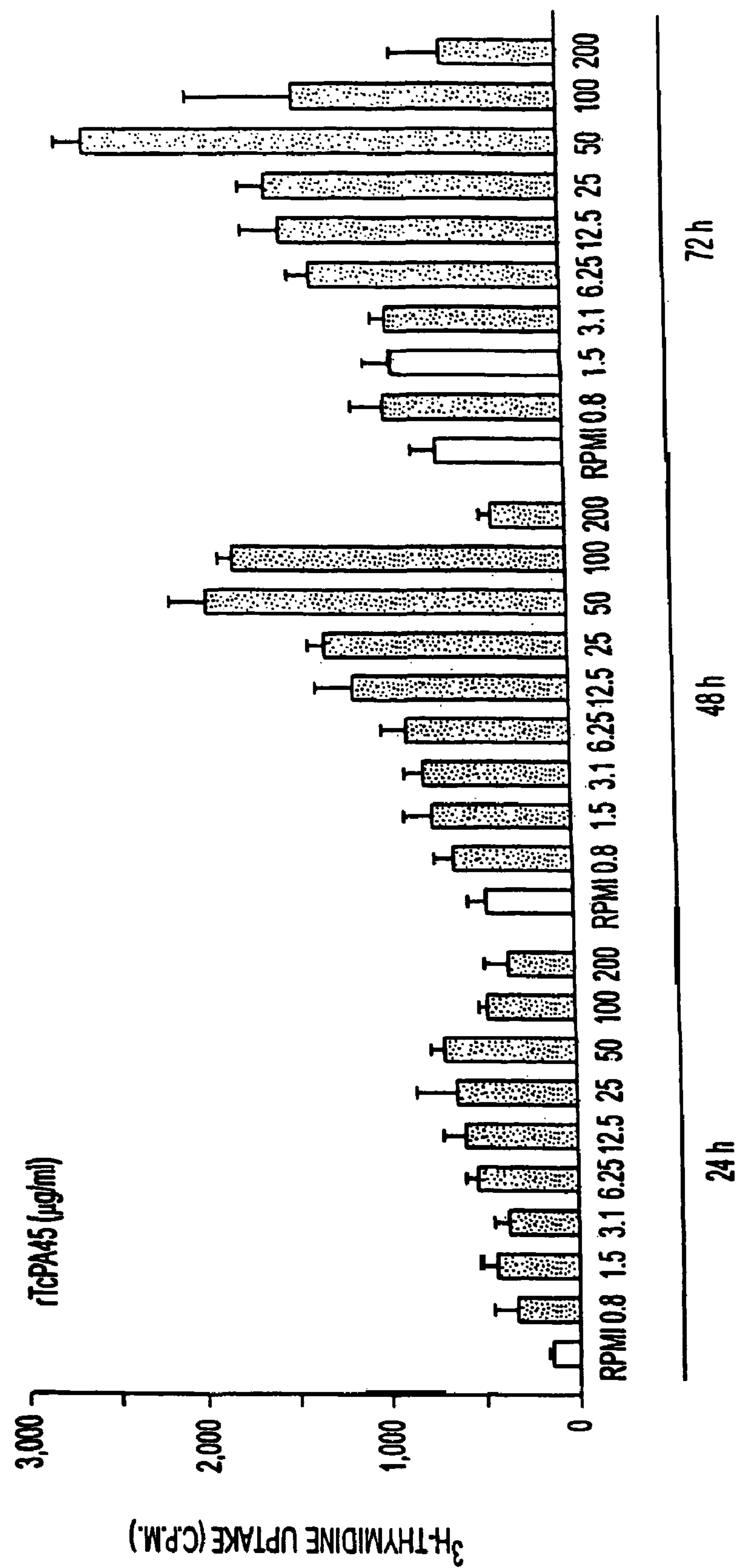
FIG. 4B depicts proliferative activity of total splenocytes ($5\times10^4$ cells/well) in the presence of increasing concentrations of rTcPA45 (μg/ml).

More particularly, the SDS-PAGE analysis of the overexpressed and purified protein is shown in FIG. 4*a*. Using in vitro proliferation assays of naive murine spleen cells, recombinant protein rTc45 was shown to display a similar mitogenic activity to the one observed with the native protein fraction, purified from culture supernatants. Thus, rTcPA45 (for *T. cruzi* polyclonal activator 45) induces spleen lymphocyte proliferation, which increases with time over a 72 h period of culture (FIG. 4*b*). Proliferation is dose dependent, with a bell-shaped response curve (starting from 0.8 μg/ml, and peaking at 50 μg/ml) typical of all mitogens described to date. rTcPA45 is indeed a T cell-independent polyclonal activator of B lymphocytes, as shown by the magnitude and increase of the proliferative response of total spleen lymphocytes obtained from athymic mice compared with the response of lymphocytes from euthymic individuals (FIG. 9). Injection of 50 μg rTcPA45 in vivo induced a 2 fold increase in spleen cell numbers by day 4, accompanied by an increase in numbers of immunoglobulin (Ig)-secreting B cells of the IgM, IgG2a, IgG2b and IgG3 isotypes (2.5 fold to 100×), while showing a complete lack of rTcPA45-specific Ig-secreting B cells, indicating the polyclonal B-cell mitogenicity of the protein (data not shown).

Injection of 50 μg of rTcPA45 in vivo induces a 2-fold increase in spleen cell numbers by day 7 accompanied by 2.5 to 4 fold increase in numbers of Ig-secreting B cells of IgM, IgG2a, and IgG2b isotypes, while showing a complete lack of Ig-secreting B cells directed to TcPA45 demonstrating the polyclonal B-cell mitogenicity of the protein as shown in Example 10, Table I.

Figure 4C:
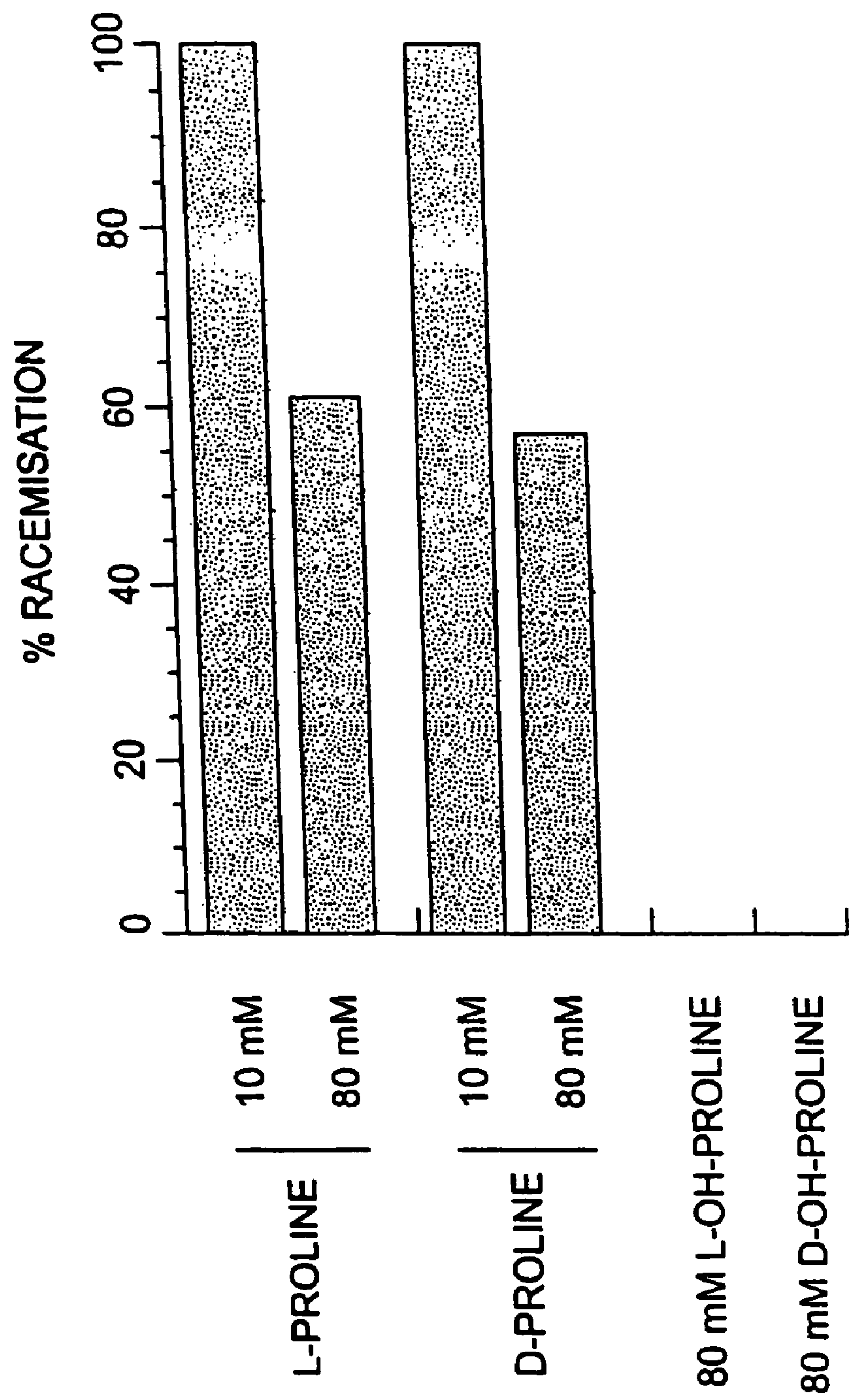
FIG. 4C depicts percent racemisation of L-proline, D-proline, L-hydroxy-proline, D-hydroxy-proline substrates. Reaction conditions are 0.2 M Na-acetate/25 mM β-mercaptoethanol buffer, pH6, rTcPA45 (3 μg/ml), 30 min incubation at 37° C. in 500 μl. The reaction was stopped by incubating for 10 min at 80° C.

To confirm that the TcPA45 protein is indeed a proline racemase, in vitro biochemical assays were performed to measure the shift in optical rotation of either L- or D-proline substrates. As can be seen in FIG. 4*c*, rTcPA45 racemises both L- and D-proline, but not L- or D-hydroxy-proline, nor any other natural L-amino acids. Such rTcPA45 racemase activity is co-factor independent, notably of pyridoxal phosphate, and thus closely resembles the *C. sticklandii* proline racemase[14].

Figure 4D:
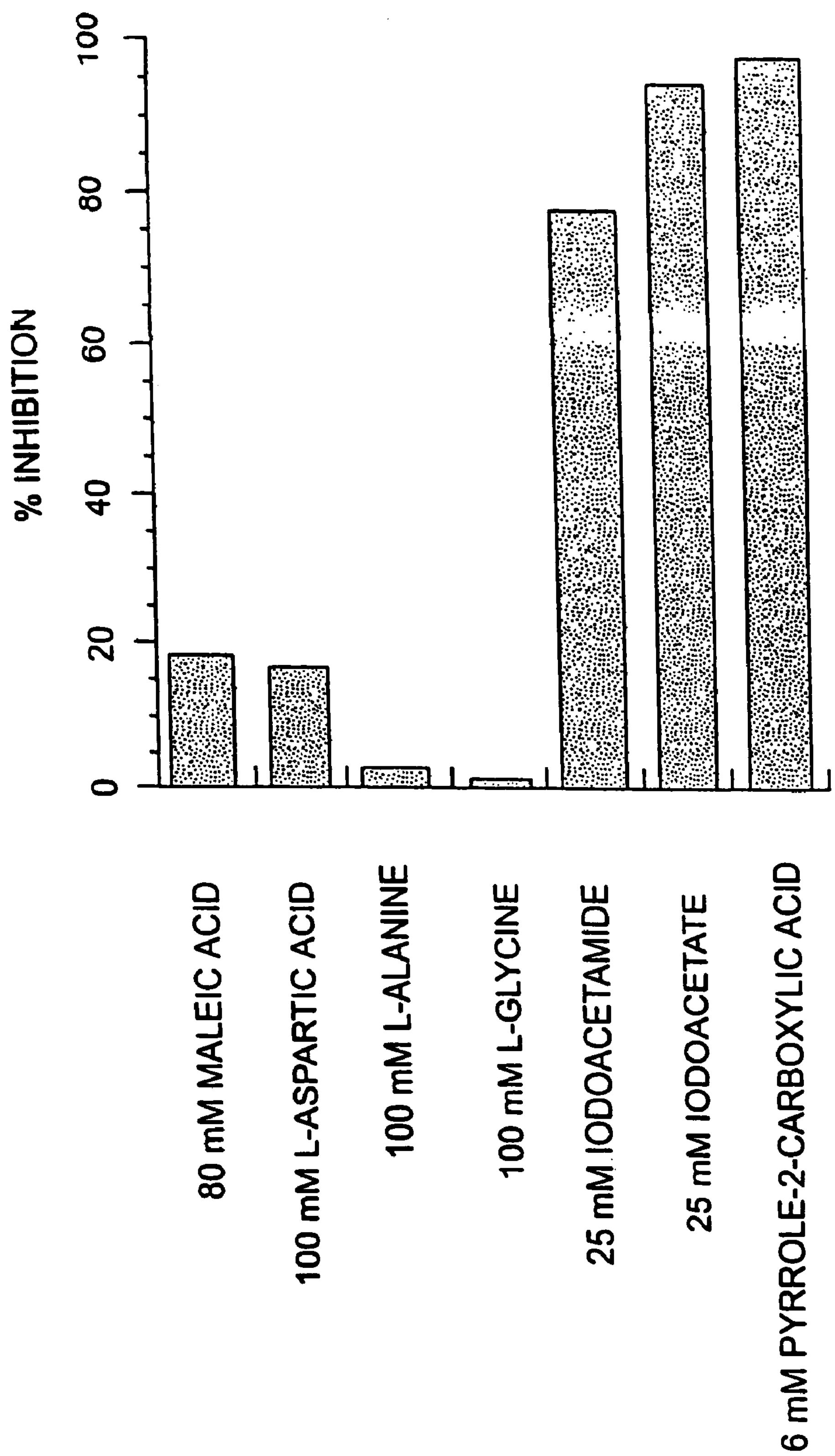
FIG. 4D depicts percent inhibition of racemization of 80 mM L-proline in the presence of several inhibitors.

Furthermore, the rTcPA45 enzymatic activity is inhibited to different extents by the presence of previously described inhibitors[14], such as maleic acid, iodoacetamide, iodoacetate, and pyrrole-2-carboxylic acid (FIG. 4*d*). Interestingly, rTcPA45 proline racemase activity is maximal at pH 6 (FIG. 4*e*), two units lower than that of the bacterial enzyme[14]. The optimal temperature for enzymatic activity is 37° C., and the enzyme is inactivated by 10 min heating at 80° C. (data not shown).

To analyze the cellular localization of the parasite TcPA45, we used immunofluorescence experiments with a polycyclonal serum raised against rTcPA45. Whereas serum from chronically infected mice stained typomastigote cells uniformly, rTCPA45 specific antibodies stained mostly the cytoplasm of epimastigote forms but not the nucleus or the kinetoplast (FIG. 10*a*). In vitro-differentiated metacyclic forms showed a less in tense and more diffuse pattern of cytoplasmic staining than did epimastigotes. However, bloodstream trypomastigote forms were strongly labeled at the flageliar pocket and the anterior and posterior ends of the parasite, and lightly along the flagellum and cytoplasm. These experiments substantiate the hypothesis that *T. cruzi* has an intracellular form of the proline racemase and the secretion might only take place in the infective forms. Western blot analysis of cell extracts of the parasite confirmed that the TcPA45 protein was present in different developmental stages (FIG. 10*b*). We detected a TcPA45 protein around 39 kDa in molecular mass in epimastigotes (non-infective insect forms) and 41.S kDa in infective metacyclic trypomastigotes, compared with the computer-predicated molecular masses of 43.4 kDa and 38 kDa, respectively, for a secreted and a non-secreted form of the protein (FIG. 10*c*). Western blot analysis of the non-infective epimastigote cell stage showed Tc45 proline racemase mostly in the soluble cellular fraction, only weakly in the cellular insoluble fraction and absent from culture medium (FIG. 10*d*).

To confirm the relationship, if any, between the enzymatic and the mitogenic activities of rTcPA45, we used in vitro proliferation assays with active rTcPA45 and different forms of the inactivated enzyme. Unexpectedly, mitogenic activity was abolished when rTcPA45 was inactivated by being heated or by long storage at 4° C., or whenever enzymatic inhibition was achieved by pre-incubation of the protein with specific (pyrrole-2-carboxylic acid) or nonspecific (iodoacetamide and iodoacetate) inhibitors of proline racemase (FIG. 11*a*). Mitogenic activity was also affected considerably by supplementation of the cultures with increasing amounts of L- or D-proline, in a dose-dependent manner, indicating that competitive inhibition occurred in the presence of specific substrates (FIG. 11*b*). There was no cell proliferation when lymphocytes were cultured in the presence of 50 mM L- or D-proline alone (FIG. 11*b*). Furthermore, mitogenic activity due to another B-cell mitogen was unaffected by the inhibitors or substances (data not shown). Although the antibodies against TcPA45 raised against the recombinant protein were not able to inhibit racemization or to neutralize mitogenic activity in vitro, and thus cannot be used to support a link between these activities, the results indicate that a free and intact active site of the rTcPA45 protein is necessary to allow mitogenicity.

This is the first description of an amino acid racemase gene in an eukaryotic organism. Thus, this invention relates to the biochemical isolation, cloning, and molecular characterization of a B-cell mitogen released by *Trypanosoma cruzi*. Unexpectedly, this is also the first description of a racemase in a parasite.

In bacteria, amino acid racemases are cytoplasmic proteins participating in metabolic processes or in the synthesis of post-translationally modified peptides[16]. It is known that *T. cruzi* can use L-proline as a major carbon source[17], possibly through a D-proline intermediate[18]. In this case, however, one might expect to find a cytosolic proline racemase. Indeed, we have identified a cytosolic proline racemase in epimastigote forms of *T. cruzi* as shown in FIGS. 6 and 10(*b*). This racemase presents a molecular weight of 38 kd in 10% SDS Page by using a standard molecular weight kit commercialized by BioLABS (USA). The estimation of the molecular weight is done more or less 10% around 38 kda. It is well established that proteins bearing D-amino acids are highly resistant to eukaryotic proteases. Thus, it might also be possible that the parasite uses the racemization mechanism during metacyclogenesis to synthesize and express, on its surface, proteins containing D-proline, therefore ensuring a certain degree of resistance to host-induced proteolytic mechanisms during cell invasion. Interestingly, *T. cruzi* differentiation from epimastigote to trypomastigote is induced in the presence of L-proline at pH 6 in the insect's gut[19] as well as during in vitro metacyclogenesis[11], and the proline racemase activity of the TcPA45 protein might be involved in this process.

FIG. 2 shows homology between the Tc45 protein (Tc) and the bacterial proline racemases *Clostridium sticklandii* (Cs) and *Pseudomonas aeruginosa* (Pa). Identical residues appear in bold characters; the computer-predicted signal peptide is indicated by a double arrow; peptide sequences obtained by microsequencing appear underlined; peptides used for designing degenerate primers appear in italic characters. Proline racemase active sites are boxed; dashes indicate gaps generated for best fit.

The homology of TcPA45 protein sequence with the *Clostridium sticklandii* proline racemase starts at amino acid 70 (second methionine in the ORF of TcPA45 gene) allowing the speculation that *T. cruzi* has acquired an extra 70 amino acid sequence N-terminal to the ancestral proline racemase (comprising a signal peptide for secretion) gaining the ability to produce either a cytosolic or a secreted form of the protein by differential trans-splicing of the mRNA. In addition, this process might be differentially regulated at distinct developmental stages of the parasite. In this context, it could then be hypothesised that epimastigote forms produce a cytosolic protein, while infective trypomastigotes secrete the same protein that activates B-cell polyclonal responses.

Interestingly, the disruption of alanine racemase and the D-amino acid aminotransferase genes of *Listeria monocytogenes* results in the inability of the bacteria to grow within the eukaryotic host cells[24]. Both these gene products are involved in the synthesis of D-alanine that is required for the production of a mucopeptide component of the cell walls of virtually all bacteria. It remains to be investigated whether or not such bacterial molecules are B-cell mitogens. Accordingly, working with random amino acid polymers, Sela and co-workers have established that multichain polypeptides composed of D-amino acids induce antibody responses in a T-cell independent manner[25,26], a property that can be interpreted as equivalent to B-cell mitogenicity[27,28]. Resistance of such D-amino acid peptides to degradation by host enzymes[29] could also explain the persistence of polyclonal responses (and immunosuppression)[30], even if parasite production of the mitogen would be transient at the start of infection.

Thus, novel polynucleotides corresponding to the Tc45 gene from CL strain (representative of lineage *T. cruzi* II) *T. Cruzi* have been isolated and sequenced. The presence of the Tc45 gene has also been demonstrated in a representative strain of another major lineage of *T. cruzi* [strain DM 28c, lineage *T. cruzi* I]. For a review on recommendations on *T. cruzi* strain nomenclature see: Mem. Institut. OSW. Cruz, Vol. 94, Suppl. 1, page 429-432, 1999. These polynucleotides include SEQ ID NOS: 7, 8, 9, 10, and 11. By "polynucleotides" according to the invention is meant the sequences referred to as SEQ ID NOS: 7, 8, 9, 10, and 11, and the complementary sequences and/or the sequences of polynucleotides that hybridize to the referred sequences under conditions of moderate stringency. The moderate stringency conditions are defined as washing conditions in 2×SSC at 55° C., and hybridization operated in 5×SSC at 55° C.

By "active molecule" according to the invention is meant a molecule capable of inhibiting the activity of the purified recombinant or native polypeptide as defined in the present invention.

Thus, the polynucleotides of SEQ ID NO: 7 and its fragments can be used as probes or to select nucleotide primers notably for an amplification reaction, such as the amplification reactions further described. PCR is described in the U.S. Pat. No. 4,683,202 granted to Cetus Corp. The amplified fragments may be identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic acid probes the polynucleotides derived from SEQ ID NO: 7 and its fragments, oligonucleotides that are complementary to these polynucleotides or fragments thereof, or their amplification products themselves.

Amplified nucleotide fragments are useful as probes in hybridization reactions in order to detect the presence of one polynucleotide according to the present invention or in order to detect the presence of a parasite of *T. Cruzi* strain carrying genes encoding racemase activity, in a biological sample. This invention also provides the amplified nucleic acid fragments ("amplicons") defined herein above. These probes and amplicons can be radioactively or non-radioactively labeled, using for example enzymes or fluorescent compounds.

Preferred nucleic acid fragments that can serve as primers according to the present invention are the following:

```
5'TTICCRAADATIACIACGTT3'             [SEQ ID NO: 12]

5'ATHGCITTYGGIGGIAAYTTT3'            [SEQ ID NO: 13]

5'TTICCRAADATIACIACGTT3'             [SEQ ID NO: 14]

5'CTCTCCCATGGGGCAGGAAAAGCTTCTG3'     [SEQ ID NO: 15]

5'CTGAGCTCGACCAGATCTATCTGC3'.        [SEQ ID NO: 16]
```

These sequences are degenerate primers designed from the peptide sequence of Tc45. These primers can also be used as oligonucleotide probes to specifically detect a polynucleotide according to the invention.

Other techniques related to nucleic acid amplification can also be used alternatively to the PCR technique. The Strand Displacement Amplification (SDA) technique (Walker et al., 1992) is an isothermal amplification technique based on the ability of a restriction enzyme to cleave one of the strands at a recognition site (which is under a hemiphosphorothioate form), and on the property of a DNA polymerase to initiate the synthesis of a new strand from the 3N OH end generated by the restriction enzyme, and on the property of this DNA polymerase to displace the previously synthesized strand being localized downstream.

The SDA amplification technique is more easily performed than PCR (a single thermostated water bath device is necessary), and is faster than the other amplification methods. Thus, the present invention also comprises using the nucleic acid fragments according to the invention (primers) in a method of DNA or RNA amplification, such as the SDA technique. The polynucleotides of SEQ ID NO: 7 and its fragments, especially the primers according to the invention, are useful as technical means for performing different target nucleic acid amplification methods, such as:

TAS (Transcription-based Amplification System), described by Kwoh et al. in 1989;

SR (Self-Sustained Sequence Replication), described by Guatelli et al. in 1990;

NASBA (Nucleic acid Sequence Based Amplification), described by Kievitis et al. in 1991; and TMA (Transcription Mediated Amplification).

The polynucleotides of SEQ ID NO: 7 and its fragments, especially the primers according to the invention, are also useful as technical means for performing methods for amplification or modification of a nucleic acid used as a probe, such as:

LCR (Ligase Chain Reaction), described by Landegren et al. in 1988 and improved by Barany et al. in 1991, who employ a thermostable ligase;

RCR (Repair Chain Reaction), described by Segev et al. in 1992;

CPR (Cycling Probe Reaction), described by Duck et al. in 1990; and

Q-beta replicase reaction, described by Miele et al. in 1983 and improved by Chu et al. in 1986, Lizardi et al. in 1988, and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

Nucleic acid probes according to the present invention are specific to detect a polynucleotide of the invention. By "specific probes" according to the invention is meant any oligonucleotide that hybridizes with the polynucleotide of SEQ ID NO: 7, and which does not hybridize with unrelated sequences. Preferred oligonucleotide probes according to the invention are SEQ ID NOS:12, 13, 14, 15, and 16.

In a specific embodiment, the purified polynucleotides according to the present invention encompass polynucleotides having at least 80% identity in their nucleic acid sequences with polynucleotide of SEQ ID NO: 7 or fragments thereof. By percentage of nucleotide identity according to the present invention is intended a percentage of identity between the corresponding bases of two homologous polynucleotides, this percentage of identity being purely statistical and the differences between two homologous polynucleotides being located at random and on the whole length of said polynucleotides. The calculation was made according to the software GCG and the program "gap."

The oligonucleotide probes according to the present invention hybridize specifically with a DNA or RNA molecule comprising all or part of the polynucleotide of SEQ ID NO: 7 under stringent conditions. As an illustrative embodiment, the stringent hybridization conditions used in order to specifically detect a polynucleotide according to the present invention are advantageously the following:

Prehybridization and hybridization are performed as follows in order to increase the probability for heterologous hybridization:

The prehybridization and hybridization are done at 50° C. in a solution containing 5×SSC and 1×Denhardt's solution.

The washings are performed as follows:

2×SSC at 60° C. 3 times during 20 minutes each.

The non-labeled polynucleotides or oligonucleotides of the invention can be directly used as probes. Nevertheless, the polynucleotides or oligonucleotides are generally labeled with a radioactive element ($^{32}P$, $^{35}S$, $^{3}H$, $^{125}I$) or by a non-isotopic molecule (for example, biotin, acetylaminofluorene, digoxigenin, 5-bromodesoxyuridin, fluorescein) in order to generate probes that are useful for numerous applications. Examples of non-radioactive labeling of nucleic acid fragments are described in the French Patent No. FR 78 10975 or by Urdea et al. or Sanchez-Pescador et al. 1988.

Other labeling techniques can also be used, such as those described in the French patents 2 422 956 and 2 518 755. The hybridization step may be performed in different ways (Matthews et al. 1988). A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

Advantageously, the probes according to the present invention can have structural characteristics such that they allow signal amplification, such structural characteristics being, for example, branched DNA probes as those described by Urdea et al. in 1991 or in the European Patent No. 0 225 807 (Chiron).

In another advantageous embodiment of the present invention, the probes described herein can be used as "capture probes", and are for this purpose immobilized on a substrate in order to capture the target nucleic acid contained in a biological sample. The captured target nucleic acid is subsequently detected with a second probe, which recognizes a sequence of the target nucleic acid that is different from the sequence recognized by the capture probe.

The oligonucleotide fragments useful as probes or primers according to the present invention can be prepared by cleavage of the polynucleotide of SEQ ID NO: 7 by restriction enzymes, as described in Sambrook et al. in 1989. Another appropriate preparation process of the nucleic acids of the invention containing at most 200 nucleotides (or 200 bp if these molecules are double-stranded) comprises the following steps:

Synthesizing DNA using the automated methods, such as beta-cyanethylphosphoramidite described in 1986;

cloning the thus obtained nucleic acids in an appropriate vector; and purifying the nucleic acid by hybridizing to an appropriate probe according to the present invention.

A chemical method for producing the nucleic acids according to the invention, which have a length of more than 200 nucleotides (or 200 bp if these molecules are double-stranded), comprises the following steps:

Assembling the chemically synthesized oligonucleotides, which can have different restriction sites at each end;

cloning the thus obtained nucleic acids in an appropriate vector; and purifying the nucleic acid by hybridizing to an appropriate probe according to the present invention.

The oligonucleotide probes according to the present invention can also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in European patent application No. 0 713 016, or PCT Application No. WO 95 33846, or also PCT Application No. WO 95 11995 (Affymax Technologies), PCT Application No. WO 97 02357 (Affymetrix Inc.), and also in U.S. Pat. No. 5,202,231 (Drmanac), said patents and patent applications being herein incorporated by reference.

The present invention also pertains to a family of recombinant plasmids containing at least a nucleic acid according to the invention. According to an advantageous embodiment, a recombinant plasmid comprises a polynucleotide of SEQ ID NO: 7 or nucleic acid fragment thereof. More specifically, the following plasmids are part of the invention:

DH5[alpha]-pTc45 MIT (1335 bp) and

Dh5[α]-pTc45 MIT (239 bp).

A suitable vector for the expression in bacteria, and in particular in *E. coli*, is pET-28 (Novagen), which allows the production of a recombinant protein containing a 6×His affinity tag. The 6×His tag is placed at the C-terminus or N-terminus of the recombinant polypeptide. The purified racemase is obtained by expression in *E. coli* transformed with pET-28 containing the insert of the plasmid corresponding to the CNCM No. I-2344 deleted of the sequence of the signal peptide as shown on SEQ ID NO: 9 and including the six C terminal histidine residues. The expression of pET-28 with the insert was induced by IPTG (1 millimolar) overnight at 20° C. resulting in a soluble recombinant racemase according to the invention. This racemase has a molecular weight of 45 kda in 8% SDS PAGE gel (see FIG. 4*a*) compared with standard molecular weight kit markers (BioLABS). After lysis of the bacterial cells by a French Press, followed by centrifugation (2000 g during 15 minutes), the recombinant protein was purified from the supernatant using nickel IMAC chromatography. (commercialized by PHARMACIA) and eluted in 0.5 molar imidazol buffer. The yield is between 10 to 40 mg of protein for one liter of bacterial culture at 1.OD density. The OD at the beginning of the induction of the expression in the recombinant bacterial was comprised between 0.6 to 1 OD. In the culture conditions as disclosed above, the majority of the recombinant protein produced is in a soluble form and they are not favorable for the expression of the proteins of the bacterial host. The estimation of the molecular weight of the purified recombinant protein is done more or less 10% around 45 kda.

The polypeptides according to the invention can also be prepared by conventional methods of chemical synthesis, either in a homogenous solution or in solid phase. As an illustrative embodiment of such chemical polypeptide synthesis techniques, the homogenous solution technique described by Houbenweyl in 1974 may be cited.

The polypeptides of the invention are useful for the preparation of polyclonal or monoclonal antibodies that recognize the polypeptides (SEQ ID NOS: 1, 2, 3, and 4) or fragments thereof. The monoclonal antibodies can be prepared from hybridomas according to the technique described by Kohler and Milstein in 1975. The polyclonal antibodies can be prepared by immunization of a mammal, especially a mouse or a rabbit, with a polypeptide according to the invention, which is combined with an adjuvant, and then by purifying specific antibodies contained in the serum of the immunized animal on a affinity chromatography column on which has previously been immobilized the polypeptide that has been used as the antigen.

Consequently, the invention is also directed to a method for detecting specifically the presence of a polypeptide according to the invention in a biological sample. The method comprises:

a) bringing into contact the biological sample with an antibody according to the invention; and b) detecting antigen-antibody complex formed.

Also part of the invention is a diagnostic kit for in vitro detecting the presence of a polypeptide according to the present invention in a biological sample. The kit comprises:

a polyclonal or monoclonal antibody as described above, optionally labeled; and a reagent allowing the detection of the antigen-antibody complexes formed, wherein the reagent carries optionally a label, or being able to be recognized itself by a labeled reagent, more particularly in the case when the above-mentioned monoclonal or polyclonal antibody is not labeled by itself.

Indeed, the monoclonal or polyclonal antibodies according to the present invention are useful as detection means in order to identify or characterize a *T. Cruzi* strain carrying TC45 genes.

The invention also pertains to:

A purified polypeptide or a peptide fragment having at least 10 amino acids, which is recognized by antibodies directed against a polynucleotide or peptide sequence according to the invention.

A polynucleotide comprising the full length coding sequence of the Tc45 gene sequence according to the invention.

A monoclonal or polyclonal antibody directed against a polypeptide or a peptide fragment encoded by the polynucleotide sequences according to the invention.

A method of detecting the presence of parasite harboring the polynucleotide sequences according to the invention in a biological sample comprising:

a) contacting DNA or RNA of the biological sample with a primer or a probe according to the invention, which hybridizes with a nucleotide sequence;

b) amplifying the nucleotide sequence using said primer or said probe; and c) detecting the hybridized complex formed between said primer or probe with the DNA or RNA.

A kit for detecting the presence of a parasite harboring the polynucleotide sequences according to the invention in a biological sample, comprises:

a) a polynucleotide probe according to the invention; and b) reagents necessary to perform a nucleic acid hybridization reaction.

A method of screening active molecules for the treatment of the infections due to a parasite, comprises the steps of:

a) bringing into contact a parasite containing the polynucleotide sequences according to the invention with the molecule; and b) measuring an activity of the active molecule on the parasite.

An in vitro method of screening for an active molecule capable of inhibiting a polypeptide encoded by the polynucleotide sequences according to the invention, wherein the inhibiting activity of these molecules is tested on at least said polypeptide, comprises the steps of:

a) providing a polypeptide according to the invention;

b) contacting the active molecule with said polypeptide;

c) testing the capacity of the active molecules, at various concentrations, to inhibit the activity of the polypeptide; and d) choosing the active molecule that provides an inhibitory effect of at least 80% on the activity of the said polypeptide.

A test for screening the inhibiting activity of a molecule, for example, a new substrate analogue or a new antiparasitic agent, can comprise the following steps:

A suitable test for testing an active molecule inhibiting the polypeptide according to the invention is performed as follows:

The recombinant amino acid purified or native racemase is diluted in sodium acetate buffer or Tris or phophate on Hepes buffer at 3 micrograms per 500 microliters in the presence of 20 millmolar of beta mercepto ethanol and 10 to 80 millimolar of L or D substrate and containing various concentrations of active molecule to be tested. This reaction is incubated for 30 minutes at 37° C. and stopped by heating at 80° C. Variations in optical rotation are measured by a polarimeter.

Another embodiment of this invention provides a method for inhibiting the activity of a parasite in vivo. The method comprises administering to a host a parasite mitogen, which is capable of exhibiting a protective effect, a curative effect, or preventing transmission of a parasite in the host. The parasite mitogen is administered to the host in an amount sufficient to prevent or at least inhibit infection in vivo or to prevent or at least inhibit spread of the parasite in vivo. These effects are achieved by administering the parasite mitogen to the host in a sub-mitogenic amount, which is preferably sufficient to induce a protective response against the parasite in the host.

The parasite mitogen employed in this invention is distinguished from an "antigen", which is a substance that induces an immune response, such as a complete antigen that both induces an immune response and reacts with the product of the response, or an incomplete antigen (hapten) that cannot induce an immune response by itself, but can react with the products of an immune response when complexed to a complete antigen (carrier). The parasite mitogens of the present invention are thus unlike antigens, which require processing and presentation, such as (1) uptake of the antigen by antigen presenting cells (APCs); (2) internalization of the antigen in intracellular vesicles; (3) intracellular processing, which may include the unfolding of a protein and/or partial proteolysis, with generation of immunogenic peptides; (4) binding of peptides to class II MHC molecules to form a bimolecular complex recognized by T cells; and (5) transport to, and display of, the complex on the surface of APCs. In addition, the parasite mitogens employed in this invention do not require activation of the APCs as manifested by the expression of: (1) adhesion molecules that promote the physical interaction between APCs and T cells; (2) membrane bound growth/differentiation molecules (co-stimulators) that promote T cell activation; or (3) soluble cytokines, such as IL-1 and TNF, as is required in the process for presenting antigens.

The mitogen employed in this invention is also distinguished from a "superantigen", which is a substance that can stimulate all of the T cells in an individual that express a particular set or family of $V_\beta$T cell receptor genes. Superantigens are typically bacterial and viral products, and can either be soluble or cell-bound. They do not require degradation to peptides. Superantigens are typically presented to the T cell receptor (TCR) on MHC molecules; however, they do not require processing by antigen presenting cells (APC), as do antigens, in order to be presented.

Thus, used herein, the term "mitogen" refers to a polyclonal activator that has the capacity to bind to and to trigger proliferation or differentiation of B lymphocytes, T lymphocytes, or mixtures thereof. Lymphocyte proliferation or transformation is the process whereby new DNA synthesis and cell division takes place in lymphocytes after a stimulus of some type, resulting in a series of changes. The lymphocytes increase in size, the cytoplasm becomes more extensive, the nucleoli are visible in the nucleus, and the lymphocytes resemble blast cells. The term blast transformation is also sometimes applied to this process. Mitogens can induce proliferation in normals cells in culture. Activation of the lymphocytes thus can be characterized by transformation of the lymphocytes into blast cells, synthesis of DNA, cell division, increased production of immunoglobulins, or increased cytokine production. More particularly, the mitogens employed in this invention can stimulate whole classes of lymphocytes in this manner, and not just clones of particular specificity. The mitogens employed in this invention function, therefore, in a manner similar to the effects produced by lipopolysaccharide (LPS) on B cells, or lectins, concanavalin A (ConA), and phytohemagglutinin (PHA) on T cells.

With these phenomena in mind, the expression "parasite mitogen", as used herein, means at least one protein or polypeptide found in a parasite, wherein the protein or polypeptide is capable of provoking non-specific polyclonal activation of B lymphocytes, T lymphocytes, or mixtures thereof, in an in vitro culture of the lymphocytes in the manner similar to that just described. The protein or polypeptide comprising the parasite mitogen can be in glycosylated or non-glycosylated form. The parasite mitogen can be in natural or recombinant form.

The term "recombinant" as used herein means that a protein or polypeptide employed in the invention is derived from recombinant (e.g., microbial or mammalian) expression systems. "Microbial" refers to recombinant proteins or polypeptides made in bacterial or fungal (e.g., yeast) expression systems. As a product, "recombinant microbial" defines a protein or polypeptide produced in a microbial expression system, which is essentially free of native endogenous substances. Proteins or polypeptides expressed in most bacterial cultures, e.g. *E. coli*, will be free of glycan. Proteins or polypeptides expressed in yeast may have a glycosylation pattern different from that expressed in mammalian cells.

The parasite mitogen employed in this invention can be in isolated or purified form. The terms "isolated" or "purified", as used in the context of this specification to define the purity of protein or polypeptide compositions, means that the protein or polypeptide composition is substantially free of other proteins of natural or endogenous origin and contains less than about 1% by mass of protein contaminants residual of production processes. Such compositions, however, can contain other proteins added as stabilizers, excipients, or co-therapeutics. The parasite is isolated if it is detectable as a single protein band in a polyacrylamide gel by silver staining.

Evaluation of lymphocyte proliferation can be quantitated in an assay of proliferative activity. For example, a radiolabelled precursor of DNA (usually tritiated thymidine) can be added to a culture medium and the amount of radioactivity incorporated into the cells subsequently detected. A suitable assay involves the in vitro culture of a lymphocyte population in the presence or absence of a mitogen for various periods of time. The changes induced in the stimulated groups are compared with changes in unstimulated cell populations. Radiolabelled amino acids are convenient as they provide a means of quantitating the changes in a simple, reproducible manner. Thus, as used herein, the expression "assay of proliferative activity" means the following assay:

Assay of Proliferative Activity

In vitro proliferation is accomplished using freshly recovered splenocytes from BALB/c mice seeded at a density of $5\times10^4$ cells/well and incubated for 24, 48 and 72 h with increasing concentrations of total parasite supernatants or recombinant TcPa45 protein or other mitogen (0.07-200 μg/ml) with 0.5 μg/ml of the HPLC fractions, or with the conventionally used mitogens concanavalin A (10 μg/ml) and lipopolysaccharide (5 μg/ml) in 5% FCS in RPMI-1640 complete medium. T-cell depletion is accomplished by incubating freshly recovered spleen cells for 30 min. at 37° C. in the presence of monoclonal antibodies against Thy 1.2 and rabbit complement (Cedarlane, Le Perray en Yvelines, France). Analysis of proliferative activity of total splenocytes ($5\times10^4$ cells/well) in the presence of 50 μg/ml enzymatically active rTcPA45 or other mitogen is also compared with the proliferation obtained using the same amounts of rTcPA45 protein or other mitogen lacking racemase activity (by heating for 10 min. at 30° C. or by long term storage at 4° C.). Inhibition of proliferation is obtained by adding to the splenocyte cultures 50 μg/ml rTcPA45 or other mitogen pre-incubated for 10 min. at 37° C. with 1 mM inhibitor, either specific (pyrrole-2-carboxylic acid) or nonspecific (iodoacetamide or iodoacetate). Competitive assays of proliferative activity by 50 μg/ml rTcPA45 or other mitogen are done by adding increasing concentrations of specific substrates i.e., proline racemase substrates (L- or D-proline) for the mitogen rTcPA45 ranging from 3 mM to 50 mM. Controls include the incubation of splenocytes ($5\times10^4$ cells/well) with substrate alone, i.e., 50 mM L- or D-proline in RPMI medium alone for prline racemase. Cultures are collected after a 16-hour pulse or 1 μCi/well $^3$H-thymidine uptake was determined in a beta-plate liquid scintillation counter (LKB-Wallac, Orsay, France). All data points are obtained in triplicate and the corresponding standard deviation is calculated.

This assay of proliferative activity is used to determine whether a substance is a parasite mitogen. This assay is also used to determine a sub-mitogenic amount of the parasite mitogen. The results obtained in a typical assay of proliferative activity for two different mitogens, A and B, are depicted in FIG. 13, which is not based on data actually obtained in this invention, but which is merely included for illustrative purposes to show the effects produced by mitogens after lymphocyte activation.

Moreover, while the identification of a parasite or virus mitogen for use in the invention is accomplished by use of the assay of proliferative activity, it will be understood that the results obtained with this assay can be followed by other methods of measuring activation of lymphocytes, such as by measuring immunoglobulin production and/or carrying out immunoglobulin specificity assays. The Elispot assay described hereinafter can be used for this purpose.

As used herein, the term "sub-mitogenic amount" means an amount of the parasite mitogen, which is less than an amount of the parasite mitogen that produces an increase in lymphocyte proliferation in the assay of proliferative activity. Thus, the sub-mitogenic amount can be easily determined by carrying out the assay of proliferative activity at several low dosages of the parasite mitogen and noting the dosage at which proliferative activity first increases. The sub-mitogenic amount is an amount below the dosage at which proliferative activity first increases.

The sub-mitogenic amount must also be sufficient to induce protective immunity against the parasite in a host to which the sub-mitogenic amount of the parasite mitogen is administered. As used herein, the term "protective immunity" refers to an adaptive (specific) immune response characterized by specificity and memory in the host to which the sub-mitogenic amount of the parasite mitogen is administered. The adaptive immune response once stimulated by an invading parasite will remember and respond more rapidly to infection so that no disease will occur or any disease that occurs following infection will be less severe as compared to a similar infection without prior immunization according to the invention. Thus, the protective immunity imparted by the method of the invention imparts protection from disease, particularly infectious disease, as evidenced by the absence of clinical indications of disease, or as evidenced by absence of, or reduction in, determinants of pathogenicity, including the absence or reduction in persistence of the infectious parasite or virus in vivo, and/or the absence of pathogenesis and clinical disease, or diminished severity thereof, as compared to individuals not treated by the method of the invention.

The determination of a sub-mitogenic amount can readily be understood by reference to FIG. 13, which depicts two dose-response curves for two different hypothetical mitogens A and B. A sub-mitogenic amount of mitogen A would be an amount below about dose "Y" in FIG. 13, while a sub-mitogenic amount of mitogen B would be an amount below dosage "X" in FIG. 13.

The TcPA45 protein of the invention is referred to as a "parasite mitogen" in a functional sense in that it is capable of activating a non-specific polyclonal response in lymphocytes in the assay of proliferative activity. TcPA45 itself might not be a mitogen, but may act through racemization or by binding to host molecules, which would be the primary mitogens. Regardless, the non-specific lymphocyte activation by TcPA45 in amounts exceeding a sub-mitogenic amount would insure evasion of the parasite at the very beginning of infection.

The evasiveness and diversity of parasites has made definitive treatment difficult. Presented here are methods and agents for preventing the spread of parasitic and viral infections in a host, such as a human. Examples of microorganisms against which the methods and agents of the invention are effective are the following.

TABLE 2

Immune dysfunctions observed after mitogen-induced polyclonal activation following infectious processes

| Microorganism | Target lymphocytes | Acute or progressive dysfunctions |
|---|---|---|
| *Actinomyces viscousus* | B | Immunosuppression |
| African Swine Fever virus | B | Immunosuppression |
| *Ascaris* | B | IgE secretin, allergy, cerebral granuloma |
| *Borrelia burgdorferi* | B | Autoimmune arthritis |
| *Candida albicans* | B | Granuloma formation, immunosuppression |
| *Chlamidia trachomatis* | B | Lymphocytosis, autoimmunity |
| *Entamoeba histolytica* | T | Immunosuppression, disabling colitis, liver abscess |
| *Escherichia coli* | B | Toxic shock syndrome, meningitis, neurological and systemic symptoms |
| *Leishmania donovani, L major* | B | Immunosuppression, autoimmunity |
| *Listeria monocytogenes* | B and T | Meningitis, immune complex formation and immunosuppression |
| *Mycobacterium tuberculosis* | T | Immunosuppression and autoimmune arthritis |
| *Plasmodium chabaudi, P. yoellii* | T | Immunosuppression, autoimmunity |
| *P. falciparum* | B and T | Immunosuppression, autoimmunity |
| *Salmonella paratyphi, S. typhimurium* | B | Lethal scepticemia, vascular myocardial injuries, immunosuppression, autoimmunity |
| *Schistosoma mansoni, S. hematobium* | B | Immunosuppression, megasyndromes, granuloma |
| *Staphylococcus aureaus* | B | Toxic shock syndrome, mastitis, immunosuppression |
| *Streptococcus intermedius, S. mutans* | B | Toxic shock syndrome, immunosuppression |
| *S. pyogenes* | B and T | Immunosuppression, autoimmunity |
| *Toxocara canis* | B | Eosinophilia, lung damage, ocular granuloma, vasculitis |
| *Toxoplasma gondii* | B and T | Encephalitis, myocarditis, immunosuppression |
| *Trypanosoma brucei* | B | Immunosuppression, glomerulonephritis and brain lesions |
| *T. congolense* | B | Immunosuppressin |
| *T. cruzi* | B and T | Hypergammaglobulinemia, immunosuppression, autoimmune myocarditis, megasyndromes |

These and other substances employed as mitogens in this invention are of parasitic or viral origin, are of natural or recombinant form, and are similarly capable of producing a polyclonal response in unselected lymphocytes in the assay of proliferative activity. More particularly, while this invention has been described with reference to parasite mitogens, it is equally applicable to viral antigens. Indeed, by substituting "viral mitogen" for the expression "parasite mitogen" and "virus" for "parasite" in the foregoing description, the full scope of the subject invention will be understood. In addition, the parasite mitogens employed in this invention will exemplified with reference to the mitogen TcPA45 protein of *T. cruzi*. While the parasite mitogen TcPA45 is also a racemase, it will be understood that the parasite mitogens and virus mitogens can be employed in this invention may or may not possess racemase activity.

Following are additional examples of microorganisms against which the vaccination strategy of the invention is applicable: Infection with Epstein-Barr, influenza, herpes, and sendai viruses; non- or poorly pathogenic viruses, such as and African swine fever virus; and murine leukaemia virus. Both T-cell-dependent and independent polyclonal B-cell activation have also been described for a variety of protozoan parasite infections, and these infections can also be prevented or abated by the vaccination strategy of this invention. These microorganisms include *Plasmodium berghei, P. yoellii, P. chabaudi., P. falciparum* and *P. vivax.*

In practicing the method of the invention, the parasite or viral mitogen is administered to a host using one of the modes of administration commonly employed for administering drugs to humans and other animals. Thus, for example, the parasite or viral mitogen can be administered to the host by the oral route or parenterally, such as by intravenous or intramuscular injection. Other modes of administration can also be employed, such as intrasplenic, intradermal, and mucosal routes. For purposes of injection, the mitogens described above can be prepared in the form of solutions, suspensions, or emulsions in vehicles conventionally employed for this purpose.

It will be understood that the parasite and viral mitogens can be used in combination with other parasite or viral mitogens or other prophylactic or therapeutic substances. For example, mixtures of different parasite mitogens or mixtures of different viral mitogens can be employed in the method of the invention. Similarly, mixtures of parasite and viral mitogens can be employed in the same composition. The parasite and viral mitogens can also be combined with other vaccinating agents for the corresponding disease, such microbial immunodominant, immunopathological and immunoprotective epitope-based vaccines or inactivated attenuated, or subunit vaccines. The parasite and viral mitogens can even be employed as adjuvants for other immunogenic or vaccinating agents.

The parasite or viral mitogen is employed in the method of the invention in an amount sufficient to provide an adequate concentration of the drug to prevent or at least inhibit infection of the host in vivo or to prevent or at least inhibit the spread of the parasite or virus in vivo. The amount of the mitogen thus depends upon absorption, distribution, and clearance by the host. Of course, the effectiveness of the parasite or viral mitogen is dose related. The dosage of the parasite or viral mitogen should be sufficient to produce a minimal detectable effect, but the dosage should be less than the dose that activates a non-specific polyclonal lymphocyte response as measured by the assay of proliferative activity previously described.

The dosage of the parasite or viral mitogen administered to the host can be varied over wide limits. The parasite or viral mitogen can be administered in the minimum quantity, which is therapeutically effective, and the dosage can be increased as desired up the maximum dosage tolerated by the patient.

The parasite or viral mitogen can be administered as a relatively high sub-mitogenic amount, followed by lower maintenance dose, or the parasite or viral mitogen can be administered in uniform dosages.

The dosage and the frequency of administration will vary with the parasite or viral mitogen employed in the method of the invention. In the case of the TcPA45 parasite mitogen, the sub-mitogenic amount administered to a human can vary from about 50 ng per Kg of body weight to about 1 μg per Kg of body weight, preferably about 100 ng per Kg of body weight to about 500 ng per Kg of body weight. Similar dosages can be employed for the other parasite and viral mitogens employed in this invention but optimum amounts can be determined with a minimum of experimentation using conventional dose-response analytical techniques or by scaling up from studies based on animal models of disease.

The term "about" as used herein in describing dosage ranges means an amount that is equivalent to the numerically stated amount as indicated by the induction of protective immunity in the host to which the parasite or viral mitogen is administered, with the absence or reduction in the host of determinants of pathogenicity, including an absence or reduction in persistence of the infectious parasite or virus in vivo, and/or the absence of pathogenesis and clinical disease, or diminished severity thereof, as compared to individuals not treated by the method of the invention.

The dose of the parasite or viral mitogen is specified in relation to an adult of average size. Thus, it will be understood that the dosage can be adjusted by 20-25% for patients with a lighter or heavier build. Similarly, the dosage for a child can be adjusted using well known dosage calculation formulas.

The parasite or viral mitogen can be used in therapy in the form of pills, tablets, lozenges, troches, capsules, suppositories, injectable in ingestable solutions, and the like in the treatment of cytopatic and pathological conditions in humans and susceptible non-human primates and other animals.

Appropriate pharmaceutically acceptable carriers, diluents, and adjuvants can be combined with the parasitic and viral mitogens described herein in order to prepare the pharmaceutical compositions for use in the treatment of pathological conditions in animals. The pharmaceutical compositions of this invention contain the active mitogens together with a solid or liquid pharmaceutically acceptable nontoxic carrier. Such pharmaceutical carriers can be sterile liquids, such as water an oils, including those of petroleum, animal, vegetable, or synthetic origin. Examples of suitable liquids are peanut oil, soybean oil, mineral oil, sesame oil and the like. Water is a preferred carrier when the pharmaceutical composition is administered intravenously. Physiological solutions can also be employed as liquid carriers, particularly for injectable solutions.

The ability of the vaccines of the invention to induce protection in a host can be enhanced by emulsification with an adjuvant, incorporation in a liposome, coupling to a suitable carrier, or by combinations of these techniques. For example, the vaccines of the invention can be administered with a conventional adjuvant, such as aluminum phosphate and aluminum hydroxide gel. Similarly, the vaccines can be bound to lipid membranes or incorporated in lipid membranes to form liposomes. The use of nonpyrogenic lipids free of nucleic acids and other extraneous matter can be employed for this purpose.

Suitable pharmaceutical excipients include starch, glucose, lactose, sucrose, gelatine, malt, rice, flour, chalk, silica gel, magnesium carbonate, magnesium stearate, sodium stearate, glycerol monstearate, talc, sodium chloride, dried skim milk, glycerol, propylene glycol, water, ethanol, and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. The pharmaceutical compositions contain an effective therapeutic amount of the parasite or viral mitogen together with a suitable amount of carrier so as to provide the form for proper administration to the host.

The host or patient can be an animal susceptible to infection by the parasite or virus, and is preferably a mammal. More preferably, the mammal is selected from the group consisting of a human, a dog, a cat, a bovine, a pig, and a horse. In an especially preferred embodiment, the mammal is a human.

Another aspect of the invention includes administering nucleic acids encoding parasite and/or viral mitogens with or without carrier molecules to an individual. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids encoding parasite and/or viral mitogens, naked or encapsulated, directly to tissues and cells without the need for production of encoded proteins prior to administration. The technology is based on the ability of these nucleic acids to be taken up by cells of the recipient organism and expressed to produce a mitogen to which the recipient's immune system responds. Such nucleic acid vaccine technology includes, but is not limited to, delivery of naked DNA and RNA and delivery of expression vectors encoding the parasite or viral mitogen. Although the technology is termed "vaccine", it is equally applicable to immunogenic compositions that do not result in a complete protective response. Such partial-protection-inducing compositions and methods are encompassed within the present invention.

Although it is within the present invention to deliver nucleic acids encoding the parasite or viral mitogens as naked nucleic acids, the present invention also encompasses delivery of nucleic acids as part of larger or more complex compositions. Included among these delivery systems are viruses, virus-like particles, or bacteria containing the nucleic acids encoding the parasite or viral mitogen. Also, complexes of the invention's nucleic acids and carrier molecules with cell permeabilizing compounds, such as liposomes, are included within the scope of the invention. Other compounds, such as molecular vectors (EP 696,191, Samain et al.) and delivery systems for nucleic acid vaccines are known to the skilled artisan and exemplified in, for example, WO 93 06223 and WO 90 11092, U.S. Pat. No. 5,580,859, and U.S. Pat. No. 5,589,466 (Vical patents), which are incorporated by reference herein, and can be made and used without undue or excessive experimentation.

Results indicate that intramuscular DNA vaccination protocols using pcDNA3 vector containing the TcPA45 gene, with or without the fragment encoding the signal peptide, are able to induce a decrease of 85% in parasitemia levels after challenge with infective forms of the parasite. Moreover, even higher levels of parasitemia control resulted when sub-mitogenic doses of the active rTcPA45 protein were injected intraperitoneally 2 weeks before infective challenge. These observations support the use of this molecule as a drug and/or immunomodulator target.

This invention further contemplates:

1. Any molecular modification of the gene or a fragment of the gene encoding for a racemase/mitogen that leads to the inhibition of the expression of the protein by the parasite or virus (gene knock out), and further utilization of parasites or viruses lacking those activities in vivo aiming at immunoprotective responses.

2. Any molecular modification of the gene or a fragment of the gene encoding for a racemase/mitogen that leads to the hyperexpression of the protein by the parasite or virus (gene transgenesis), and further utilization of the parasite or virus to produce high amounts of the protein aiming at producing high amounts of the native protein.
3. Any molecular modification of the gene or a fragment of the gene encoding for a racemase/mitogen that leads to an attenuation of parasite or virus infectivity, or interaction with a host cell, and further injection of the parasites or viruses in vivo aiming at immunoprotective responses.
4. Any molecular modification (for instance directed mutagenesis) of the protein or of its active site that leads to the inhibition of its enzymatic or its mitogenic activity and further injection of mutated parasites or viruses in vivo aiming at immunoprotective responses.
5. Use of any molecular or biochemical modification of the enzymatic activity of the racemase (inhibition of the active site) aiming at developing specific immunotherapy.
6. Any molecule or compound that inhibits the enzymatic activity of the protein aiming at developing a drug against parasite or virus infection or specific treatment of parasitic or viral disease.

An example of the application of this technology to the invention follows:

The catalytic site of TcPA45 protein responsible for racemase activity is identified by the boxed region in FIG. 2. The catalytic site comprises the amino asides acids SPCTGT (SEQ ID NO: 27). Inhibition of racemase activity, and the consequent loss in infectivity, can be accomplished by altering this catalytic site in the protein or altering the corresponding nucleotides in the gene encoding the protein. A target for alteration would be the cysteine residue. For example, changing the cysteine residue to serine does not significantly alter the charge on the molecule, but diminishes racemase activity. The catalytic site can be altered in other ways, such as by the addition, deletion, or substitution of another moiety for one of the moieties in the protein or the nucleic acid encoding the protein so that secondary and tertiary structures are not materially altered, binding subunits are not affected, but racemase activity is diminished or totally lost.

Plasmids containing the polynucleotides from *T. Cruzi* have been deposited at the Collection Nationale de Cultures de Microorganismes ("C.N.C.M.") Institut Pasteur, 28, rue du Docteur Roux, 75724 Paris Cedex 15, France, as follows:

| Plasmid | Accession No. | Deposit Date |
|---|---|---|
| DH5α-pTc45MIT (239 bp) | I-2221 | Jun. 9, 1999 |
| DH5α-pTc45MIT (1335 bp) | I-2344 | Oct. 29, 1999. |

This invention will now be described with reference to the following Examples.

Example 1

Mice and Parasites

*Trypanosoma cruzi* clone CL Brener was used throughout this work. Epimastigotes were maintained by weekly passage in liver infusion tryptose medium. In vitro metacyclogenesis was performed in a protein free defined medium at 27° C., as previously described[11]. Male euthymic or athymic BALB/c mice 8 weeks of age were purchased from Charles River Laboratories (Saint Aubin les Elbeuf, France). Male C3H/Hel mice 8 weeks of age from our animal facilities were also used.

Example 2

Protein Fractionation 40 liters of culture supernatants from metacyclic forms, maintained for an additional 96 h at 37° C., were concentrated by vacuum dialysis and dialyzed against buffer A. HPLC was performed using a weak anion exchanger column POROS HQ-10 (Perspective Biosystems) at a flow rate of 1 ml/min according to the following program: a) 10 min with buffer A; b) 30 min linear gradient from buffer A to B; c) 5 min linear gradient from buffer B to C; and d) 5 min with buffer C. One ml fractions were collected, frozen at −80° C., lyophilized and reconstituted in $H_20$ or in non-supplemented RPMI medium for in vitro proliferation assays. (Buffers used: A: 5 mM $NH_4$-acetate, pH 8. B: 1M $NH_4$-acetate, pH 8. C: 1M NaCl/1 M $NH_4$-acetate, pH 8). Fractions 1 ml in volume were collected, frozen at −80° C., lyophilized and reconstituted in water or in non-supplemented RPMI medium for in vitro proliferation assays. SDS-PAGE analysis used standard techniques.

Example 3

Generation of Peptides and Amino Acid Sequence Analysis

HPLC fractions 22 and 23 were pooled and fractionated by 8% SDS-PAGE. After amino black staining, the 45 kDa protein band was cut out, in-gel digested with trypsin, and submitted to reverse phase HPLC to separate peptides. Automated Edman degradation sequence analysis was performed in the Laboratoire de Microséquençage de Protéines of the Pasteur Institut.

Example 4

RNA Preparation, Reverse Transcription, PCR, and Cloning

RNA was extracted from trypomastigote forms obtained from Vero cells, using TRIzol LS reagent (Gibco) following manufacturer's instructions. Two μg from this RNA were reverse transcribed in 20 μl with Superscript II (Gibco) using anti-sense degenerate primer 5'TTICCRAADATIACIACGTT3' [SEQ ID NO: 12] designed from peptide 5.

PCR reaction was performed on 5 μl of cDNA using Taq polymerase (Perkin Elmer) or Pfu DNA polymerase (Stratagene). The following PCR conditions and primers were used: 1. TcPA45 gene fragment (239 bp) 30 s at 94° C., 45 s at 45° C., 30 s at 72° C. for 30 cycles followed by 10 min at 72° C.; degenerate primers: corresponding to peptide 4 (forward) 5'ATHGCITTYGGIGGIAAYTTT3' [SEQ ID NO: 13] and to peptide 5 (reverse): 5'TTICCRAADATIACIACGTT3' [SEQ ID NO: 14]. (D for A, G or T; H stands for A, C or T; M for A or C; I for inosine; R for A or G; Y for C or T). 2.

The TcPA45 coding sequence (from codons 30 to 423) was amplified using 45 s at 94° C., 45 s at 50° C., 3 min at 72° C. for 20 cycles, with primers 5'CTCTCCCATGGGGCAGGAAAAGCTTCTG3' [SEQ ID NO: 15] and 5'CTGAGCTCGACCAGATCTATCTGC3' [SEQ ID NO: 16]. PCR products were purified with Qiagen PCR extraction kit and cloned into pCR II-TOPO vector using the TOPO-TA cloning kit (Invitrogen) following manufacturer's instructions.

Example 5

Automated Sequencing

Lambda phage and plasmid DNA were prepared using standard techniques, and direct sequencing was performed using Big Dye Terminator kit (Perkin Elmer) following manufacturer's instructions. Extension products were run for 7 h in an ABI 373B automated sequencer. Primers internal to the sequence have also been used for sequencing.

Example 6

Genomic Library Screening

A genomic library of *T. cruzi* CL-Brener constructed in phage lambda Fix II (from Dr. E. Rondinelli, UFRJ, Brazil) was screened using a $^{32}$P labelled 239 bp PCR product as a probe. Hybridization was performed using standard conditions. Filters were scanned using a Phosporimager scanning unit (Molecular Dynamics). Positive phages were identified and phage DNA was prepared using standard procedures.

Example 7

Expression Constructs and Recombinant Protein Expression

The PCR product encoding the TcPA45 gene fragment starting at codon 30 was cloned in frame with a C-terminal 6× histidine tag into the pET28b(+) expression vector (Novagen). The soluble recombinant protein was produced in *E. coli*, and the soluble fraction was purified using a $Ni^{2+}$ column (Novagen) following manufacturer's instructions.

Example 8

Racemase Activity

Demonstration of the racemase enzymatic activity of rTcPA 45 used a polarimeter. Buffer Na-acetate (pH 6), reaction Vol. 500 µl. Optimum pH was found to be 6 and the temperature 37° C.

Figure 4E:
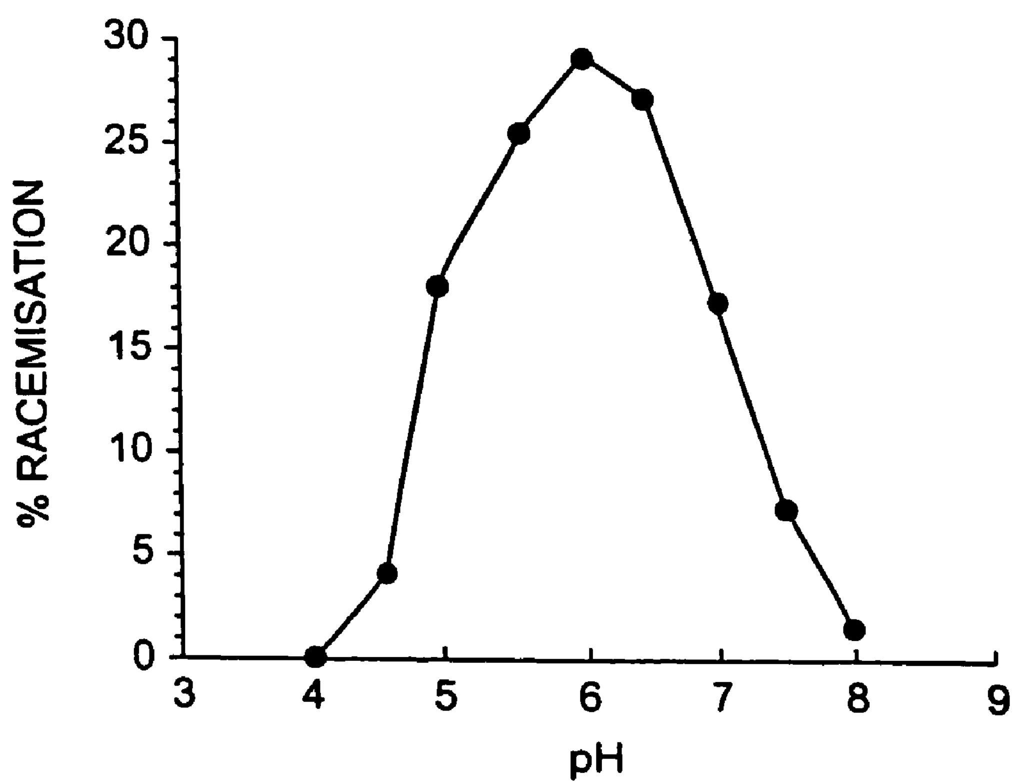
FIG. 4E depicts percent racemization of L-proline (80 mM) as a function of pH (buffers used were 0.2 M: Na-acetate, K-phosphate and Tris-HCl and contained 25 mM β-mercaptoethanol).

3 µg of rTcPA45 was diluted in 500 µl of buffer (0.2M NaOAc, 20 mM β-mercaptoethanol, pH6.0) containing different concentrations of the substrate (10-80 mM or L- or D-proline). (See FIG. 4*c*.) The reaction was incubated for 30-60 minutes at 37° C. in a water bath, followed by heat inactivation of the enzyme for 10 minutes at 80° C. Each sample is diluted to 1.5 ml with water and the mixture submitted to measurement of optical rotation using a polarimeter, at 365 nm. A sample without enzyme is used as a control. For optimal pH determination, buffer systems with NaOAc, phosphate, and Tris were used with pH ranging from 4.0-8.2. Combined results are shown in FIG. 4*e*. Curve of temperature was performed between 27° C. to 47° C.

Example 9

Mitogenic Activity

Analysis of mitogenic proliferative activity of spleen cells in vitro with rTcPA45 (His/tag) protein.

The figure [FIG. 4] is representative of 3 experiments using different mouse strains (C57BL/6, BLAB/c and C3H:HeJ, the latter a LPS-nonresponsive strain). Similar results were obtained with the 3 strains, including C3H/HeJ, showing that our preparation is not contaminated by bacterial LPS. The proliferation is dose-dependent and presents a bi-modal pattern as already observed with total culture supernatants used to purify the Tc45 protein. Best cell concentration=$5\times10^4$ cells/well.

$5\times10^5$ naive spleen cells/well (96 well plate) were stimulated in vitro with different doses of rTcPA45 (ranging in FIG. 4*b* from 0.8 to 200 µg/ml final) for 24, 48 and 72 h, at 37° C., 5% $CO_2$. Cultures were pulsed with $^3$H-Thymidine (1 µCi/well) for 16-18 h before harvesting. $^3$H-thymidine incorporation was obtained after counting using a beta-plate. Results present arithmetic means of c.p.m. (counts/minute) from 6 wells/dose of rTcPA45 or wells containing medium alone (+/−SD of the means).

(FIG. 4*b*)

Example 10

Mitogenicity of rTcPA45 In Vivo Assessed by ELISPOT

BALB/c mice were injected or not with 50 µg of rTcPA45 (i.p.), and spleen cells assayed day 7 after injection. Results represent total numbers of spleen cells, total number of B cells producing IgM, IgG2a, or IgG2b isotypes, and total numbers of isotype-producing B cells specific of the protein.

TABLE 1

ELISPOT assay 7 days after i.p. injection of rTc45MIT

| Total Number of Ig-producing B cells | | | |
|---|---|---|---|
| | IgM-producing cells | IgG2a-producing cells | IgG2b-producing cells |
| Non-injected | 163000 ± 25456 | 3650 ± 636 | 4300 ± 142 |
| PTC45MIT (50 µg/mouse) | 371666 ± 94495 | 9866 ± 3000 | 14633 ± 3287 |
| **Total Number of Ig-producing B cells ANTI-rTc45MIT** | | | |
| | IgM-B cells anti 45 | IgG2a-B cells anti 45 | IgG2b-B cells anti 45 |
| Non-injected | none | none | none |
| PTc45MIT (50 µg/mouse) | 84 | none | none |

It is observed 1) a 2 fold increase in total spleen cell numbers after 7 days of rTcPA45 injection, 2) 3-6 fold increase in total numbers of Ig-secreting cells, and 3) less than 0.5% of IgM secreting cells are directed to the injected protein, characterizing a mitogenic stimulation of B cells.

Mitogenicity of the rTcPA45 In Vivo (Assay)

Mice were injected or not with 50 µg of iTcPA45 (i.p.). 7 days later, spleens were removed and cell suspensions were prepared and counted. Numbers of Ig-secreting cells (total or specific to rTcPA45) were determined by Elispot assay, as follows:

Elispot Assay

Flat bottomed 96 well ELISA plates, were coated with either goat anti-mouse Ig or with rTcPA45 and incubated at 4° C. overnight. Plates were blocked with PBS-gelatin, washed with PBS-Tween and with RPMI medium. 100 µl of different spleen cell concentrations per well (in RPMI containing 2% FCS) were incubated for 8 hours at 37° C., 5% $CO_2$. A row in the plate containing serial dilutions of purified immunoglobulin (IgM, IgG2a, or IgG2b) was used as standard. After lysis of the cells with H20-Tween, plates were then washed with PBS-Tween and incubated with respective biotin-labeled antibodies directed to (IgM, IgG2b, or IgG2a isotypes), overnight at 4 EC. After washing, plates were incubated for 45-60 minutes with avidin-alkaline phosphatase and further incubated with substrate (2-amino-2-methyl-propanol buffer containing BCIP) 2-4 hours, 37° C. (until the spots are "dark" blue). Spots correspond to immunoglobulin-producing B-cell (of a particular isotype) directed to the coated antigen (here: goat anti-mouse immunoglobulins or rTcPA45). Spots are then counted and numbers corrected to total number of spleen cells according to the dilution. (See Table I and FIG. 7.)

Example 11

DNA Vaccination 8 week old BALB/c mice (5 mice/group) were injected (i.m.) once, or 3 times (interval of 3 weeks) with the different constructions (100 Φl plasmid/femoral quadriceps), as follows:

a) controls: saline and rTc24 b) Vectors (pcDNA3 and VR1020, which is described by R. Amasamy et al., Biochemica Biophysica Acta 1998, Vol. 1453, pp. 1-13) of DNA vaccination containing different constructs: Long, containing the complete sequence of rTcPA45 gene; Short, containing the sequence of rTcPA gene without the signal peptide, *VR1020 vector contains an additional signal peptide (tissue Plasminogen Activating factor, TPA).

c) empty vectors

Mice were challenged 4 weeks after the last injection with $10^4$ infective forms of the parasite/mouse, and the parasitemia was scored during 35 days. Serum samples were collected before challenge and assayed by Western blot against the recombinant protein.

It is worth noting that BALB/c mice were treated by almost 2 months (9 weeks) to follow the vaccination protocol and were challenged at 21 week old. It is well known that over 10 week old mice are resistant to the experimental infection with *Trypanosoma cruzi* and no mortality is observed.

The results using this vaccination protocol revealed that 3 injections of pcDNA3 containing either the Short or Long constructs, or just 1 injection of the same vector with the Short construct is able to reduce by more than 50% the parasitemia levels. Titres of total immunoglobulins anti-rTcPA45, 4 weeks after the last plasmid injection:controls (saline and empty vectors): 1:100; both constructs in pcDNA3 (Short and Long): 1:2000, and respectively 1/1000 and 1:2000 for VR1020 containing the Long and Short sequences. (See FIG. 8.)

Example 12

Southern, Western and Northern Blots

Mice were immunized intrasplenically with 10 ng protein and were boosted every 3 weeks with 1 μg of the same preparation for 2 months to obtain polyclonal serum containing rTcPA45-specific antibodies. Total, soluble and insoluble sonic extracts, or culture supernatants from the different parasite forms were purified and separated by 8-10% SDS-PAGE, and proteins were electrophoretically transferred to nitrocellulose membranes. Membranes were saturated with Tris-buffered saline and milk, incubated with polyclonal serum against rTcPA45 and developed with peroxidase-labeled secondary antibody using an ECL kit (Arnersham, Orsay, France). *T. cruzi* genomic DNA (10 μg) was digested with restriction enzymes (BarntII, BglII, SalI, TaqI and PstI), separated by 0.8% agarose gel electrophoresis and transferred to Hyband N+ followed by hybridization of the membrane with a $^{33}$P-dATP-labeled probe covering the TcPA45-coding sequence. Total RNA was prepared from epimastigote, metacyclic and trypomastigote forms of the parasite by conventional methods. For northern blot analysis, 20 μg epimastigote RNA was transferred to Hybond N+ membranes, then hybridized with single-stranded DNA complementary to the TcPA45 gene transcript, labeled with α-$^{32}$P-dCTP.

Transcript analysis through reverse transcription and PCR. Total RNA (1 μg) from epimastigote, metacyclic and trypomastigote forms of the parasite were used to synthesize specific first-strand cDNA by using oligonucleotide R300-45 (5'-TCCGTATCCATGTCGATGC-3') [SEQ ID NO:24], located about 240 nucleotides downstream from the first ATG start codon, followed by PCR amplification using R300-45 and an oligonucleotide corresponding to part of the *T. cruzi* spliced leader sequence (5'-TATTATTGATACAGTTTCTG-3') [SEQ ID NO:25]. An internal TcPA45 fragment of about 170 bp was then amplified using R300-45 and the oligonucleotide HI-45 (5'-CTCTCCCATGGGGCAGGAAAAGCT-TCTG-3') [SEQ ID NO:26] to demonstrate the presence of Tc45 transcript in each of the life stages analyzed.

Example 13

Immunofluorescence

Cellular localization of TcPA45 protein in epimastigote, metacyclic and bloodstream forms of the parasite was demonstrated by indirect immunofluorescence using polyclonal mouse serum against rTcPA45 (described above) followed by 4 μg/ml Alexa 488J goat antibody against mouse IgG (H+I), F(ab')$_2$ fragment conjugate (Molecular Probes-Interchim, Montlucon, France), compared with control staining using Alexa 488™ F(ab')$_2$ fragment conjugate alone or after incubation of the parasites with chronic serum obtained from mice infected for 8 months.

Example 14

Racemization Assays

The percent of racemization of different concentrations of L-proline, D-proline, L-hydroxy-proline and D-hydroxy-proline substrates was calculated by incubating a 500-μl mixture of 3 μg TcPA45 and 10-80 mM substrate in 0.2 M sodium acetate and 25 mM β-mercaptoethanol, pH 6, for 30 min at 37° C. The reaction was stopped by incubation for 10 min at 80° C. Water (1 ml) was then added, and the optical rotation was measured in polarimeter 241 MC (Perkin Elmer, Montignyle Bretonneux, France) at a wavelength of 365 nm, in a cell with a path length of 10 cm. The percent inhibition of racemization of 80 mM L-proline was determined in the presence of different concentrations of several specific and nonspecific inhibitors ranging in concentration from 6 mM to 100 mM. The percent racemization of 80 mM L-proline as a function of pH was determined using 0.2 M sodium acetate, potassium phosphate and Tris-HCl buffers containing 25 mM β-mercaptoethanol; reactions were incubated for 30 min at 37° C. as described above. All reagents and inhibitors were purchased from Sigma.

Accession numbers. The GenBank accession number of *T. cruzi* TcPA45 is AF195522. The EMBL accession number of *C. sticklandii* is E10199.

Example 15 rTcPA45 is a B cell mitogen from a pathogenic trypanosome and a novel eukaryotic proline racemase. Both mitogenic and racemase activities seem to be linked and dependent on the integrity, or the availability of the enzyme active site. Specific inhibition of the active site (using specific or non-specific proline racemase inhibitors), or the active site occupancy by the substrate (competition assays using L- or D-proline), respectively, abolish or decrease B-cell mitogenic properties of rTcPA45.

As with classical B cell mitogens, rTcPA45 mitogenicity is dose-dependent (FIG. 1). As for classical B cell mitogens, mouse specific immune responses directed to mitogenic rTcPA45 is indeed possible (Western blot FIG. 12) following a protocol of immunization which consisted of with 1 injection (i.p.) of a sub-mitogenic (10 ng/mouse) dose of the protein followed by an additional boost with a mitogenic dose of rTcPA45 (50 μg/mouse) one week later.

Protocol 5 groups of 6 week old Balb/c mice (3 mice per group) were immunized as follows:

T=non immunized.

Vide=immunized with 50 μg of empty PcDNA3 vector, i.m. per 3 week (twice).

Court=immunized with 50 μg of PcDNA3—short (TcPA45 short), i.m. per week (twice).

I.S.=immunized with 10 ng of rTcPA45 i.s. (first week) and 50 μg rTcPA45 i.p. (second week).

I.P.=immunized with 10 ng of rTcPA45 i.p. (first week) and 50 μg rTcPA45 i.p. (second week).

Sera from individual mice were collected and analyzed by Western blot:

80 μg of rTcPA45 were loaded onto 0.8% SDS-page gels and transferred to Hybond membranes.

Sera were individually tested at 1/400 dilution and reactivity against rTcPA45 revealed with anti-IgG mice immunoglobulins using chemuluminescence.

FIG. 12 (J-14) represents individual serum reactivity before immunization before challenge (J0), and after 10 days (J10) or 21 days (J21) of challenge. Challenge consisted of i.p 10000 parasites.

Additionally, rTcPA45 molecule can be considered as a target for vaccination strategies, since the previous Example using DNA-vaccination protocols (intramuscular injections of DNA-vectors containing the Tc45 gene) was able to reduce by 85% the parasitemia levels after an infectious challenge with the parasite. (See FIG. 14*a*.)

Moreover, experiments showed that higher levels of parasitemia control (90-95%) was obtained when the submitogenic protocol of immunization described above was followed by an infectious challenge (1 parasites/mouse). These additional results do support the claim that mitogenic moieties are potential targets for vaccination approaches against *Trypanosoma cruzi* infection. (See FIG. 14(*b*).)

In summary, we have investigated the mechanisms and consequences of polyclonal lymphocyte activation using the experimental model of Chagas disease, caused by the protozoan parasite *T. cruzi*. As in other infectious processes, this disease involves extensive B- and T-cell activation, hypergammaglobulinemia, and the establishment of chronic autoimmunity affecting the heart and the digestive tract. *Trypanosoma cruzi* infection induces a lymphocyte blast transformation of a magnitude that is similar to or higher than that induced by the classic polyclonal activator LPS.

This invention involves the use of a parasite or viral mitogen as a vaccinating agent without lymphocyte polyclonal activation that inhibits a protective host specific immune response to the parasite or virus. This invention not only prevents infection by the parasite or virus, but also avoids the negative consequences of such infection (immunosuppression, persistent infection, and susceptibility to immunopathology and autoimmune phenomenon). This invention thus addresses the correlation of polyclonal lymphocyte activation of the immune system after infections with poor specific responses and severe immunosuppression to autologous or unrelated challenges through an effective vaccination strategy.

REFERENCES

The following publications are cited herein. The entire disclosure of each publication is relied upon and incorporated by reference herein.

1. Reina-San-Martin, B., Cosson, A. & Minoprio, P. Lymphocyte polyclonal activation: a pitfall for vaccine design against infectious agents. *Parasitol. Today* 16(2); 62-67 (2000).
2. Minoprio, P., Itohara, S., Heusser, C., Tonegawa, S. & Coutinho, A. Immunobiology of murine *T. cruzi* infection: the predominance of parasite-nonspecific responses and the activation of TcRI T cells *Immunol. Rev.* 112, 183-207 (1989).
3. Eisen, H., Petry, K. & Voorhis, W. V. *The origin of the autoimmune pathology associated with Trypanosoma cruzi infection* (Academic Press, Inc., New York, 1990).
4. Ribeiro-dos-Santos, R., et al. Anti-CD4 abrogates rejection and reestablishes long-term tolerance to syngeneic newborn hearts grafted in mice chronically infected with *Trypanosoma cruzi J. Exp. Med.* 175, 29-39 (1992).
5. Tarleton, R., Zhang, L. & Downs, M. Autoimmune rejection of neonatal heart transplants in experimental Chagas' disease is a parasite-specific response to infected host tissue. *P.N.A.S.* 94, 3932-3937 (1997).
6. Arala-Chaves, M., d'Imperio-Lima, M. R., Coutinho, A., Pena-Rossi, C. & Minoprior, P. V-region-related and -unrelated immunosuppression accompanying infections *Mem. Inst. Osw. Cruz* 87, 35-41 (1992).
7. Minoprio, P., Eisen, H., Joskowicz, M., Pereira, P. & Coutinho, A. Suppression of polyclonal antibody production in *Trypanosoma cruzi* infected mice by treatment with anti-L3T4 antibodies. *J. Immunol.* 139, 545-550 (1987).
8. Minoprio, P., Coutinho, A., Spinella, S. & Hontebeyrie-Joskowicz, M. Xid immunodeficiency imparts increased parasite clearance and resistance to pathology in experimental Chagas' disease *Internat. Immunol.* 3, 427-433 (1991).
9. Santos-Lima, E. C. & Minoprio, P. Chagas' disease is attenuated in mice lacking γδ T cells *Infec. Immun.* 64, 215-221 (1996).
10. Cordeiro, da Silva, A., Guevara Espinoza, A., Taibi, A., Ouaissi, A. & Minoprio, P. A 24 kDa *Trypanosoma cruzi* antigen is a B cell activator *Immunology* 94, 189-196 (1998).
11. Contreras, V. T., Salles, J. M., Thomas, N., Morel, C. M. & Goldenberg, S. In vitro differentiation of *Trypanosoma cruzi* under chemically defined conditions. *Mol. Biochem. Parasitol.* 16, 315-327 (1985).
12. Dragon, E. A., Sias, S. R., Kato, E. A. & Gabe, J. D. The genome of *Trypanosoma cruzi* contains a constitutively expressed, tandemly arranged multicopy gene homologous to a major heat shock protein. *Mol. Cell. Biol.* 7, 1271-1275 (1987).

13. Moro, A., Ruiz-Cabello, F., Fernandez-Cano, A., Stock, R. P. & Gonzalez, A. Secretion by *Trypanosoma cruzi* of a peptidyl-prolyl cis-trans isomerase involved in cell infection. *EMBO Journal* 14(11), 2483-2490 (1995).
14. Cardinale, G. J. & Abeles, R. H. Purification and mechanism of action of proline racemase. *Biochemistry* 7(11), 3970-3978 (1968).
15. Rudnick, G. & Abeles, R. Reaction mechanism and structure of the active site of proline racemase. *Biochem.* 14(20), 4515-4522 (1975).
16. Lamzin, V. S., Zbigniew, D. & Wilson, K. S. How nature deals with stereoisomers. *Curr. Op. Struct. Biol.* 5, 830-836 (1995).
17. Barret, F. M. Changes in the concentration of free amino acids in the haemolymph of *Rhodnius prolixus* during the fifth instar. *Comp. Biochem. Physiol.* 48(B), 241-250 (1973).
18. Sylvester, D. & Krassner, S. M. Proine metabolism in *Trypanosoma cruzi* epimastigotes. *Comp. Biochem. Physiol.* 55(B), 443-447 (1976).
19. de Isola, E. L., Lammel, E. M., Katzin, V. J. & Gonzalez Cappa, S. M. Influence of organ extracts of *Triatoma infestans* on differentiation of *Trypanosoma cruzi. J. Parasitol.* 67(1), 53-58 (1981).
20. Rosenberg, R. D., et al. Heparan sulfate proteoglycans of the cardiovascular system: specific structures emerge but how is synthesis regulated? *J. Clin. Inv.* 100(11S), 67S-75S (1997).
21. Herrera, E. M., Ming, M., Ortega-Barria, E. & Pereira, M. E. Mediation of *Trypanosoma cruzi* invasion by heparan sulfate receptors on host cells and penetrin counter receptors on the trypanosomes. *Mol. Biochem. Parasitol.* 75(1), 73-83 (1994).
22. Ortega-Barria, E. & Pereira, M. E. A novel *T. cruzi* heparin binding protein promotes fibroblast adhesion and penetration of engineered bacteria and trypanosomes into mammalian cells. *Cell* 67, 411-421 (1991).
23. Shakibaei, M. & Frevert, U. Dual interaction of the malaria circunsporozoite protein with the low density lipoprotein receptor related (LRP) and heparan sulfate proteoglycans. *J. Exp. Med.* 184, 1699-1711 (1996).
24. Thompson, R. J., Bouwer, H. G., Portnoi, D. A. & Frankel, F. R. Pathogenicity and immunogenicity of a *Listeria monocytogenes* strain that requires D-alanine for growth. *Inf. Immun.* 66(8), 3552-3561 (1998).
25. Mozes, E., Sela, M. & Taussig, M. J. Tolerance to thymus independent antigens. Characteristics of induction of tolerance to thymus independent synthetic polypeptides. *Immunol.* 27, 641-646 (1974).
26. Sela, M. & Zisman, E. Different rols of D-amino acids in immune phenomena. *FASEB J.* 11, 449-456 (1997).
27. Coutinho, A. & Moller, G. B cell mitogenic properties of thymus-independent antigens *Nature* 245, 12-14 (1973).
28. Coutinho, A., Gronowicz, E., Bullock, W. W. & Moller, G. Mechanism of thymus-independent immunocyte triggering. Mitogenic activation of B cells results in specific immune responses. *J. Exp. Med.* 139(1), 74-92 (1974).
29. Janeway, C. A. & Humphrey, J. H. Synthetic antigens composed exclusively of L- or D-amino acids. II. Effect of optical configuration on the metabolism and fate of synthetic polypeptide antigens in mice. *Folia Biol.* 16(3), 156-172 (1970).
30. d'Imperio-Lima, M. R., Eisen, H., Minoprio, P., Joskowicz, M. & Coutinho, A. Persistence of polyclonal B cell activation with undetectable parasitemia in late stages of experimental Chagas' disease. *J. Immunol.* 137, 353-356 (1986).
31. Tavares, D., Ferreira, P., Vilanova, M., Videira, A. & Arala-Chaves, M. Immunoprotection against systemic candidiasis in mice. *Int. Immunol.* 7(5), 785-96 (1995).
32. in *D-amino acids in sequences of secreted peptides of multicellular organisms*. (eds. Jolles, P.) (Birkhauser Verlag, Basel, 1998).
33. Wolosker, H., et al. Purification of serine racemase: biosynthesis of the neuromodular D-serine. *Proc. Natl. Acad. Sci. USA* 96, 721-725 (1999).

What is claimed is:

1. A purified nucleic acid molecule comprising the sequence of SEQ ID NO: 8.

2. A recombinant vector that directs the expression of a nucleic acid molecule of claim 1.

3. An isolated host cell transfected or transduced with the vector of claim 2.

4. A kit comprising:

(a) a polynucleotide primer or probe, comprising at least 10 and not more than 40 nucleotides capable of hybridizing to the nucleic acid molecule of claim 1 under conditions of moderate stringency; and (b) reagents to perform a nucleic acid hybridization reaction and/or amplification reaction.

5. A purified nucleic acid molecule comprising:

(A) a molecule that hybridizes to the complementary strand of SEQ ID NO: 8 under conditions of moderate stringency;

(B) a molecule that has at least 80% identity to SEQ ID NO: 8; or (C) a molecule that is degenerate from SEQ ID NO: 8 as a result of the genetic code.

6. A recombinant vector that directs the expression of a nucleic acid molecule of claim 5.

7. An isolated host cell transfected or transduced with the vector as claimed in claim 6.

8. A kit comprising:

(A) a polynucleotide primer or probe comprising at least 10 and not more than 40 nucleotides capable of hybridizing to the nucleic acid molecule of claim 5 under conditions of moderate stringency; and (B) reagents to perform a nucleic acid hybridization reaction and/or amplification reaction.

9. A kit comprising:

(A) at least one polynucleotide chosen from SEQ ID NOS: 12, 13, 14, 15, and 16; and (B) reagents to perform a nucleic acid hybridization and/or amplification reaction.

10. The kit of claim 4, wherein the polynucleotide is labeled.

11. The kit of claim 8, wherein the polynucleotide is labeled.

12. The kit of claim 9, wherein the polynucleotide is labeled.

13. The kit of claim 4, further comprising a second polynucleotide comprising at least 10 and not more than 40 nucleotides capable of hybridizing to the nucleic acid molecule of claim 1 under conditions of moderate stringency.

14. The kit of claim 8, further comprising a second polynucleotide comprising at least 10 and not more than 40 nucleotides capable of hybridizing to the nucleic acid molecule of claim 5 under conditions of moderate stringency.

15. The kit of claim 9, further comprising a second polynucleotide comprising at least 10 nucleotides capable of hybridizing to the nucleic acid molecule of claim 1 or 5 under conditions of moderate stringency.

* * * * *

UNITED STATES PATENT AND TRADEMARK OFFICE

CERTIFICATE OF CORRECTION

PATENT NO. : 8,168,770 B2
APPLICATION NO. : 11/378706
DATED : May 1, 2012
INVENTOR(S) : Paolo Minoprio et al.

It is certified that error appears in the above-identified patent and that said Letters Patent is hereby corrected as shown below:

Title Page, item (73), lines 2-3,

“Instituto Gulbekian De Cienca” should read

-- Instituto Gulbenkian de Ciencia --.

Signed and Sealed this
Tenth Day of July, 2012

David J. Kappos
*Director of the United States Patent and Trademark Office*